US012758732B2

(12) United States Patent
Creusot et al.

(10) Patent No.: US 12,758,732 B2
(45) Date of Patent: Oct. 13, 2026

(54) PATIENT INTERFACE FOR RESPIRATORY THERAPY

(71) Applicant: ResMed Pty Ltd, Bella Vista (AU)

(72) Inventors: David Creusot, Sydney (AU); Liam Holley, Sydney (AU); Paul Jan Klasek, Sydney (AU); Gordon Joseph Malouf, Sydney (AU); Klaus Henry Schindhelm, Sydney (AU); Quangang Yang, Kellyville (AU)

(73) Assignee: ResMed Pty Ltd (AU)

( * ) Notice: Subject to any disclaimer, the term of this patent is extended or adjusted under 35 U.S.C. 154(b) by 0 days.

(21) Appl. No.: 17/384,309

(22) Filed: Jul. 23, 2021

(65) Prior Publication Data

US 2021/0346633 A1 Nov. 11, 2021

Related U.S. Application Data

(63) Continuation of application No. 15/316,287, filed as application No. PCT/AU2015/050342 on Jun. 19, 2015, now Pat. No. 11,123,511.

(Continued)

(51) Int. Cl.
*A61M 16/06* (2006.01)
*A61M 16/00* (2006.01)
(Continued)

(52) U.S. Cl.
CPC .... *A61M 16/0672* (2014.02); *A61M 16/0066* (2013.01); *A61M 16/024* (2017.08);
(Continued)

(58) Field of Classification Search
CPC .......... A61M 16/0666; A61M 16/0672; A61M 16/0677
See application file for complete search history.

(56) References Cited

U.S. PATENT DOCUMENTS 3,814,091 A 6/1974 Henkin
4,106,505 A 8/1978 Salter et al.
(Continued)

FOREIGN PATENT DOCUMENTS

CN 101455871 A 6/2009
CN 101479010 A 7/2009
(Continued)

OTHER PUBLICATIONS

Japanese Office Action for Application No. JP2022-062222 dated Sep. 27, 2022.

(Continued)

*Primary Examiner* — LaToya M Louis
(74) *Attorney, Agent, or Firm* — Botos Churchill IP Law LLP

(57) ABSTRACT

Apparatus permit a delivery of a flow of breathable gas to a patient's airways. In one version, a coupler extension may include a seat portion to permit use of a mask with a nasal cannula. In some versions, the coupler extension is configured to conduct the flow of gas to prongs of a nasal cannula. The seat portion can receive and seal with a cushion of a respiratory mask and may have a sealing bevel to promote sealing between the cushion of the respiratory mask and a facial contact surface of a user. In some versions, a nasal interface may include naris pillows to seal with and conduct a flow of breathable gas into a nares of a user. Each naris pillow may include a nasal projection to conduct a further flow of gas. The nasal projection may extend within the naris beyond the seal of the naris pillow.

20 Claims, 40 Drawing Sheets

Related U.S. Application Data

(60) Provisional application No. 62/014,225, filed on Jun. 19, 2014.

(51) Int. Cl.

| | |
|---|---|
| ***A61M 16/10*** | (2006.01) |
| ***A61M 16/16*** | (2006.01) |
| *A61M 16/20* | (2006.01) |

(52) U.S. Cl.

CPC .... *A61M 16/0605* (2014.02); *A61M 16/0616* (2014.02); *A61M 16/0666* (2013.01); *A61M 16/105* (2013.01); *A61M 16/16* (2013.01); *A61M 2016/0027* (2013.01); *A61M 2016/003* (2013.01); *A61M 16/1055* (2013.01); *A61M 16/107* (2014.02); *A61M 16/208* (2013.01); *A61M 16/209* (2014.02); *A61M 2202/0208* (2013.01); *A61M 2205/505* (2013.01)

(56) References Cited

U.S. PATENT DOCUMENTS

| | | | | |
|---|---|---|---|---|
| 4,328,797 | A | 5/1982 | Rollins et al. | |
| 4,782,832 | A * | 11/1988 | Trimble | A61M 16/0633 128/207.18 |
| 4,944,310 | A | 7/1990 | Sullivan | |
| 5,474,060 | A | 12/1995 | Evans | |
| 5,509,409 | A | 4/1996 | Weatherholt | |
| 6,431,172 | B1 * | 8/2002 | Bordewick | A61M 16/0666 128/207.18 |
| 6,478,026 | B1 | 11/2002 | Wood | |
| 6,532,959 | B1 | 3/2003 | Berthon-Jones | |
| 6,581,594 | B1 | 6/2003 | Drew et al. | |
| 7,866,944 | B2 | 1/2011 | Kenyon et al. | |
| 8,136,525 | B2 * | 3/2012 | Lubke | A61M 16/20 128/206.28 |
| 8,418,690 | B2 | 4/2013 | Power et al. | |
| 8,573,219 | B2 | 11/2013 | Wondka | |
| 8,636,479 | B2 | 1/2014 | Barton et al. | |
| 8,638,014 | B2 | 1/2014 | David | |
| 10,478,580 | B2 | 11/2019 | Klenner et al. | |
| 10,716,912 | B2 | 7/2020 | Holyoake et al. | |
| 11,602,607 | B2 * | 3/2023 | Lau | A61M 16/0672 |
| 2002/0156430 | A1 | 10/2002 | Haarala et al. | |
| 2003/0172936 | A1 * | 9/2003 | Wilkie | A61M 16/0683 128/207.18 |
| 2005/0011524 | A1 * | 1/2005 | Thomlinson | A61M 16/0825 128/207.18 |
| 2006/0266361 | A1 | 11/2006 | Hernandez | |
| 2007/0119454 | A1 | 5/2007 | Berthon-Jones et al. | |
| 2008/0178880 | A1 | 7/2008 | Christopher et al. | |
| 2009/0044808 | A1 * | 2/2009 | Guney | A61M 16/0605 128/207.18 |
| 2009/0050156 | A1 | 2/2009 | Ng et al. | |
| 2009/0253995 | A1 | 10/2009 | Lewis et al. | |
| 2009/0320851 | A1 * | 12/2009 | Selvarajan | A61M 16/0683 128/207.13 |
| 2010/0000534 | A1 | 1/2010 | Kooij et al. | |
| 2010/0108073 | A1 * | 5/2010 | Zollinger | A61M 16/0611 128/207.13 |
| 2011/0073116 | A1 | 3/2011 | Genger et al. | |
| 2011/0094518 | A1 | 4/2011 | Cipollone et al. | |
| 2011/0114096 | A1 * | 5/2011 | Matula, Jr. | A61M 16/0666 128/207.18 |
| 2011/0162655 | A1 * | 7/2011 | Gunaratnam | A61M 16/08 128/207.18 |
| 2011/0203591 | A1 | 8/2011 | Amarasinghe | |
| 2011/0253136 | A1 | 10/2011 | Sweeney et al. | |
| 2012/0125338 | A1 | 5/2012 | Yarahmadi | |
| 2012/0285461 | A1 | 11/2012 | Pierro et al. | |
| 2013/0104903 | A1 * | 5/2013 | Matula, Jr. | A61M 16/0875 128/207.13 |
| 2013/0184602 | A1 | 7/2013 | Brambilla | |
| 2013/0186404 | A1 * | 7/2013 | Chien | A61M 16/0825 128/206.21 |
| 2013/0199537 | A1 | 8/2013 | Formica et al. | |
| 2014/0018691 | A1 | 1/2014 | McNeill | |
| 2014/0107517 | A1 | 4/2014 | Hussain | |
| 2014/0150789 | A1 | 6/2014 | Flanagan et al. | |
| 2014/0332005 | A1 * | 11/2014 | Kunz | A61M 16/0825 128/205.25 |
| 2014/0366877 | A1 * | 12/2014 | Selvarajan | A61M 16/0009 128/205.12 |
| 2014/0366885 | A1 * | 12/2014 | Haibach | A61M 16/0611 128/206.24 |
| 2015/0013678 | A1 * | 1/2015 | McAuley | A61M 16/16 128/203.22 |
| 2015/0128948 | A1 * | 5/2015 | Rapoport | A61M 16/0866 128/204.23 |
| 2016/0022951 | A1 * | 1/2016 | Galbraith | B01D 53/0415 96/147 |
| 2020/0101250 | A1 * | 4/2020 | Nelson | A61M 16/0616 |
| 2020/0114109 | A1 * | 4/2020 | Klenner | A61M 16/0066 |
| 2023/0036185 | A1 * | 2/2023 | Judson | A61M 16/0825 |

FOREIGN PATENT DOCUMENTS

| | | | |
|---|---|---|---|
| CN | 102762249 | A | 10/2012 |
| EM | 1484075 | A1 | 12/2004 |
| EP | 1484075 | A1 | 12/2004 |
| JP | 3191966 | A | 8/1991 |
| JP | 2004329255 | A | 11/2004 |
| JP | 2009039528 | A | 2/2009 |
| JP | 2011502685 | A | 1/2011 |
| JP | 2013515560 | A | 5/2013 |
| JP | 2017508563 | A | 3/2017 |
| JP | 2018510016 | A | 4/2018 |
| WO | 8200254 | A | 2/1982 |
| WO | 9220392 | A1 | 11/1992 |
| WO | 1998004310 | A1 | 2/1998 |
| WO | 1998034665 | A1 | 8/1998 |
| WO | 00078381 | A1 | 12/2000 |
| WO | 2000078381 | | 12/2000 |
| WO | 2004073778 | A1 | 9/2004 |
| WO | 2005051468 | A1 | 6/2005 |
| WO | 2005063328 | A1 | 7/2005 |
| WO | 2006074513 | A1 | 7/2006 |
| WO | 2006130903 | A1 | 12/2006 |
| WO | 2009052560 | A1 | 4/2009 |
| WO | 2009103288 | A1 | 8/2009 |
| WO | 2009109005 | A1 | 9/2009 |
| WO | 2009132753 | A1 | 11/2009 |
| WO | 2010135785 | A1 | 12/2010 |
| WO | 2011030250 | A1 | 3/2011 |
| WO | 2011068418 | A1 | 6/2011 |
| WO | 2011078703 | A1 | 6/2011 |
| WO | 2012149512 | A2 | 11/2012 |
| WO | 2013020167 | A1 | 2/2013 |
| WO | 2013040198 | A2 | 3/2013 |
| WO | 2013148901 | A1 | 10/2013 |
| WO | 2013155349 | A1 | 10/2013 |
| WO | 2014089188 | A1 | 6/2014 |
| WO | 2014138803 | A1 | 9/2014 |
| WO | 2015130179 | A1 | 9/2015 |
| WO | 2015145390 | A1 | 10/2015 |
| WO | 2016157105 | A1 | 10/2016 |

OTHER PUBLICATIONS

EP Communication dated Jan. 29, 2020 for EP Application No. 15 80 9410.2.

International Search Report and Written Opinion for Application No. PCT/AU2015/050342 dated Sep. 8, 2015.

Notice of Allowance from JP Patent Application No. 2016-573464.

NZ Examination Report dated Oct. 27, 2020 for NZ Patent No. 762936.

Extended European Search Report issued in corresponding EP application No. 15809410.2 on Feb. 16, 2018., pp. 8.

"Confidence in you patient's Comfort Brochure", www.philips.com/NIVmasks, Koninklijke Philips Electronics N.V., Jan. 2012, 30-31.

(56) References Cited

OTHER PUBLICATIONS

"Image 3 Full Face Mask Instructions for Use", www.respironics.com, Sep. 14, 2001.
"Image 3 SE Displosable Full Face Mask Brochure", www.respironics.com, Respironics, Inc., Nov. 22, 2002.
"N-G Tube Sealing Pad Package/Product", circa 2001.
West, John B, "Respiratory Physiology", Lippincott Williams & Wilkins, 9th edition published 2011.
Decision to Grant a Patent for Japanese Patent Application No. 2020-202795, Mar. 4, 2022.
The Extended European Search Report for European Patent Application No. 21165439.7, Aug. 4, 2021.
The First Office Action for Chinese Patent Application No. 201911072121.6, Oct. 15, 2021.
Amended Statement of Case filed in corresponding New Zealand Patent Application No. 798329, filed Apr. 28, 2025, in the matter of an opposition between ResMed Pty Ltd and Fisher & Paykel Healthcare Limited, 17 pages.
Statutory declaration of Adam John Darby concerning the opposition to New Zealand Patent Application No. 780711, dated Jan. 3, 2025, 74 pages.
Office Action issued in corresponding Chinese Patent Application No. 2022111711904, mailed Jun. 27, 2025, 18 pages.
Counterstatement in the matter of an application for Letters Patent No. 798329 in the name of Resmed Pty Ltd and in the matter of an opposition thereto by Fisher & Paykel Healthcare Limited, Jun. 26, 2025, 23 pages.
Statutory Declaration of Glenn Norman Richards in support of New Zealand Patent Application No. 780711, dated Jul. 1, 2025, 92 pages.
Frat, M.D., et al., "High-Flow Oxygen through Nasal Cannula in Acute Hypoxemic Respiratory Failure", The New England Journal of Medicine 372;23 nejm.org Jun. 4, 2015. Downloaded from nejm.org on Jul. 8, 2025., 2185-2196.
Mayfield, et al., "High-flow nasal cannula therapy for respiratory support in children", Cochrane Library, Cochrane Database of Systematic Reviews 2014, Issue 3. Art. No. CD009850, 31 pages. DOI: 10.1002/14651858.CD009850.pub2.
Exhibit AJD-3—Oxygen Therapy—using Draager Evita ventilators to their full potential, pp. 123-127 of Statutory Declaration of Adam John Darby, Nov. 3, 2025.
Exhibit AJD-4—Application of Dual Mask for Postoperative Respiratory Support in Obstructive Sleep apnea Patient, pp. 128-131 of Statutory Declaration of Adam John Darby, Nov. 3, 2025.
Exhibit RLP-10—High Flow nasal oxygen generates positive airway pressure in adult volunteers, pp. 121-127 of Statutory Declaration of Dr Rachael Parke, Nov. 3, 2025.
Exhibit RLP-11—F&P Optiflow—Extending the boundaries of oxygen therapy, pp. 128-129 of Statutory Declaration of Dr Rachael Parke, Nov. 3, 2025.
Exhibit RLP-2—Effect of Very-High-Flow Nasal Therapy on Airway Pressure and End-Expiratory Lung Impedance in Healthy Volunteers, pp. 16-22 of Statutory Declaration of Dr Rachael Parke, Nov. 3, 2025.
Exhibit RLP-3—High-Flow Oxygen Administration by Nasal Cannula for Adult and Perinatal Patients, pp. 23-48 of Statutory Declaration of Dr Rachael Parke, Nov. 3, 2025.
Exhibit RLP-4—Optiflow Nasal High Flow Therapy—The CVIUCU/HDU Auckland City Hospital Protocol for Use, pp. 49-51 of Statutory Declaration of Dr Rachael Parke, Nov. 3, 2025.
Exhibit RLP-5—Oxygen therapy in non-intubated adult intensive care patients: a point prevalence study, pp. 52-59 of Statutory Declaration of Dr Rachael Parke, Nov. 3, 2025.
Exhibit RLP-6—Pressures Delivered By Nasal High Flow Oxygen During All Phases of the Respiratory Cycle, pp. 60-64 of Statutory Declaration of Dr Rachael Parke, Nov. 3, 2025.
Exhibit RLP-7—High Flow Nasal Oxygen Therapy in Patients After Cardiac Surgery, pp. 65-108 of Statutory Declaration of Dr Rachael Parke, Nov. 3, 2025.
Exhibit RLP-8—Nasal high-flow therapy delivers low level positive airway pressure, pp. 109-114 of Statutory Declaration of Dr Rachael Parke, Nov. 3, 2025.
Exhibit RLP-9—The Effects of Flow on Airway Pressure During Nasal High-Flow Oxygen Therapy, pp. 115-120 of Statutory Declaration of Dr Rachael Parke, Nov. 3, 2025.
Statutory declaration of Adam John Darby concerning the opposition to New Zealand Patent Application No. 780711, dated Nov. 3, 2025, 131 pages.
Statutory declaration of Dr Rachael Louise Parke concerning the opposition to New Zealand Patent Application No. 780711, dated Nov. 3, 2025, 129 pages.
Office Action issued in corresponding Chinese Patent Application No. 2022111711904, mailed Feb. 14, 2026, 18 pages.
Submissions for the opponent in support of the opposition to Patent Application No. 780711, dated Mar. 3, 2026, 71 pages.
Submissions of the Applicant, in the matter of an application for Letters Patent No. 780711, dated Mar. 10, 2026, 80 pages.
Correspondance from IPONZ on Decision of Commissioner, Proceeding 7298, IP No. 780711, Applicant RESMED Pty Ltd, Opponent Fisher & Paykel Healthcare Limited, dated Jul. 6, 2026, 2 pages.
Decision of Assistant Commissioner Luiten, under the Patent Act 1953, in the mater of patent application 780711, regarding an opposition between Resmed Pty Ltd and Fisher & Paykel Healthcare Limited, hearing date Mar. 17-18, 2026., 43 pages.

* cited by examiner

PATIENT INTERFACE FOR RESPIRATORY THERAPY

1 CROSS-REFERENCE TO RELATED APPLICATIONS

This application is a continuation of U.S. patent application Ser. No. 15/316,287, filed on Dec. 5, 2016, which is a national phase entry under 35 U.S.C. § 371 of International Application No. PCT/AU2015/050342, filed Jun. 19, 2015, published in English, which claims priority from U.S. Provisional Patent Application No. 62/014,225, filed Jun. 19, 2014, all of which are incorporated herein by reference.

2 BACKGROUND OF THE INVENTION

2.1 Field of the Invention

The present technology relates to one or more of the detection, diagnosis, treatment, prevention and amelioration of respiratory-related disorders. In particular, the present technology relates to medical devices or apparatus, and their use and may include devices for directing treatment gas to a patient's respiratory system such as by the nasal passages.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilatory support to a patient through the upper airways to assist the patient in taking a full breath and/or maintain adequate oxygen levels in the body by doing some or all of the work of breathing. The ventilator support is provided via a patient interface. NIV has been used to treat CSR, OHS, COPD, MD and Chest Wall disorders.

Invasive ventilation (IV) provides ventilatory support to patients that are no longer able to effectively breathe themselves and may be provided using a tracheostomy tube.

Ventilators may control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

2.2.3 Systems

One known device used for treating sleep disordered breathing is the S9 Sleep Therapy System, manufactured by ResMed. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

A system may comprise a PAP Device/ventilator, an air circuit, a humidifier, a patient interface, and data management.

2.2.4 Patient Interface

A patient interface may be used to interface respiratory equipment to its user, for example by providing a flow of breathable gas. The flow of breathable gas may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 $cmH_2O$. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, mask designed as part of personal protection equipment (e.g. filter masks), SCUBA masks, or for the administration of anaesthetics may be tolerable for their original application, but nevertheless be undesirably uncomfortable to be worn for extended periods of time, e.g. several hours. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, masks for respiratory therapy form a distinct field.

2.2.4.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be in appropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

2.2.4.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

2.2.4.3 Vent Technologies

Some forms of patient interface systems may include a vent to allow the washout of exhaled carbon dioxide. The vent may allow a flow of gas from an interior space of the patient interface, e.g. the plenum chamber, to an exterior of the patient interface, e.g. to ambient. The vent may comprise an orifice and gas may flow through the orifice in use of the mask. Many such vents are noisy. Others may block in use and provide insufficient washout. Some vents may be disruptive of the sleep of a bed-partner 1100 of the patient 1000, e.g. through noise or focussed airflow.

ResMed Limited has developed a number of improved mask vent technologies. See WO 1998/034,665; WO 2000/078,381; U.S. Pat. No. 6,581,594; US patent application; US 2009/0050156; US Patent Application 2009/0044808.

Table of noise of prior masks (ISO 17510-2:2007, 10 cm$H_2O$ pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

(* one specimen only, measured using test method specified in ISO3744 in CPAP mode at 10cm$H_2O$)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.5 Respiratory Apparatus (PAP Device/Ventilator)

Examples of respiratory apparatuses include ResMed's S9 AutoSet™ PAP device and ResMed's Stellar™ 150 ventilator. Respiratory apparatuses typically comprise a pressure generator, such as a motor-driven blower or a compressed gas reservoir, and are configured to supply a flow of air or other breathable gases to the airway of a patient, typically via a patient interface such as those described above. In some cases, the flow of air or other breathable gases may be supplied to the airway of the patient at positive pressure. The outlet of the respiratory apparatus is connected via an air circuit to a patient interface such as those described above.

Table of noise output levels of prior devices (one specimen only, measured using test method specified in ISO3744 in CPAP mode at 10cm$H_2O$).

| Device name | A-weighted sound power level dB(A) | Year (approx.) |
|---|---|---|
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 AutoSet | 26.5 | 2010 |
| S9 AutoSet with H5i Humidifier | 28.6 | 2010 |

2.2.6 Humidifier

Delivery of a flow of breathable gas without humidification may cause drying of airways. Medical humidifiers are used to increase humidity and/or temperature of the flow of breathable gas in relation to ambient air when required, typically where the patient may be asleep or resting (e.g. at a hospital). As a result, a medical humidifier is preferably small for bedside placement, and it is preferably configured to only humidify and/or heat the flow of breathable gas delivered to the patient without humidifying and/or heating the patient's surroundings. Room-based systems (e.g. a sauna, an air conditioner, an evaporative cooler), for example, may also humidify air that is breathed in by the patient, however they would also humidify and/or heat the entire room, which may cause discomfort to the occupants.

The use of a humidifier with a respiratory apparatus and the patient interface produces humidified gas that minimizes drying of the nasal mucosa and increases patient airway comfort. In addition in cooler climates, warm air applied generally to the face area in and about the patient interface is more comfortable than cold air.

Respiratory humidifiers are available in many forms and may be a standalone device that is coupled to a respiratory apparatus via an air circuit, integrated with the respiratory apparatus or configured to be directly coupled to the relevant respiratory apparatus. While known passive humidifiers can provide some relief, generally a heated humidifier may be used to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator or PAP device, and a gas outlet adapted to be connected to an air circuit that delivers the humidified gas to the patient interface.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

Some versions of the present technology may relate to an improved patient interface.

Some versions of the present technology may relate to an improved nasal interface.

Some versions of the present technology may relate to an improved nasal cannula for use with mask.

Some versions of the present technology may relate to an improved nasal interface with nasal projections.

Some versions of the present technology may relate to improved nasal pillows with nasal projections.

Some versions of the present technology may include an apparatus for delivery of a flow of breathable gas to a patient's airways. The apparatus may include a nasal cannula including a set of projections, each projection configured to conduct a flow of gas into a naris of a user. The apparatus may further include a coupler extension configured to conduct the flow of gas to the set of projections. The coupler may be configured to couple with one or more gas supply lines of a breathable gas source. The coupler extension may include a seat portion. The seat portion may be configured to receive and seal with a cushion of a respiratory mask. The seat portion may have a sealing bevel to promote sealing between the cushion of the respiratory mask and a facial contact surface of a user.

Optionally in some versions, the coupler extension may include a plurality of seat portions. Each seat portion may include a triangular profile. Each seat portion may include a lentil profile. Each seat portion may include a first flow passage. Each seat portion may include a second flow passage. Each flow passage of a seat portion may include a round gas flow passage. Each flow passage of a seat portion may include a rectangular gas flow passage. The set of projections may include first and second nasal prongs. The apparatus may further include a seat ridge.

Some version of the present technology may include an apparatus for delivery of a flow of breathable gas to a patient's airways with a nasal cannula having a set of projections. Each projection may be configured to conduct a flow of gas into a naris of a user. The apparatus may also include a coupler extension configured to couple with one or more gas supply lines of a breathable gas source. The coupler extension may include a seat portion. The seat portion may be configured to receive and seal with a cushion of a respiratory mask. The seat portion may have a sealing bevel to promote sealing between the cushion of the respiratory mask and a facial contact surface of a user.

Optionally, in some versions, the seat portion may include a lumen groove adapted for removably receiving a gas supply line of a breathable gas source. The seat portion may include a triangular profile. The seat portion may include a lentil profile. The apparatus may further include a seat ridge.

Some versions of the present technology may include an apparatus for delivery of a flow of breathable gas to a patient's airways. The apparatus may include a nasal interface having a set of naris pillows. Each naris pillow may be configured to conduct a flow of breathable gas into a naris of a user and form a seal with the naris. Each naris pillow may be further configured with a nasal projection. The nasal projection may be configured to conduct a further flow of gas through the nasal projection. The nasal projection may be configured to extend within the naris beyond the seal of the naris pillow.

Optionally, in some versions, the nasal projection may include a vent for the naris pillow. The nasal projection may include a pillow vent at a surface of the naris pillow. The nasal projection may include a supplemental gas supply conduit. Each naris pillow may be further configured with a further nasal projection such that the further nasal projection may be configured to extend within the naris beyond the seal of the naris pillow. The further nasal projection may further include a vent to atmosphere leading from the naris pillow. The set of naris pillows may include first and second naris pillows. The first and second naris pillow may each include a frusto-cone from which the nasal projection extends.

Optionally, the apparatus may further include a flow generator coupled with the naris pillow. The flow generator may include a controller configured to control a pressure of the flow of breathable gas to the naris pillow.

Optionally, the apparatus may further include a flow generator coupled with the nasal projection. The flow generator may include a controller configured to control a flow rate of the further flow of breathable gas to the nasal projection.

Optionally, the apparatus may include a flow generator coupled with the naris pillow. The flow generator may be further coupled with the nasal projection. The flow generator may have a controller configured to simultaneously control both a flow rate of the further flow of breathable gas to the nasal projection and a pressure of the flow of breathable gas to the naris pillow.

Some versions of the present technology may include an apparatus for delivery of a flow of breathable gas to a patient's airways. The apparatus may include a frame including a plenum chamber. The plenum chamber may be adapted with a connection port for coupling with a delivery conduit. The frame may include at least one flow director within the plenum chamber. The flow director may be configured within the plenum chamber to direct flow at a naris of a user. The flow director may be in fluid communication with a gas supply port on an external side of the plenum chamber.

Optionally, in some versions, the apparatus may further include another flow director within the plenum chamber. The another flow director may be configured within the plenum chamber to direct a gas flow at another naris of the user. Each flow director may be adapted to pivot for adjusting a direction of gas flow from the flow directors. Each flow director may include a tubular conduit. Each flow director may include a directing surface. The directing surface may be adapted as a swivel to change a flow direction attributable to the directing surface.

In some cases, the flow director may include a self-aligning nozzle configured to align dynamically in accordance with inspiratory flow. The flow director may comprises a vane. The flow director may include a ball joint for rotation of the nozzle in response to an inspiratory flow force applied to the vane. The flow director may include a vane extension.

Some versions of the present technology may include apparatus for delivery of a flow of breathable gas to a patient's airways. The apparatus may include a conduit adapted to communicate a flow of gas to a patient respiratory system. The conduit may be formed by a wall material having an exterior surface and an interior surface. The interior surface may include a channel for the flow of gas. The apparatus may include a slit valve formed by a portion of the wall material of the conduit. The portion of the wall material may include part of the exterior surface and part of the interior surface. The portion may be movable to open the channel to atmosphere in response to a pressure condition of the channel.

The slit valve may be configured to deform outwardly relative to the channel to permit gas flow from the channel to atmosphere in response to an over pressure condition in the channel. The slit valve may be configured to deform inwardly relative to the channel to permit gas flow into the channel from atmosphere in response to an under pressure condition in the channel. In some cases, the slit valve may be a bi-directional valve. In some cases, the slit valve may be a unidirectional valve.

The moveable portion of the wall material may include a first slit and a second slit, where in a cross sectional plane of the conduit, an imaginary axis of a first slit and an imaginary axis of the second slit form an angle with a non-central vertex of the angle inside of the channel. The slit valve may be configured to deform outwardly relative to the channel to permit gas flow from the channel to atmosphere in response to an over pressure condition in the channel.

The moveable portion of the wall material may include a first slit and a second slit, where in a cross sectional plane of the conduit, an imaginary axis of a first slit and an imaginary axis of the second slit form an angle with a vertex of the angle outside of the channel. The slit valve may be configured to deform inwardly relative to the channel to permit gas flow into the channel from atmosphere in response to an under pressure condition in the channel.

The moveable portion may include a bend region along an axis that is parallel to a length of the conduit. The moveable portion may include a bend region along an arc of the exterior surface of the conduit.

Optionally, the conduit may be or include a tube. The conduit may further include a cannula. In some cases, the conduit may also include a coupler sheathe. The coupler sheathe may be configured for removable engagement with a portion of the exterior surface of the conduit to selectively cover one or more slit valves of the conduit.

Some versions of the present technology may include apparatus for delivery of a flow of breathable gas to a patient's airways. The apparatus may include a nare vent adapted to permit an exhaust flow of expired breathable gas from a respiratory system of a patient. The nare vent may be configured to seal about an internal periphery of a nare of the patient so as to provide a known gas flow characteristic of the exhaust flow. The nare vent may be adapted to receive a prong of a nasal cannula for providing a breathable gas to the respiratory system of the patient. In some cases, the known gas flow characteristic may be a known impedance. The nare vent may include a holder for removable engagement of the prong of the nasal cannula. The nare vent may include an integrated prong of the nasal cannula. The nare vent may be a ring.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receives a supply of air at positive pressure from a PAP device 4000. Air from the PAP device is humidified in a humidifier 5000, and passes along an air circuit 4170 to the patient 1000. A bed partner 1100 is also shown.

4.2 Therapy 4.2.1 Respiratory System

Figure 1A:
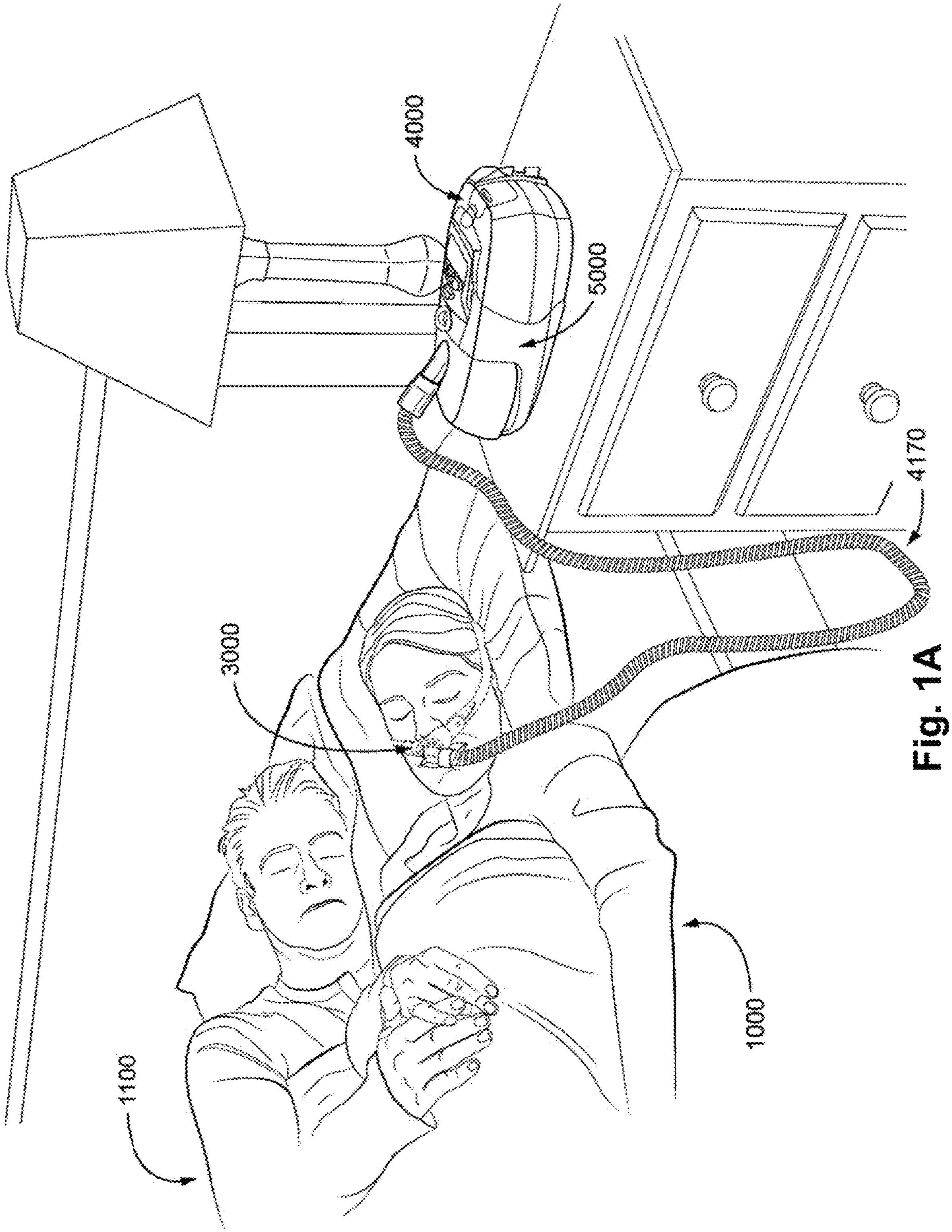
FIG. 1B shows a system including a patient 1000 wearing a patient interface 3000, in the form of a nasal mask, receives a supply of air at positive pressure from a PAP device 4000. Air from the PAP device is humidified in a humidifier 5000, and passes along an air circuit 4170 to the patient 1000.
FIG. 1C shows a system including a patient 1000 wearing a patient interface 3000, in the form of a full-face mask, receives a supply of air at positive pressure from a PAP device 4000. Air from the PAP device is humidified in a humidifier 5000, and passes along an air circuit 4170 to the patient 1000.
Figure 1B:
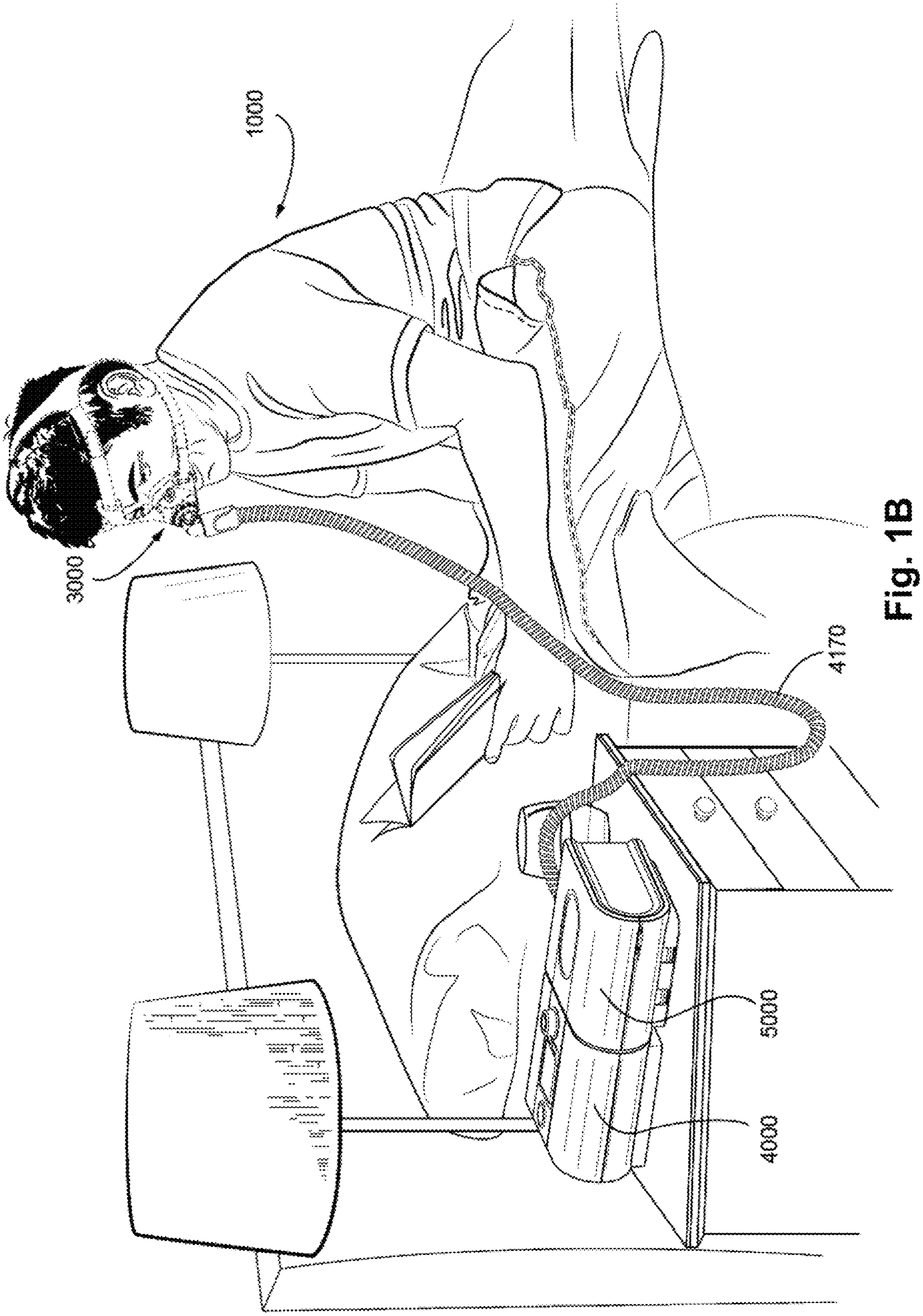
Figure 1C:
Figure 2A:
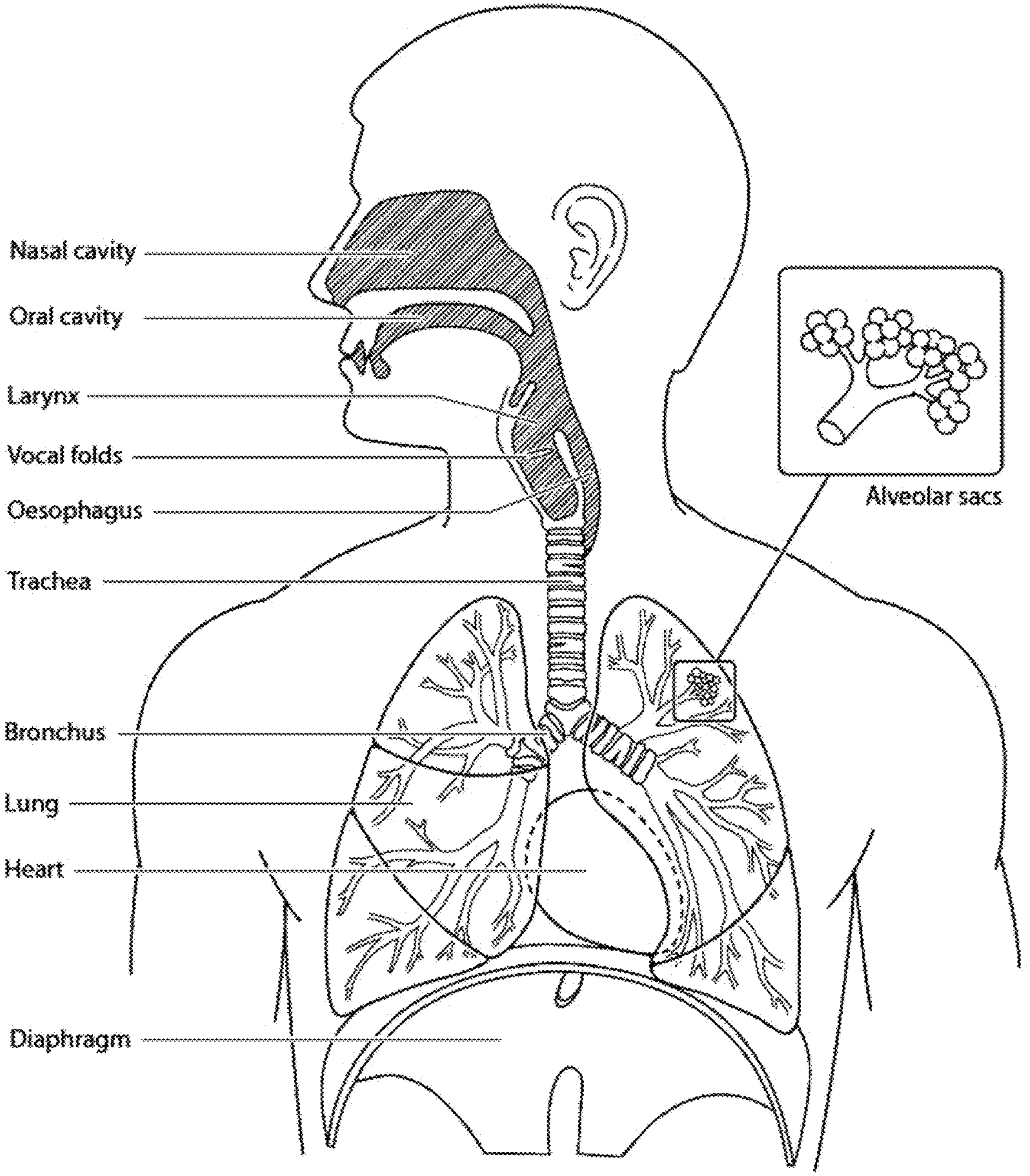

FIG. 2A shows an overview of a human respiratory system including the nasal and oral cavities, the larynx, vocal folds, oesophagus, trachea, bronchus, lung, alveolar sacs, heart and diaphragm.

Figure 2B:
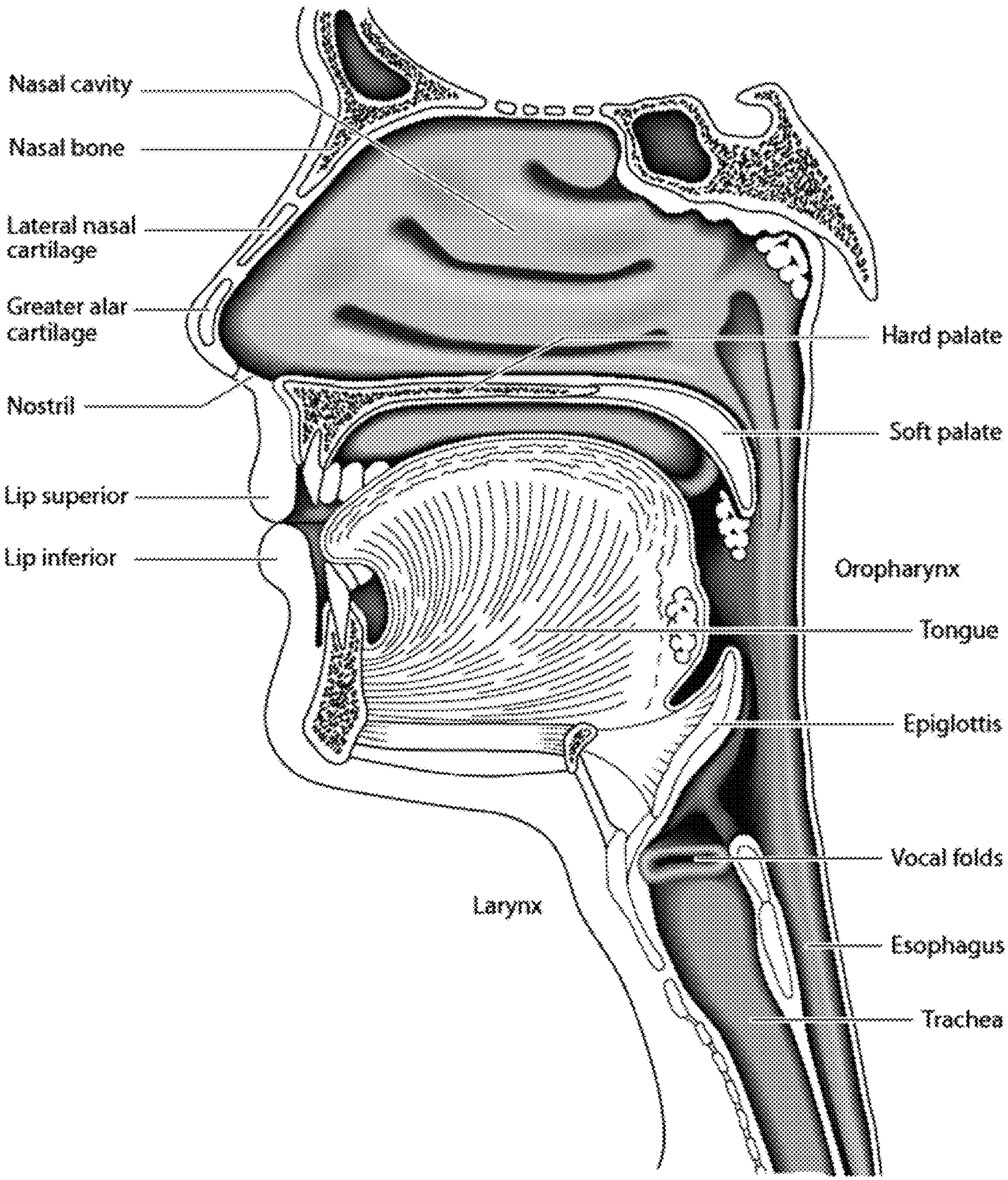

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

4.2.2 Facial Anatomy

Figure 2C:
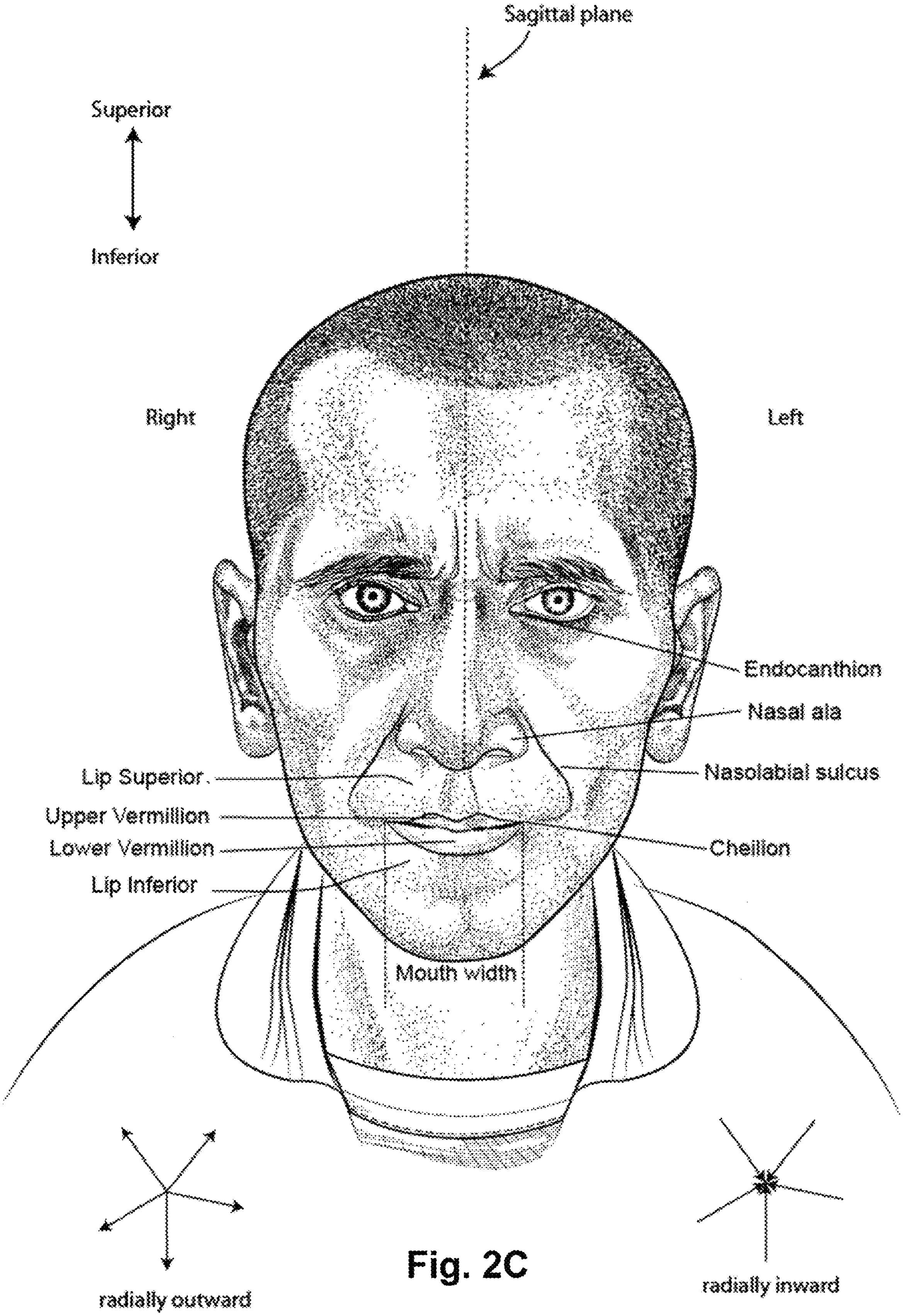

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
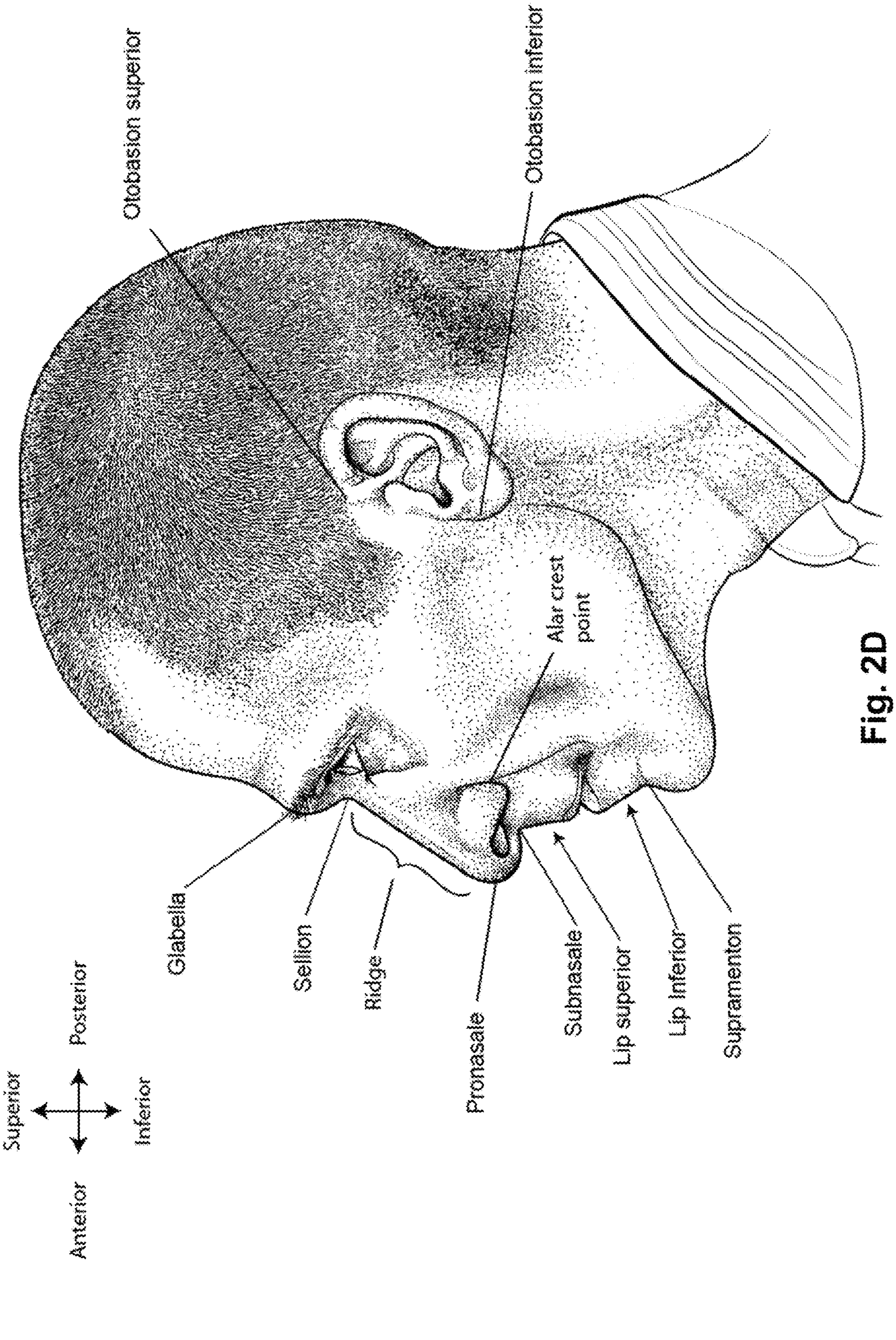

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
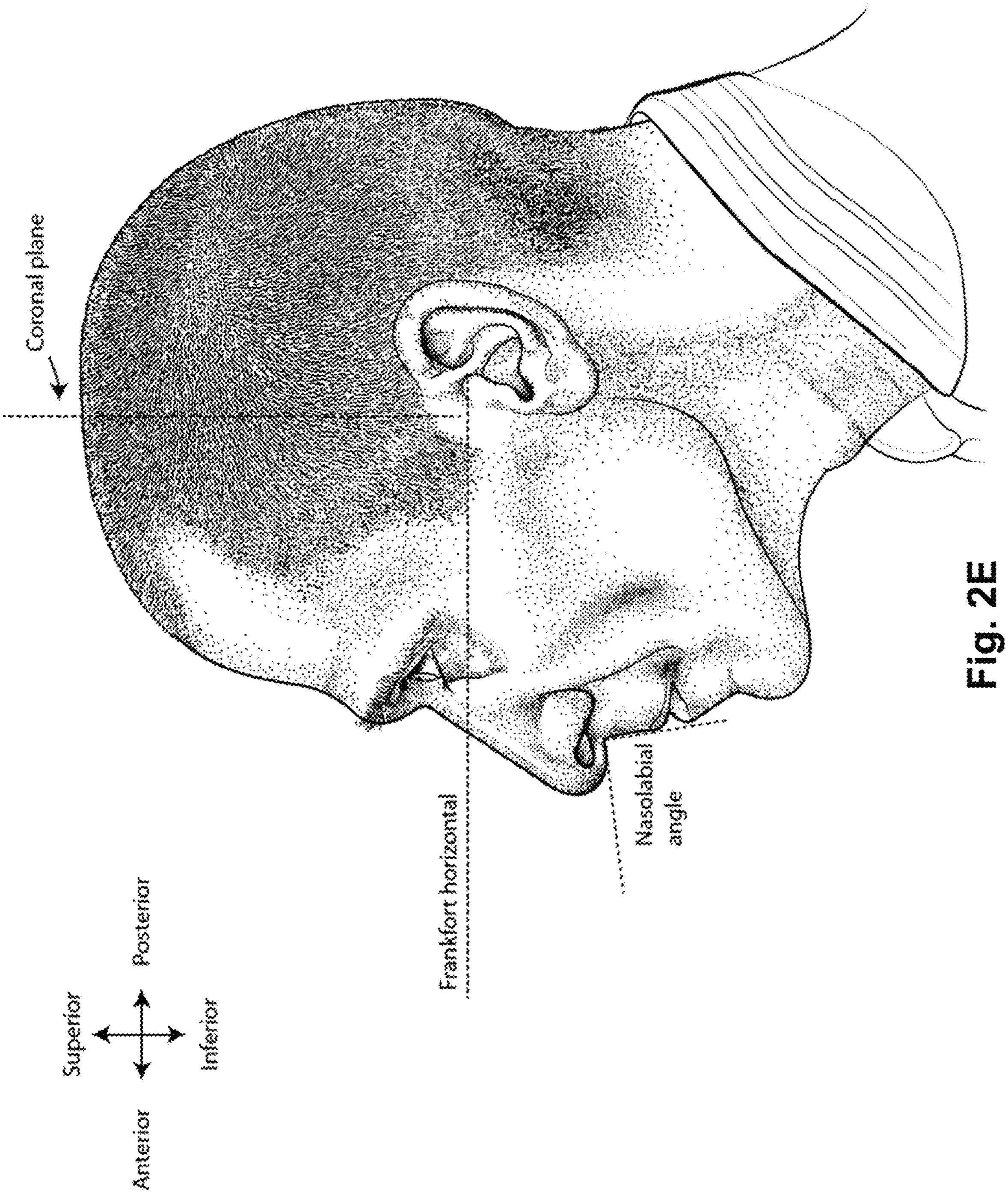

FIG. 2E is a further side view of a head. The approximate locations of the Frankfort horizontal and nasolabial angle are indicated. The coronal plane is also indicated.

Figure 2F:
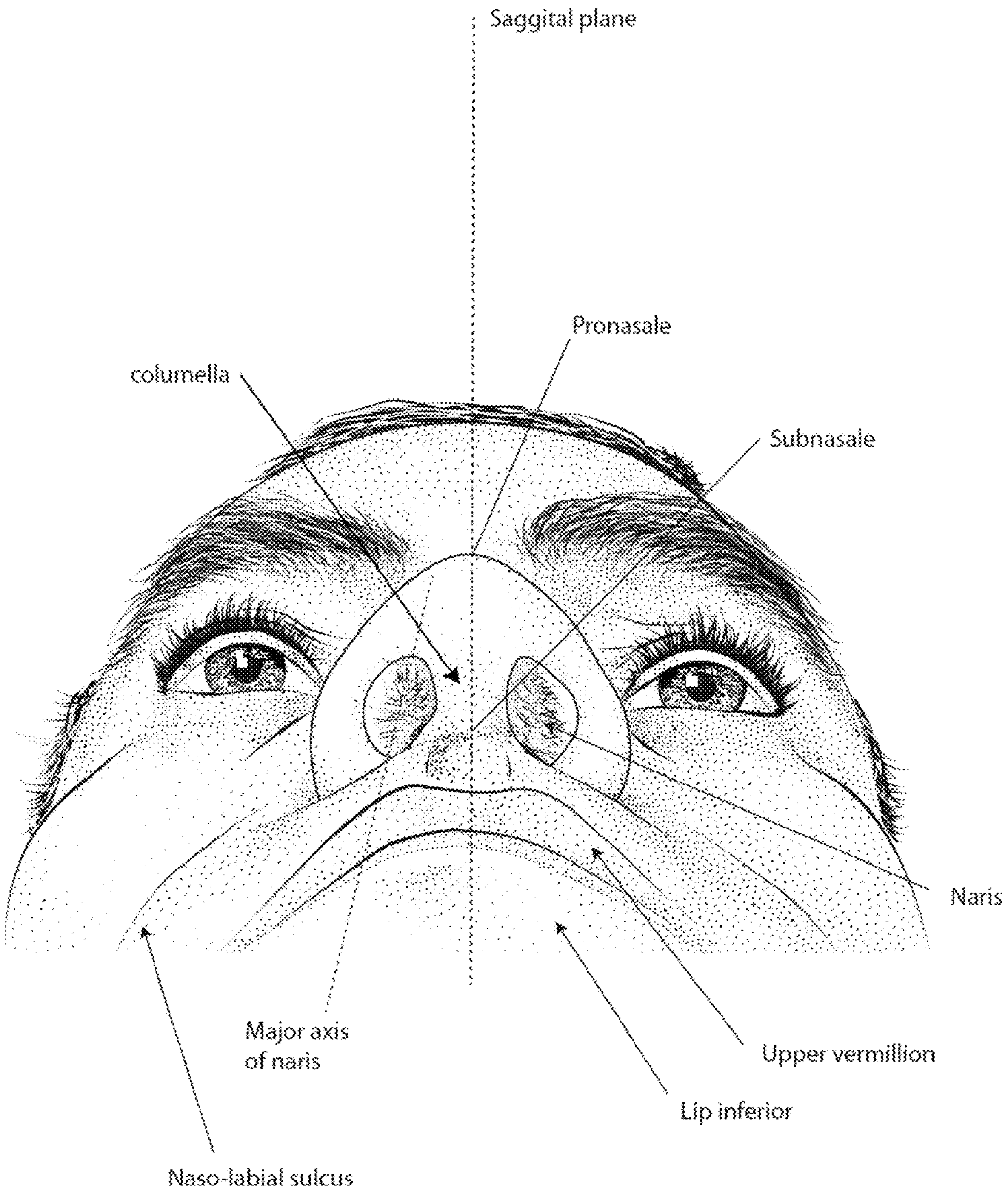

FIG. 2F shows a base view of a nose with several features identified including naso-labial sulcus, lip inferior, upper Vermilion, naris, subnasale, columella, pronasale, the major axis of a naris and the sagittal plane.

4.3 Patient Interface

Figure 3A:
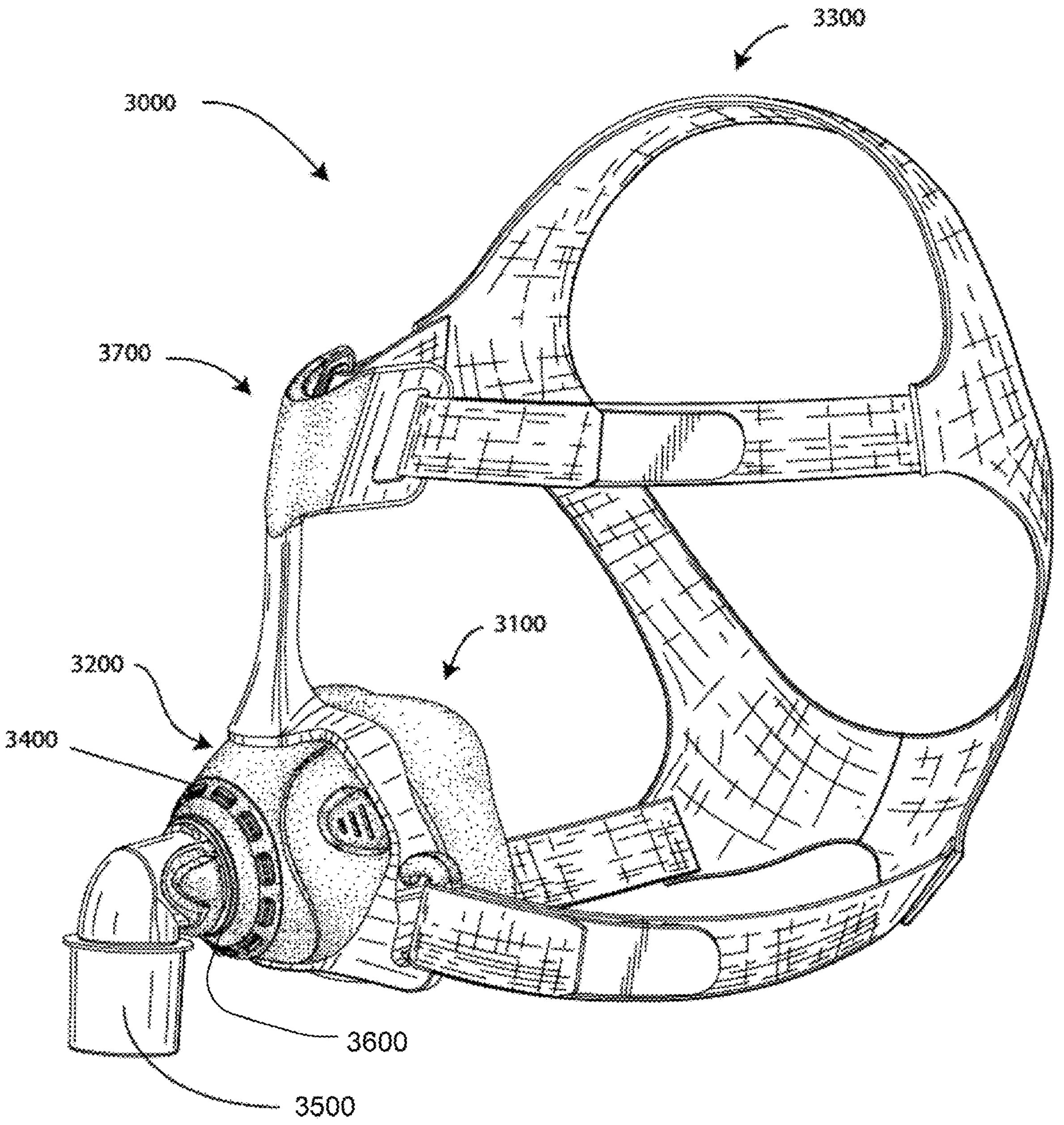

FIG. 3A shows a patient interface in the form of a nasal mask in accordance with one form of the present technology.

4.4 PAP Device

Figure 4A:
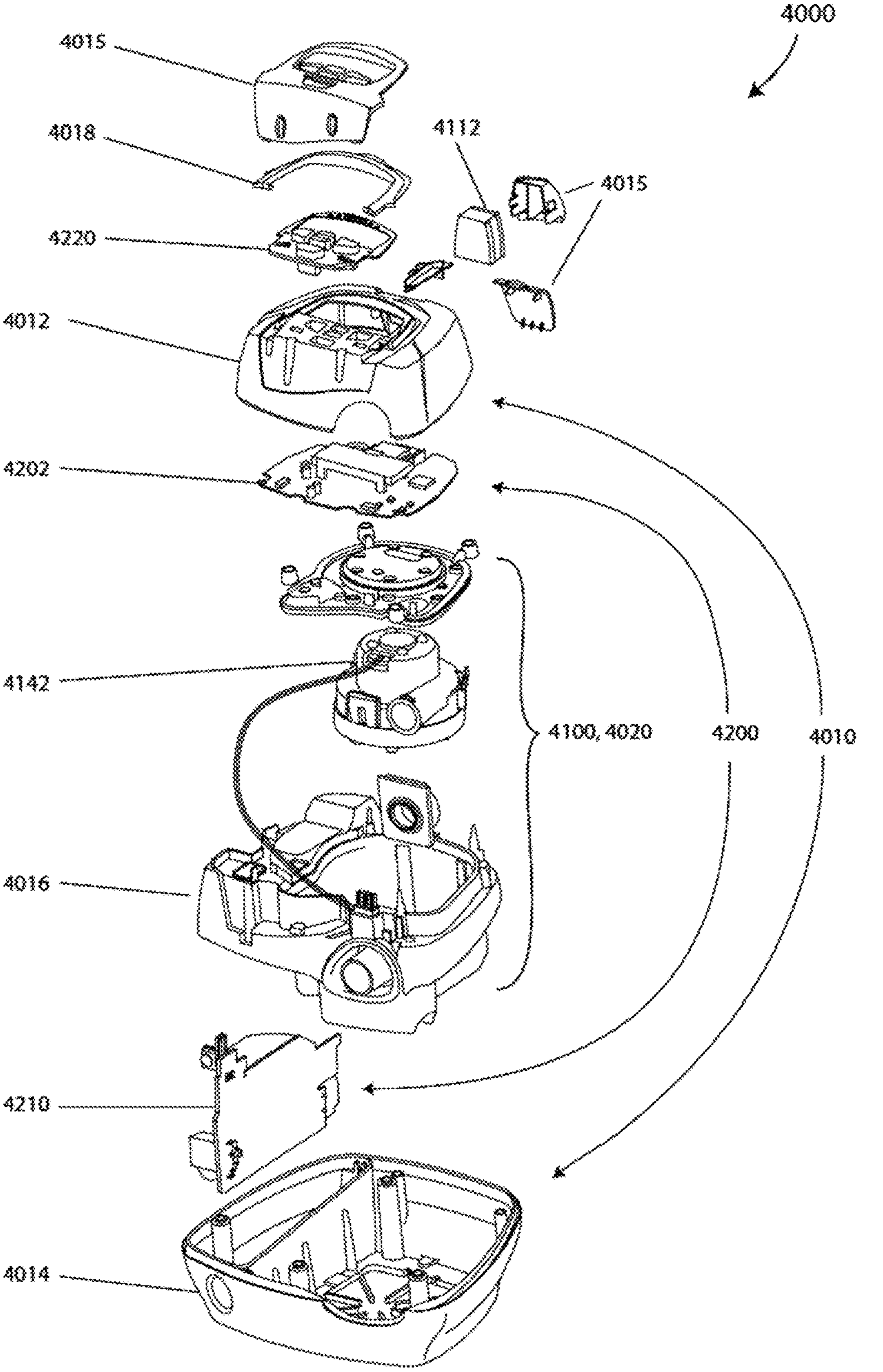

FIG. 4A shows a PAP device in accordance with one form of the present technology.

Figure 4B:
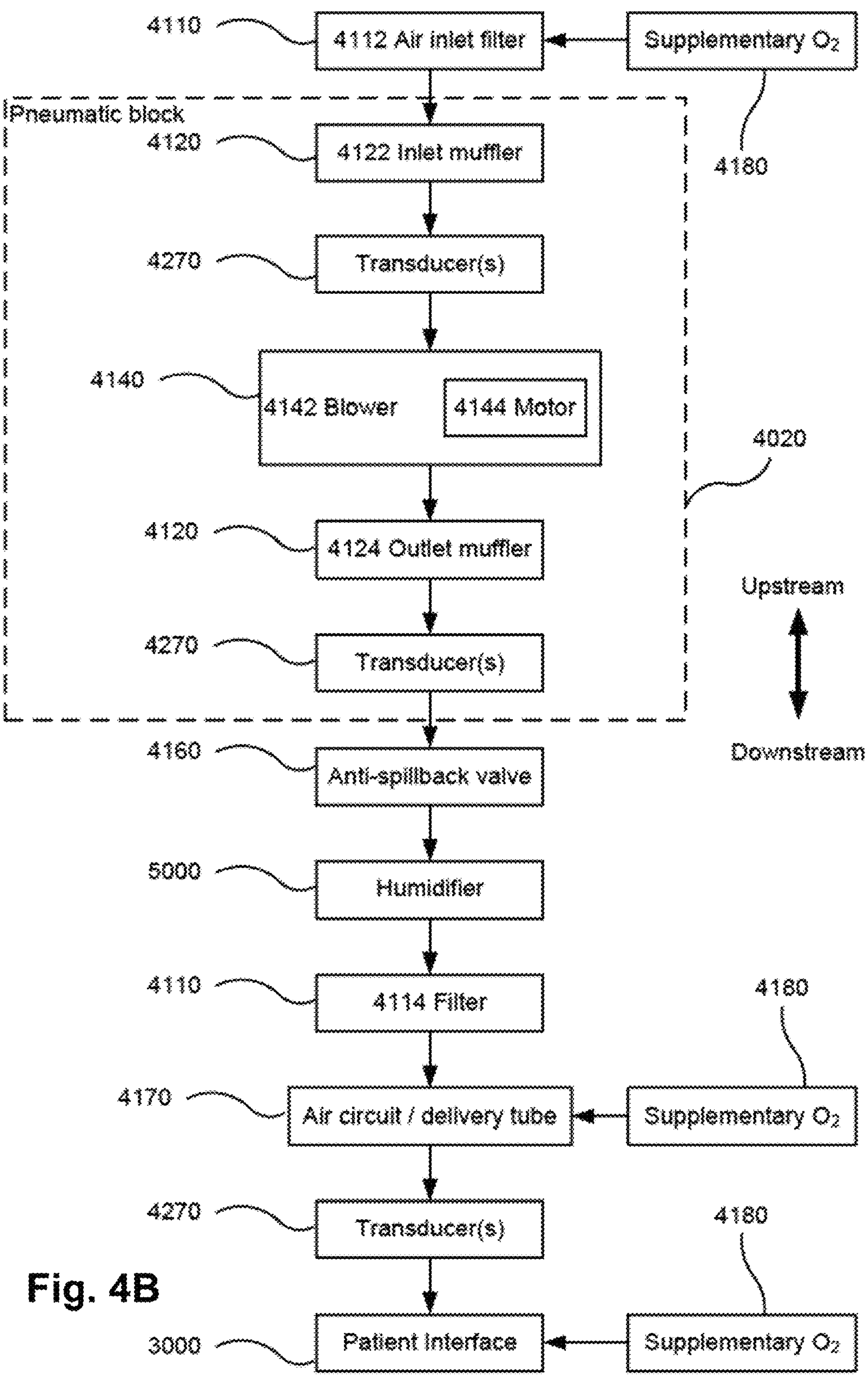

FIG. 4B shows a schematic diagram of the pneumatic circuit of a PAP device in accordance with one form of the present technology. The directions of upstream and downstream are indicated.

Figure 4C:
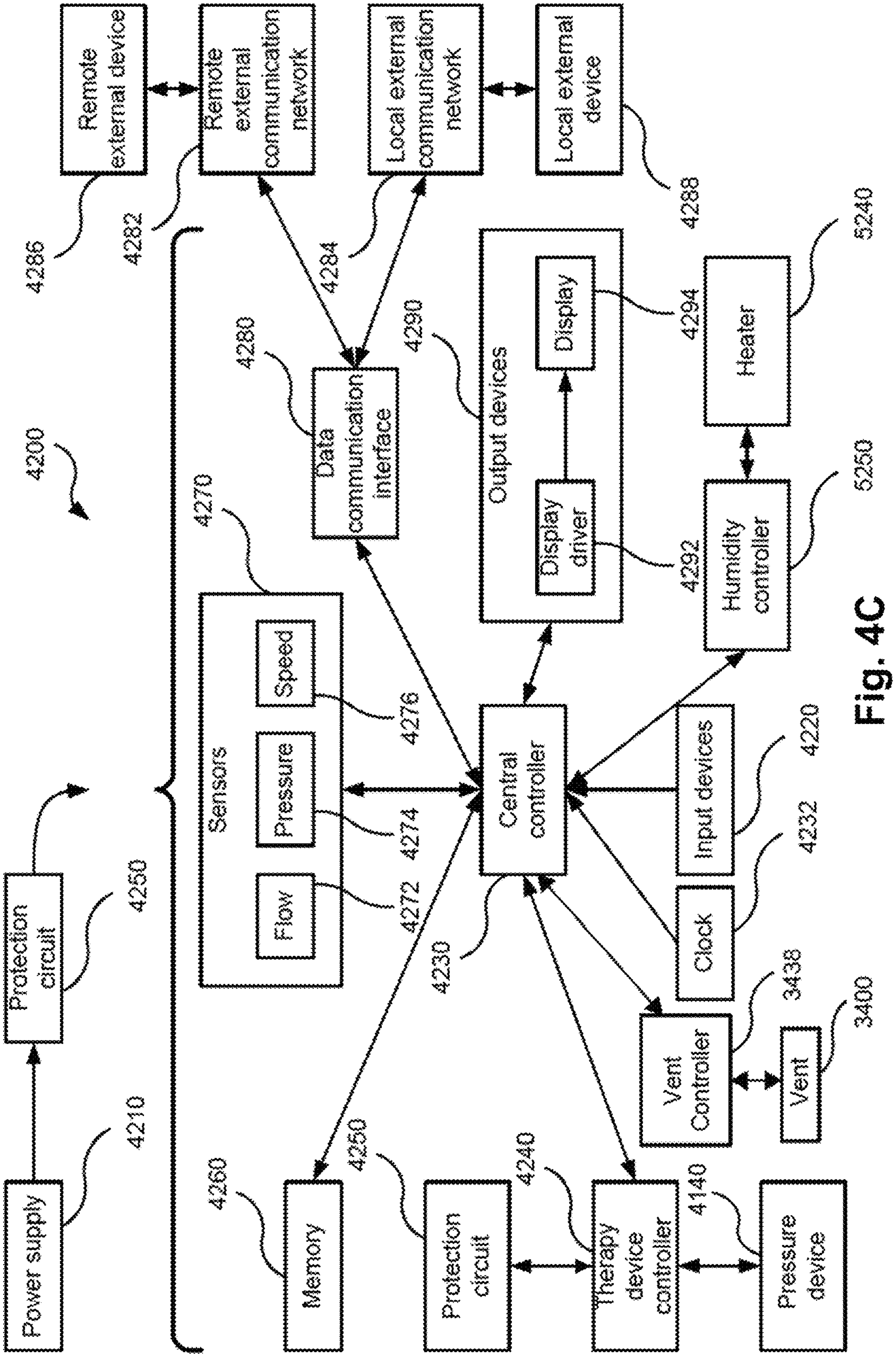

FIG. 4C shows a schematic diagram of the electrical components of a PAP device in accordance with one aspect of the present technology.

4.5 Humidifier

Figure 5A:
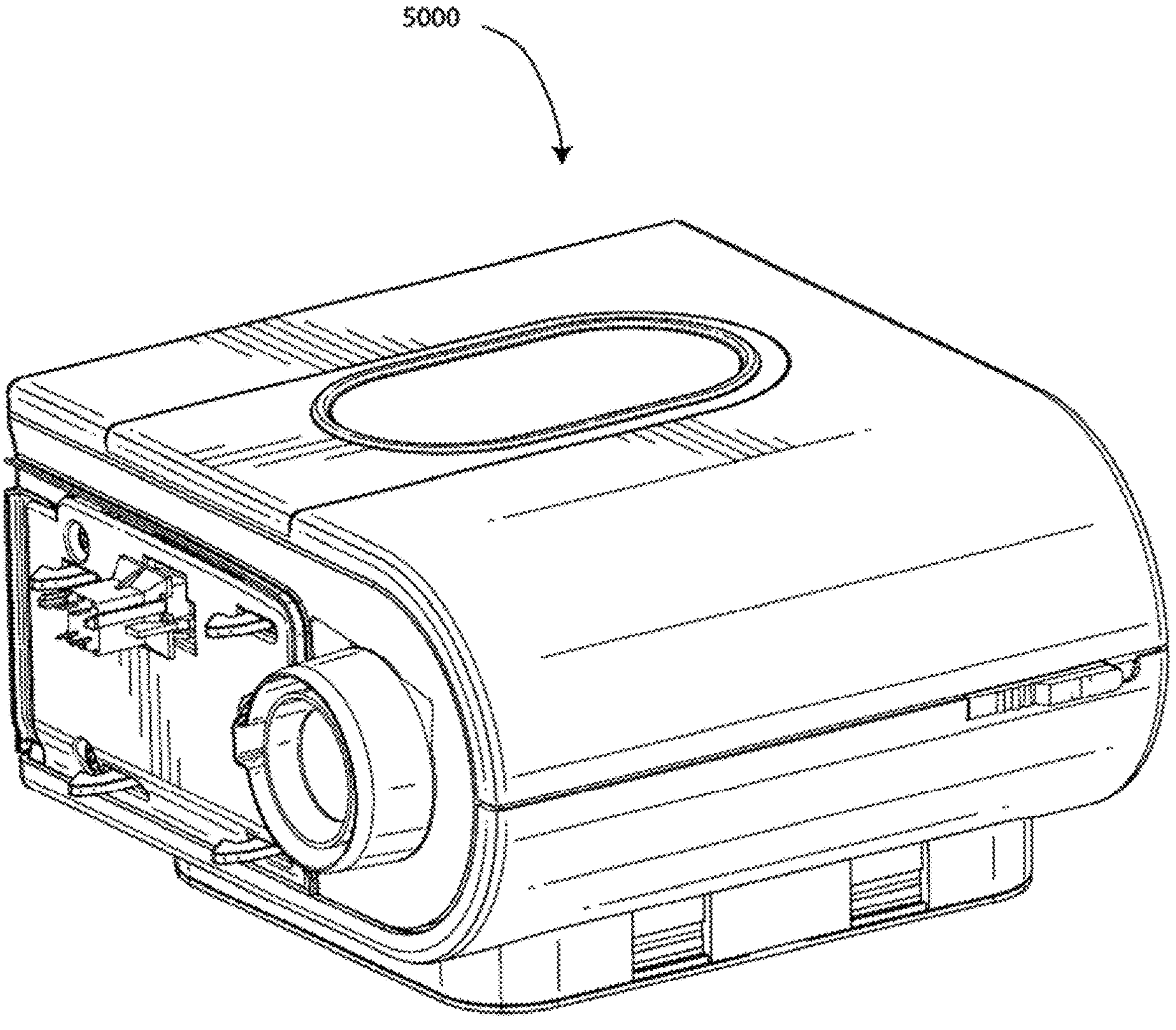

FIG. 5A shows an isometric view of a humidifier suitable for use with a respiratory apparatus.

4.6 Additional Patient Interface for Optional Therapies

Figure 6:
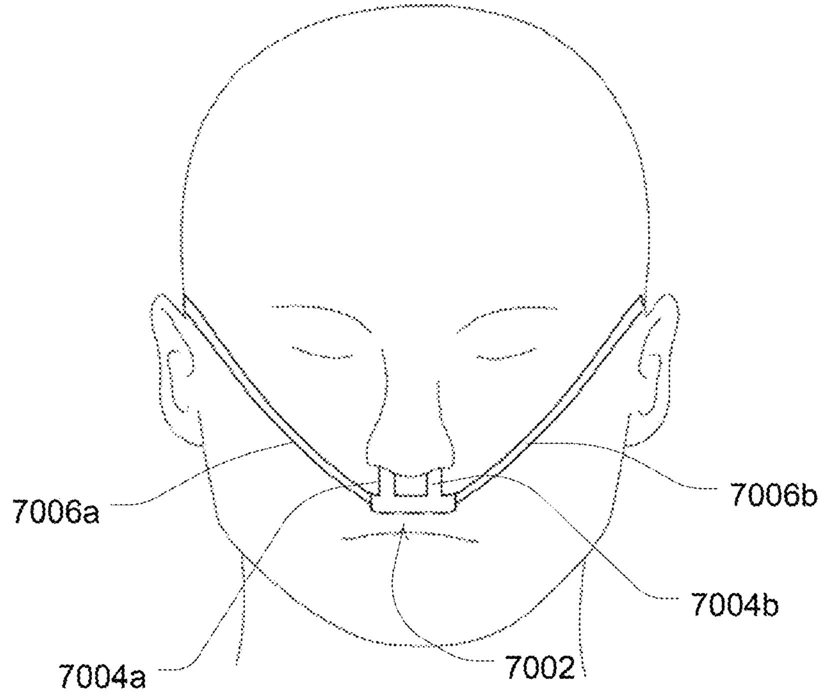
Figure 7:
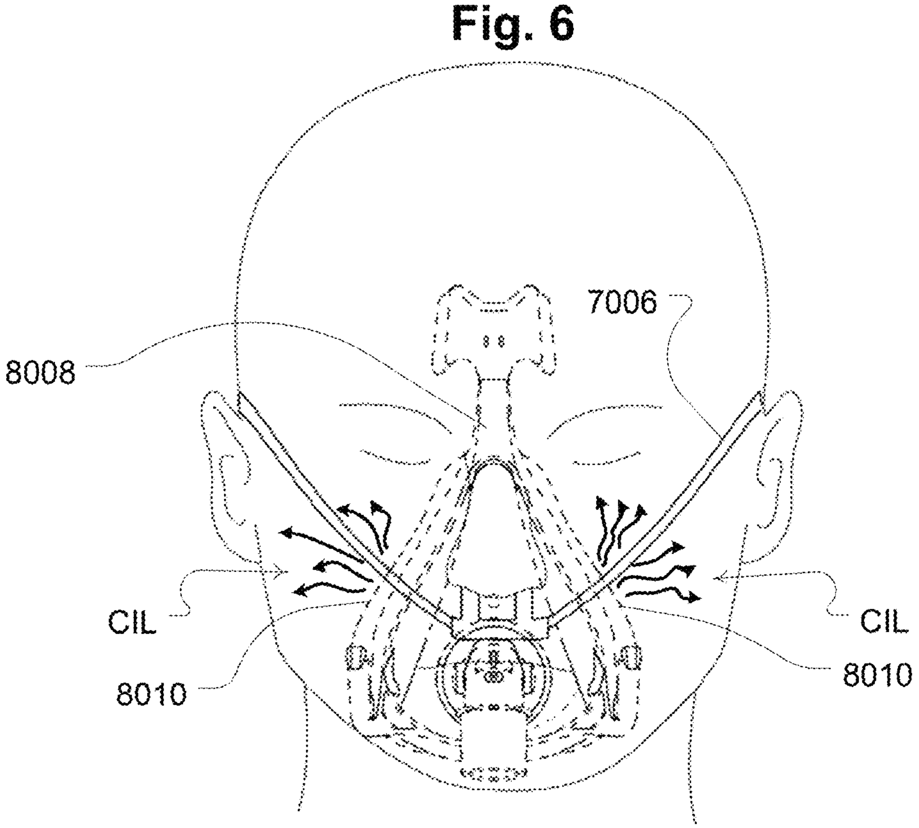
Figure 8:
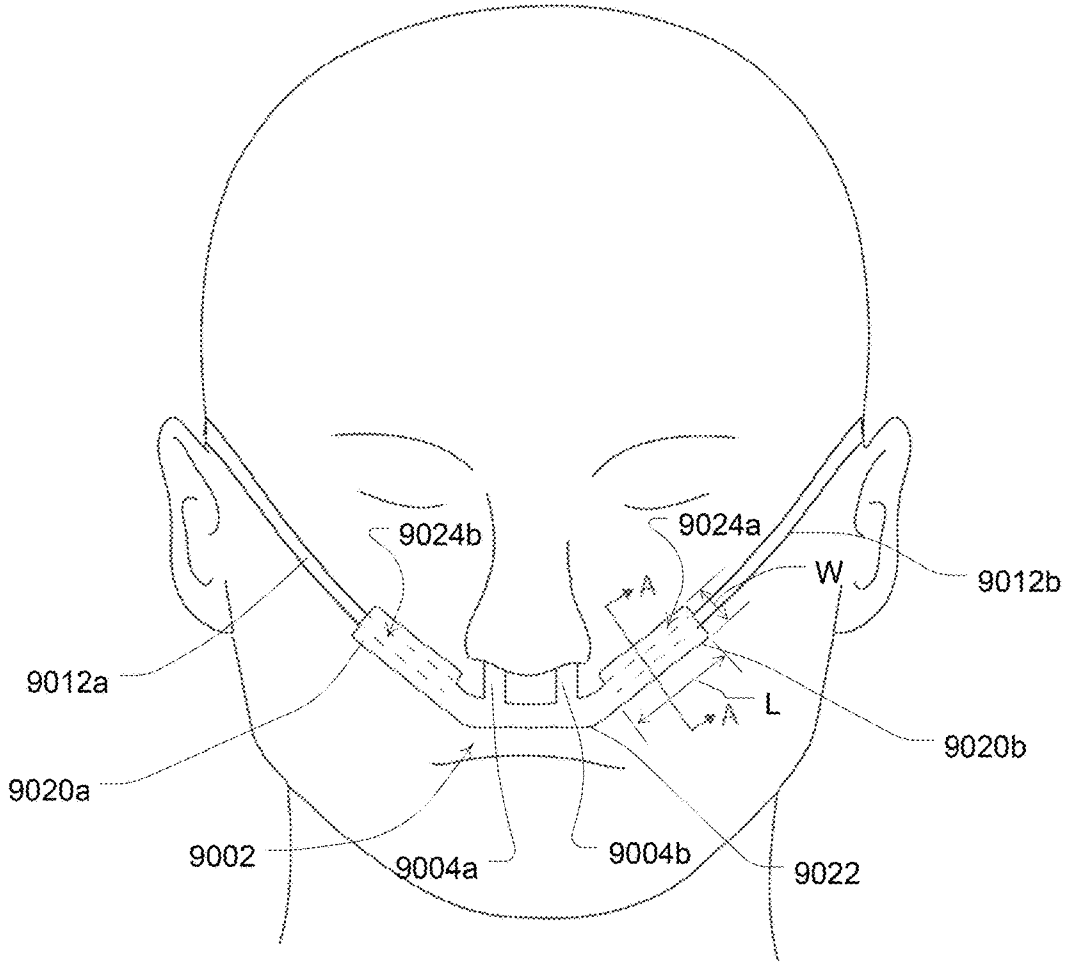
Figure 10A:
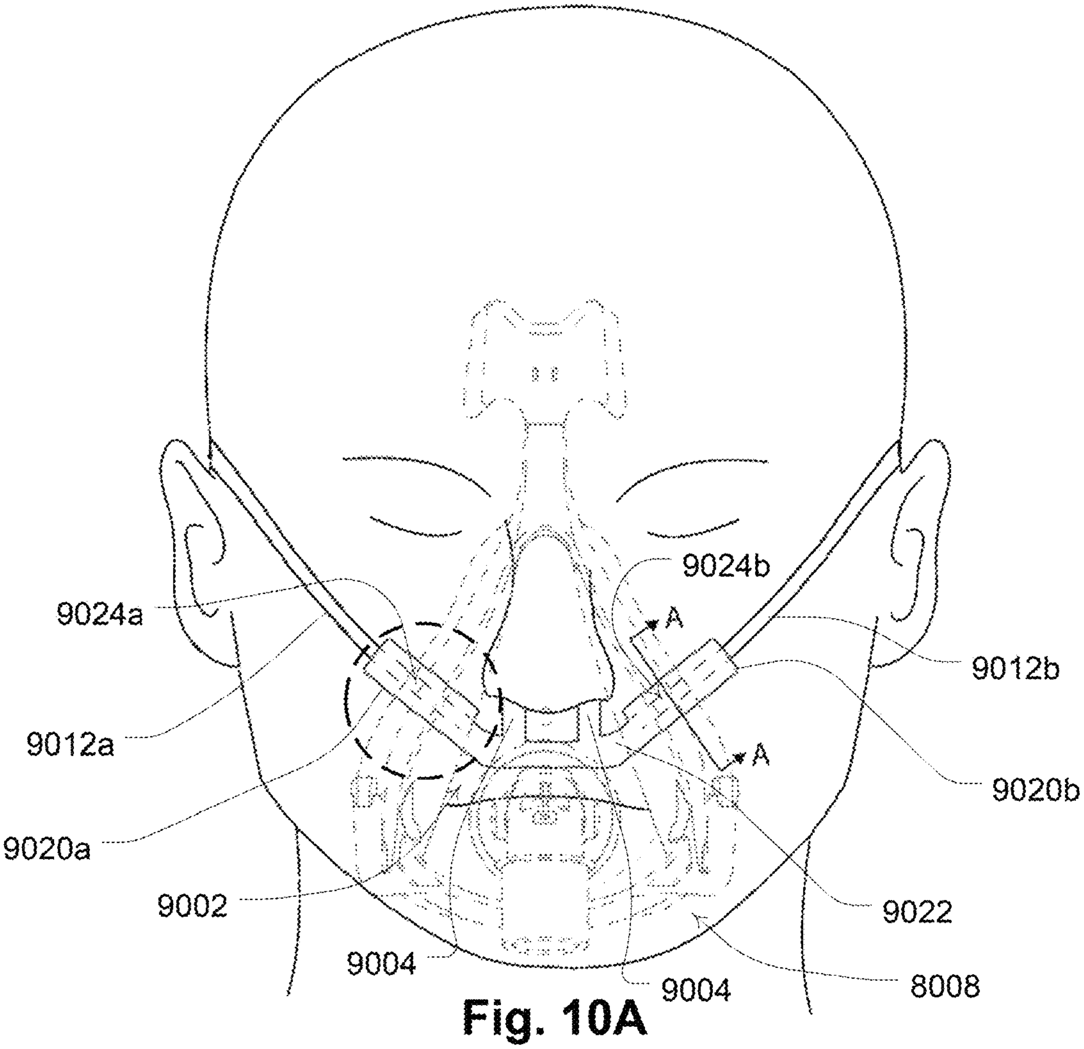
Figure 10B:
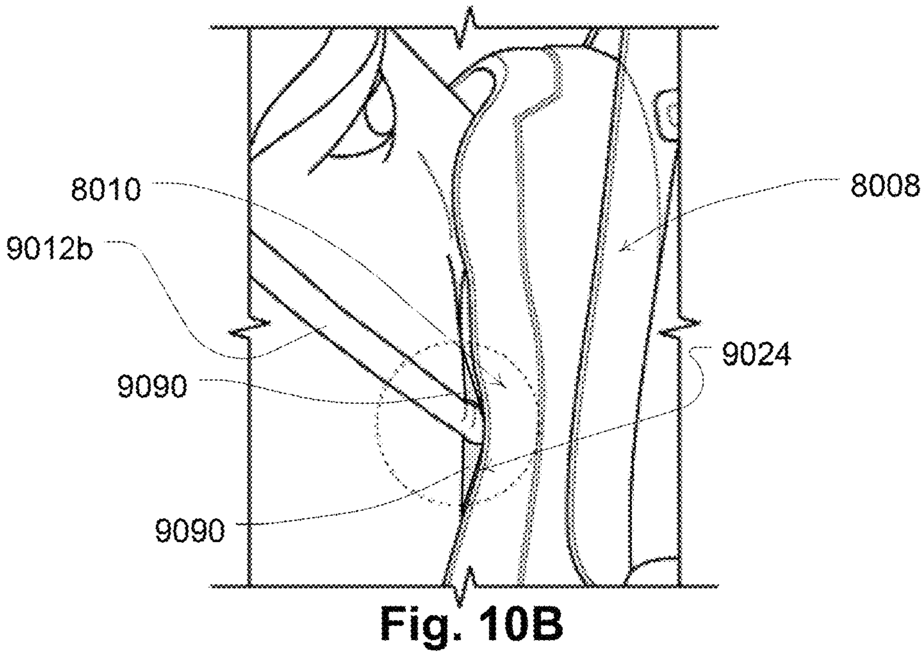
Figure 11:
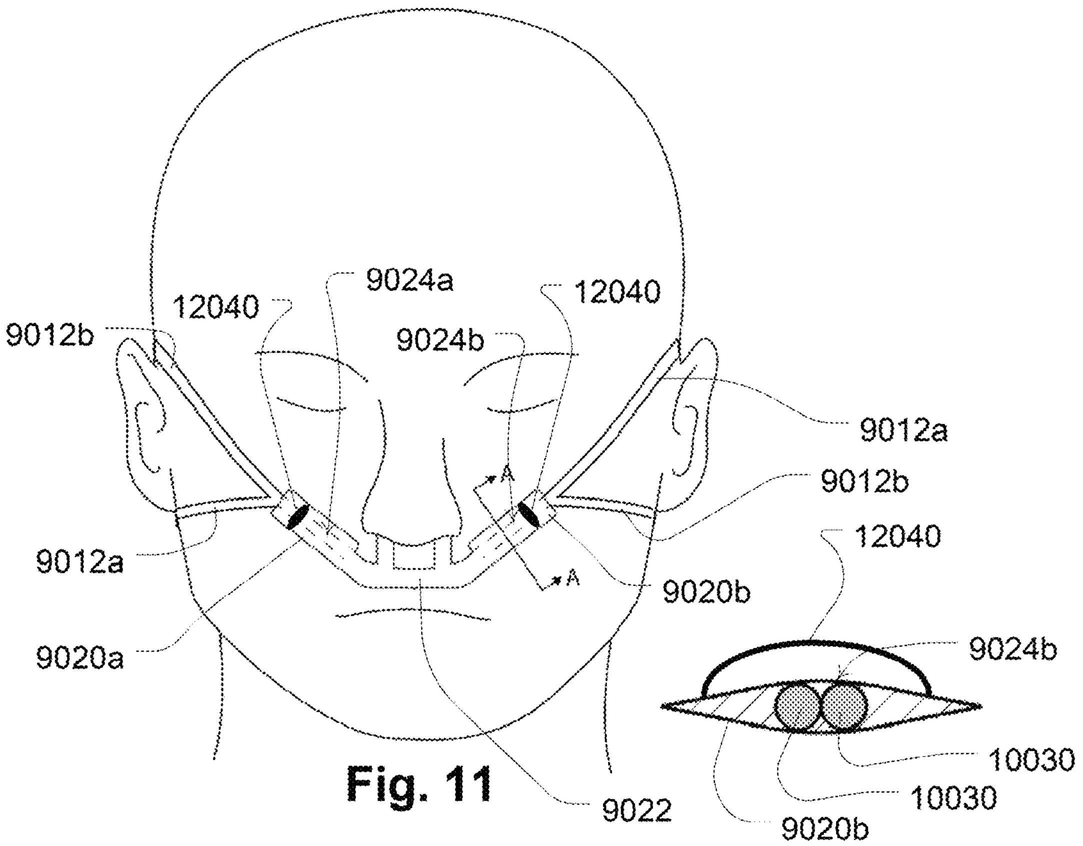
Figure 12:
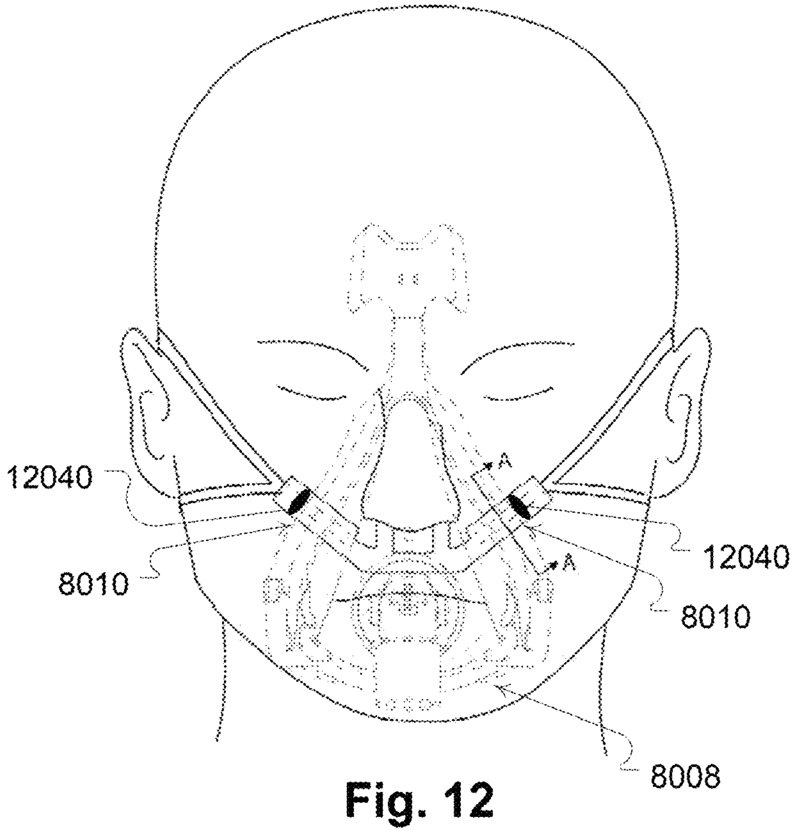
Figure 13:
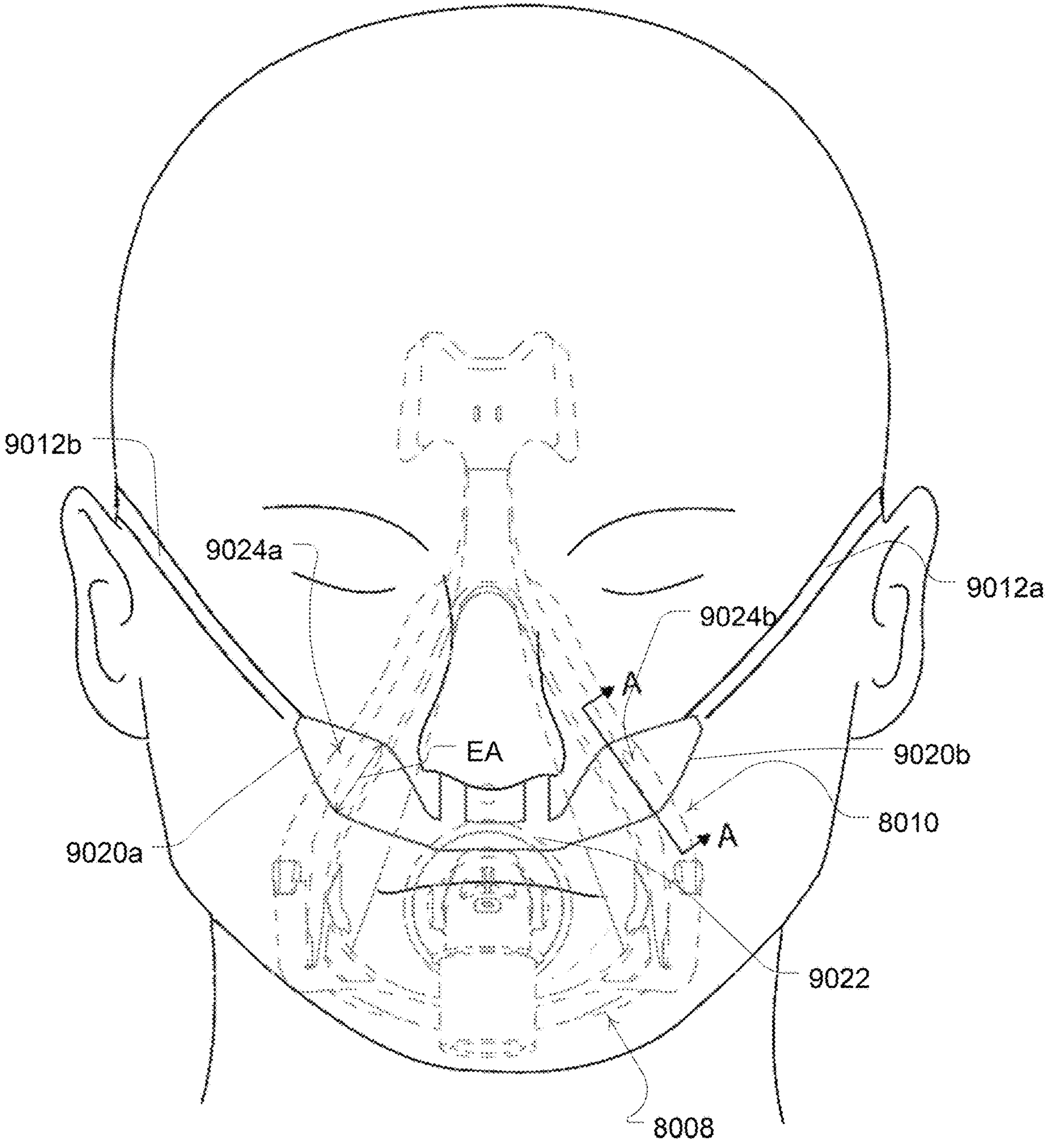
Figure 14A:
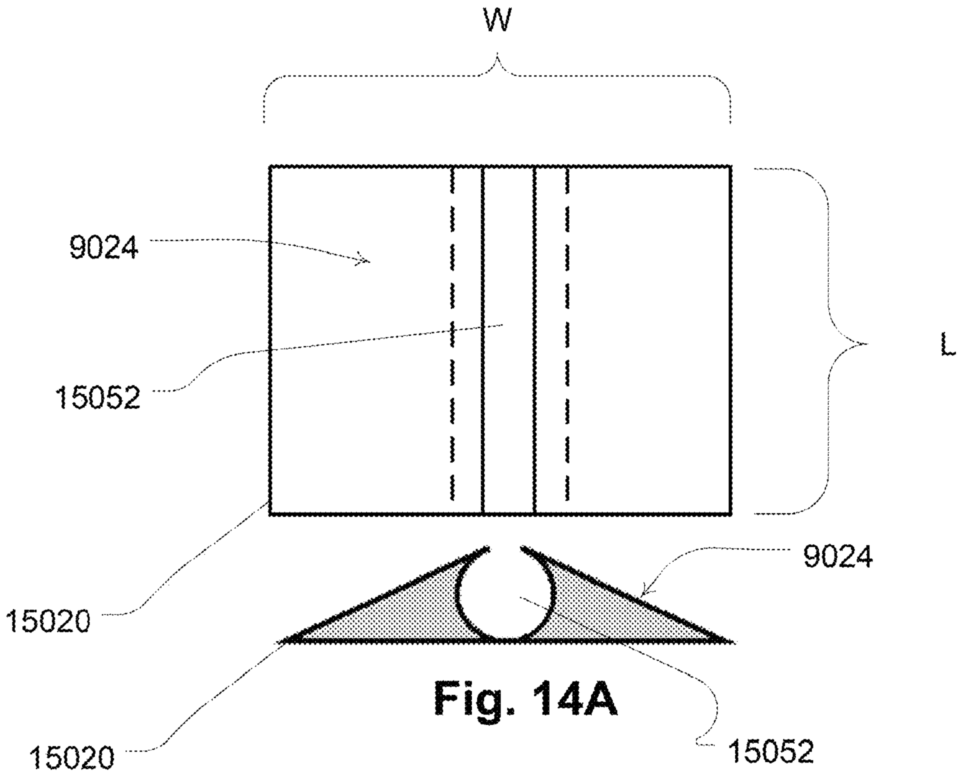
Figure 14B:
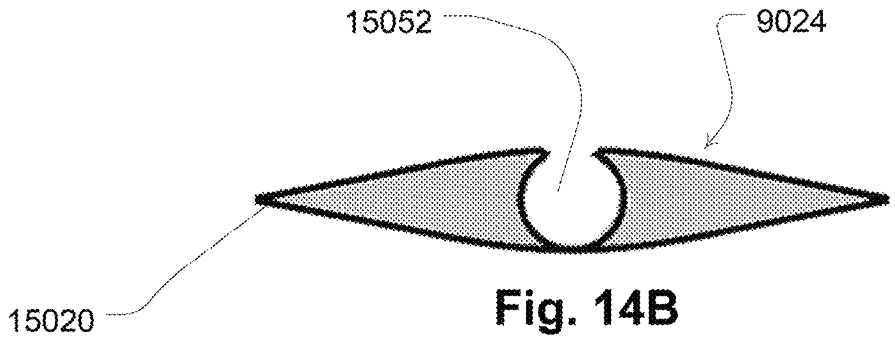
Figure 14C:
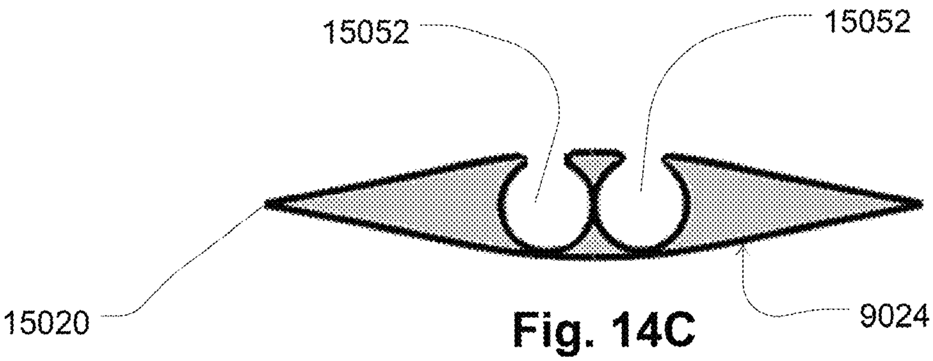
Figure 15A:
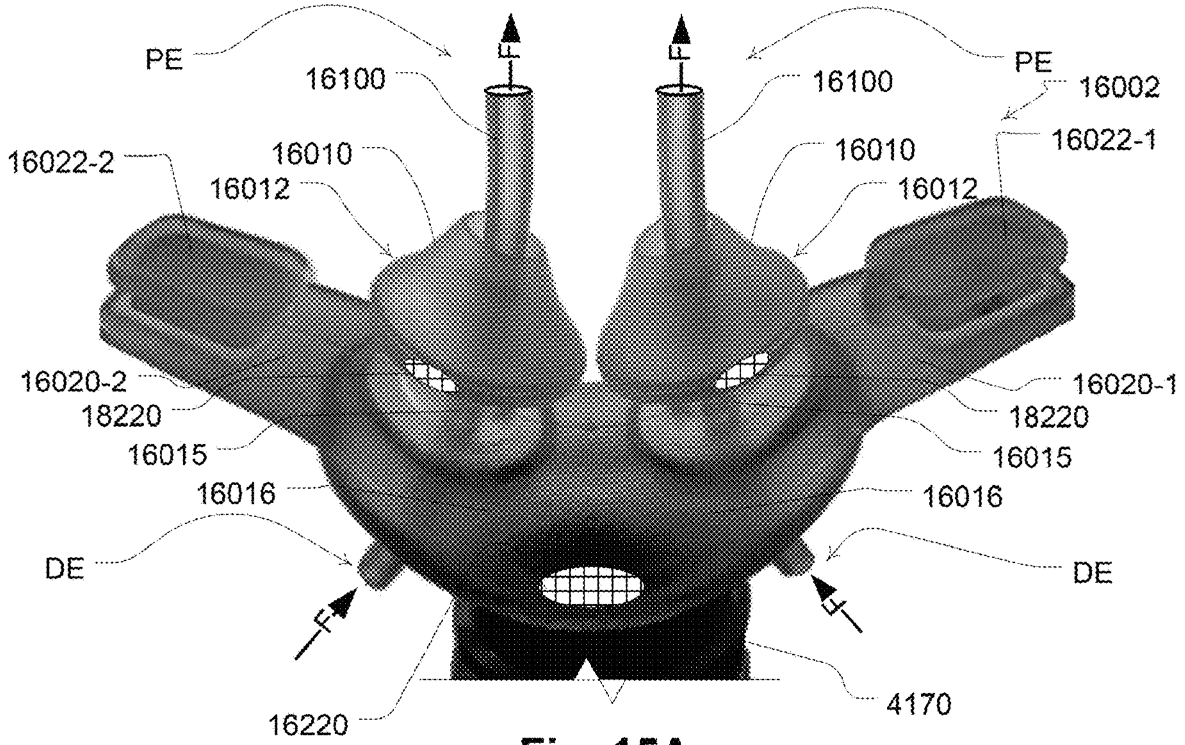
Figure 15B:
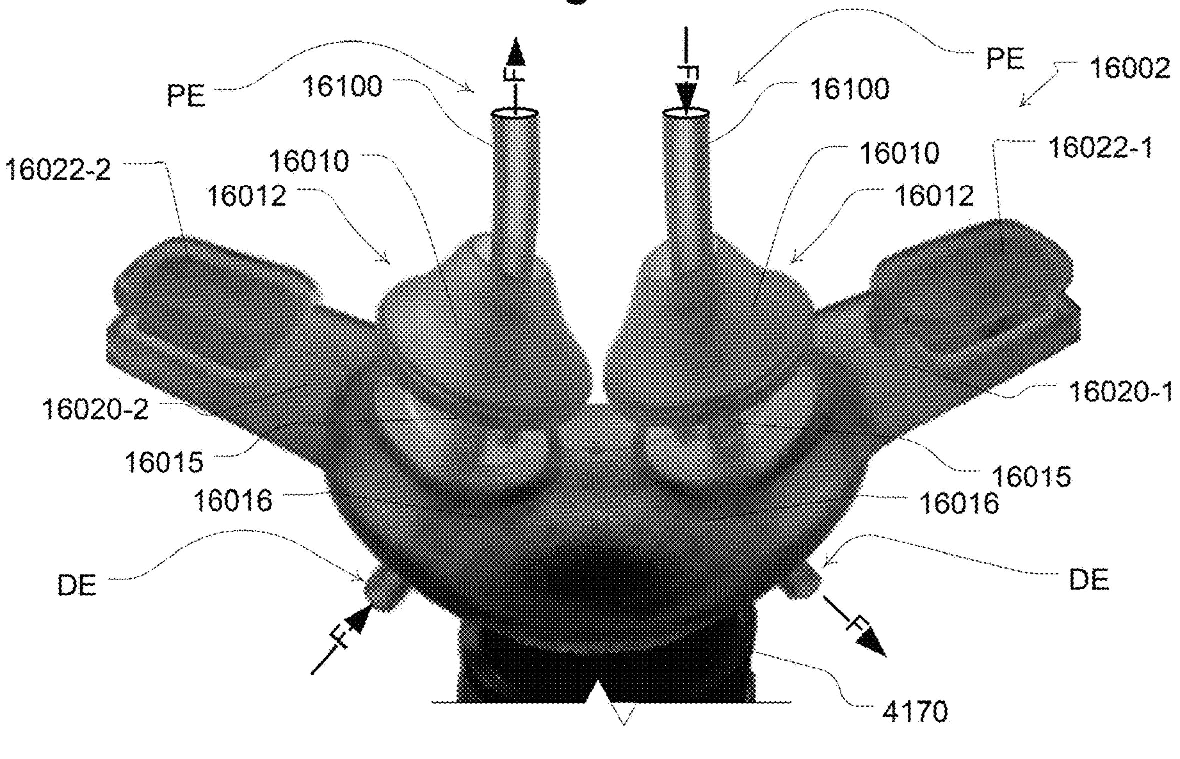
Figure 16:
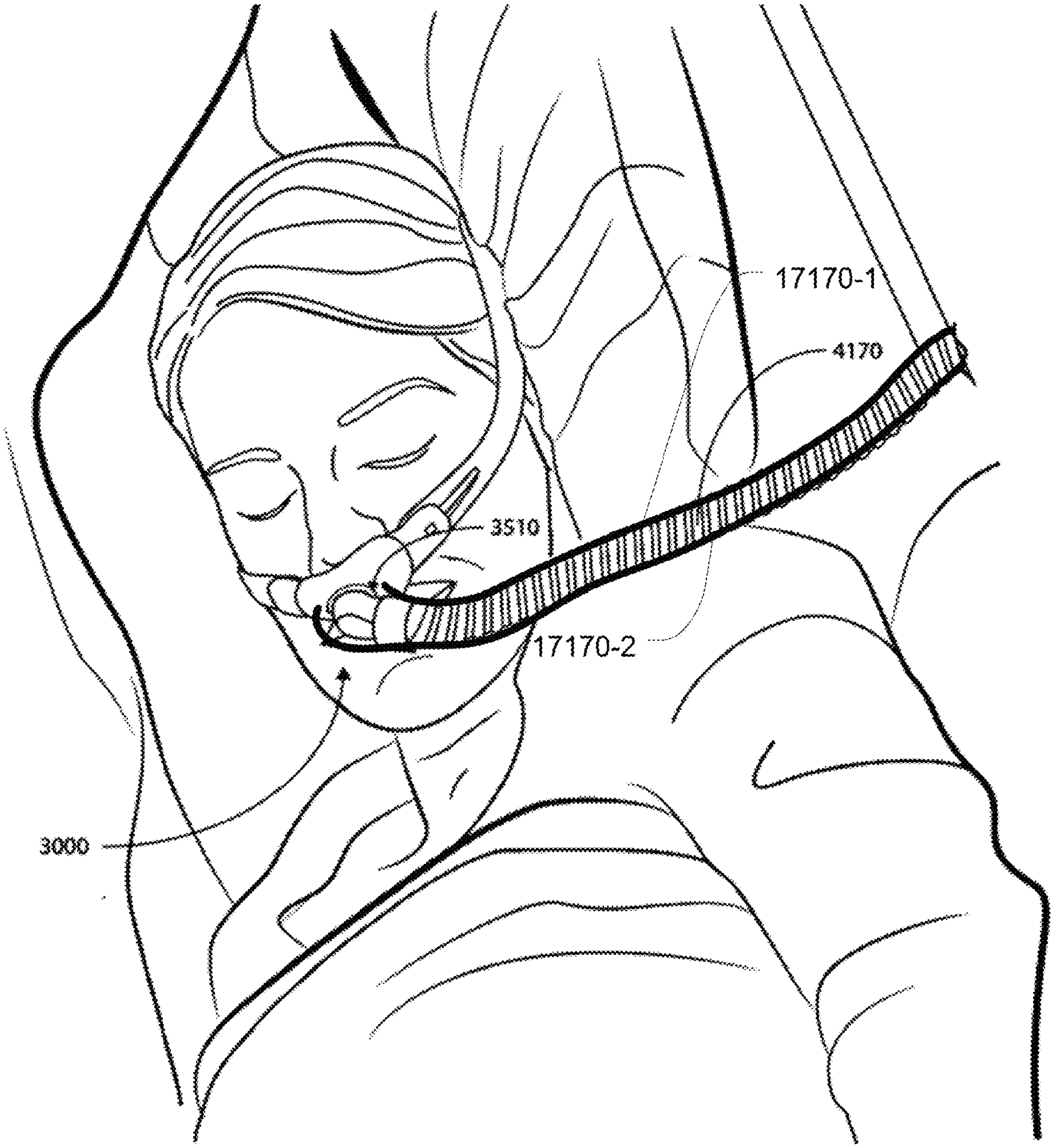
Figure 17A:
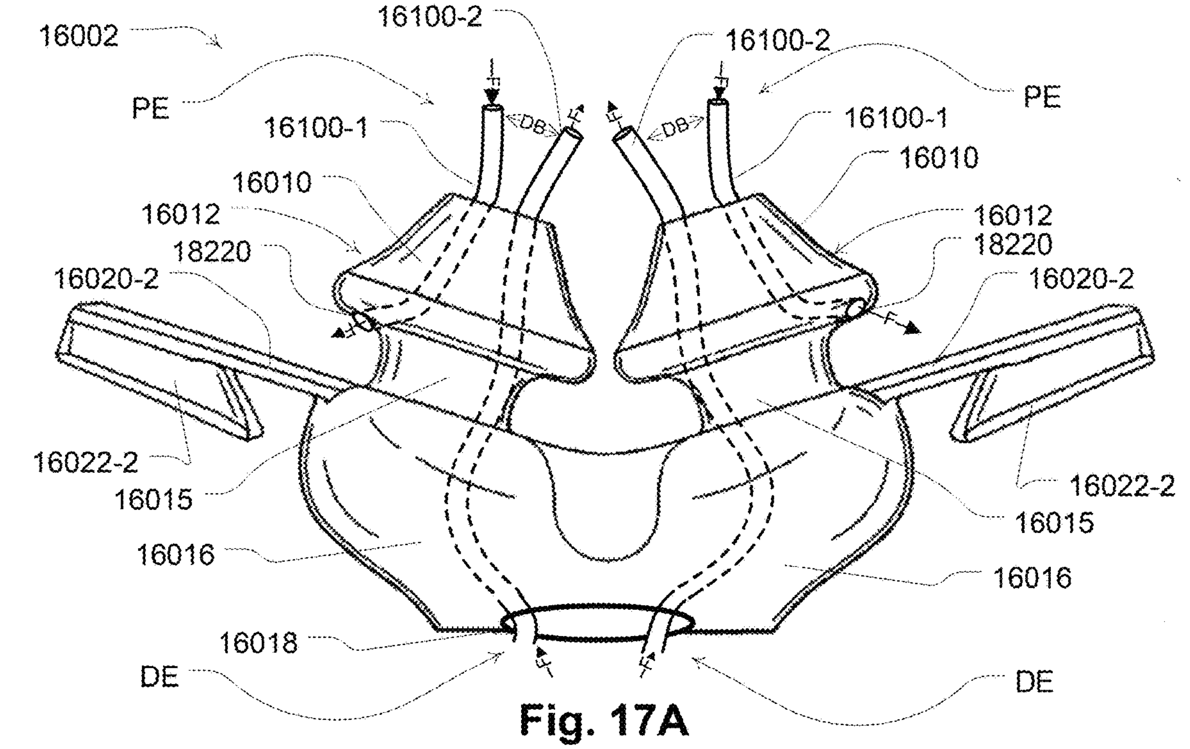
Figure 17B:
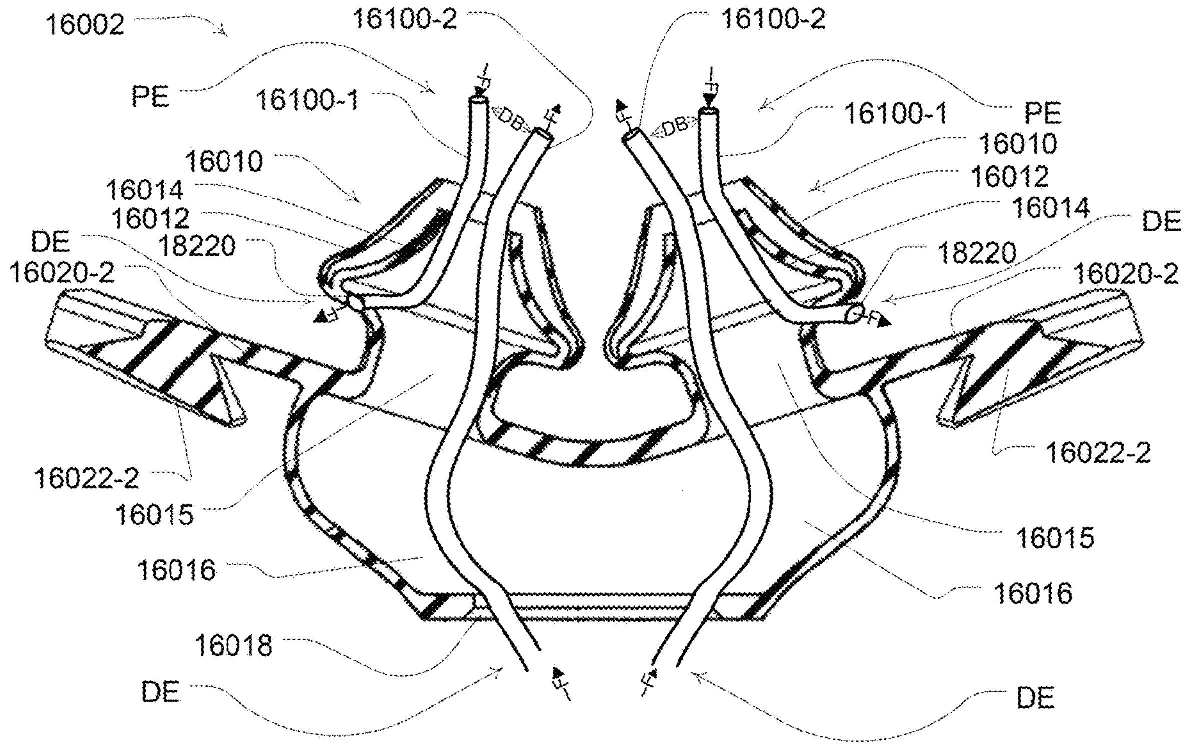
Figure 18:
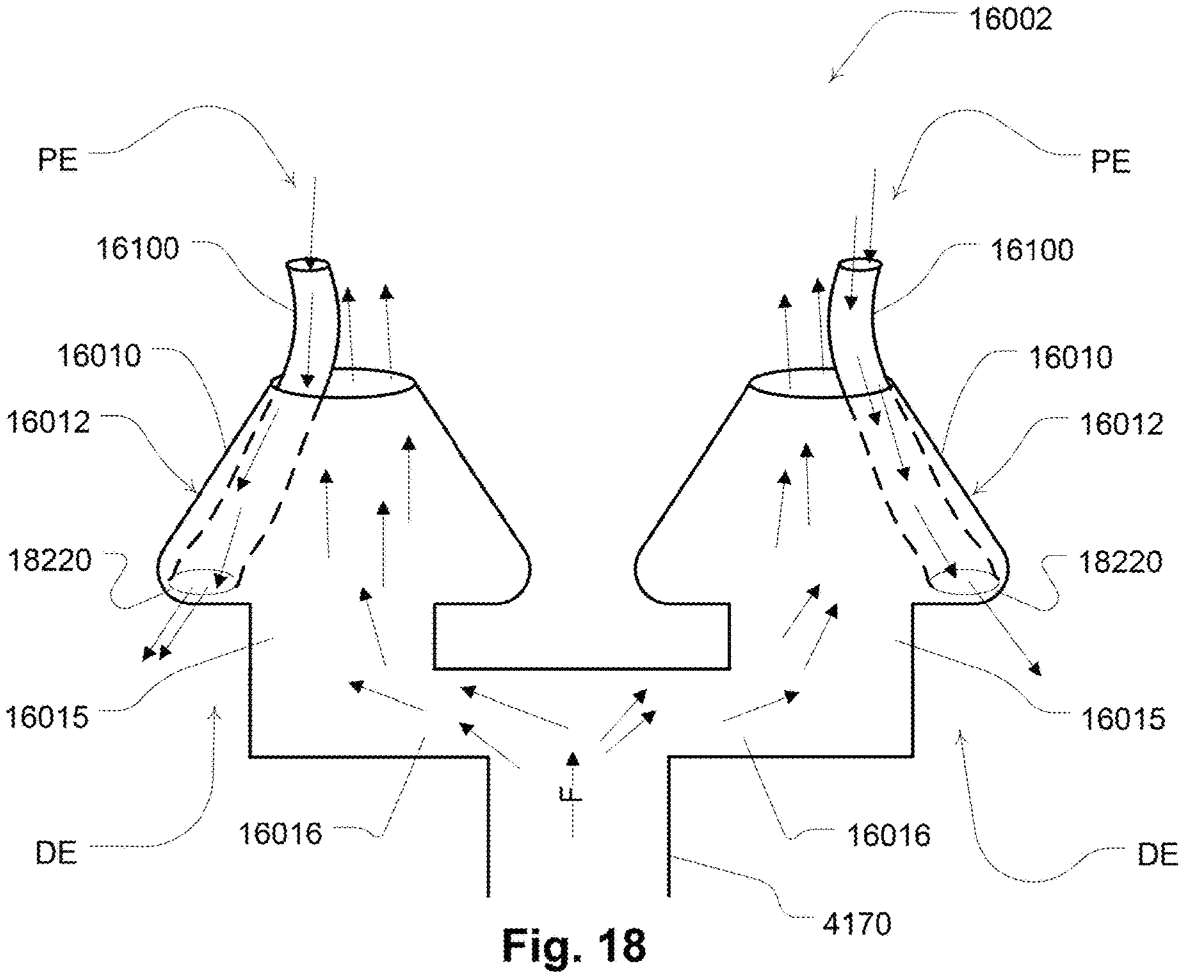
Figure 19A:
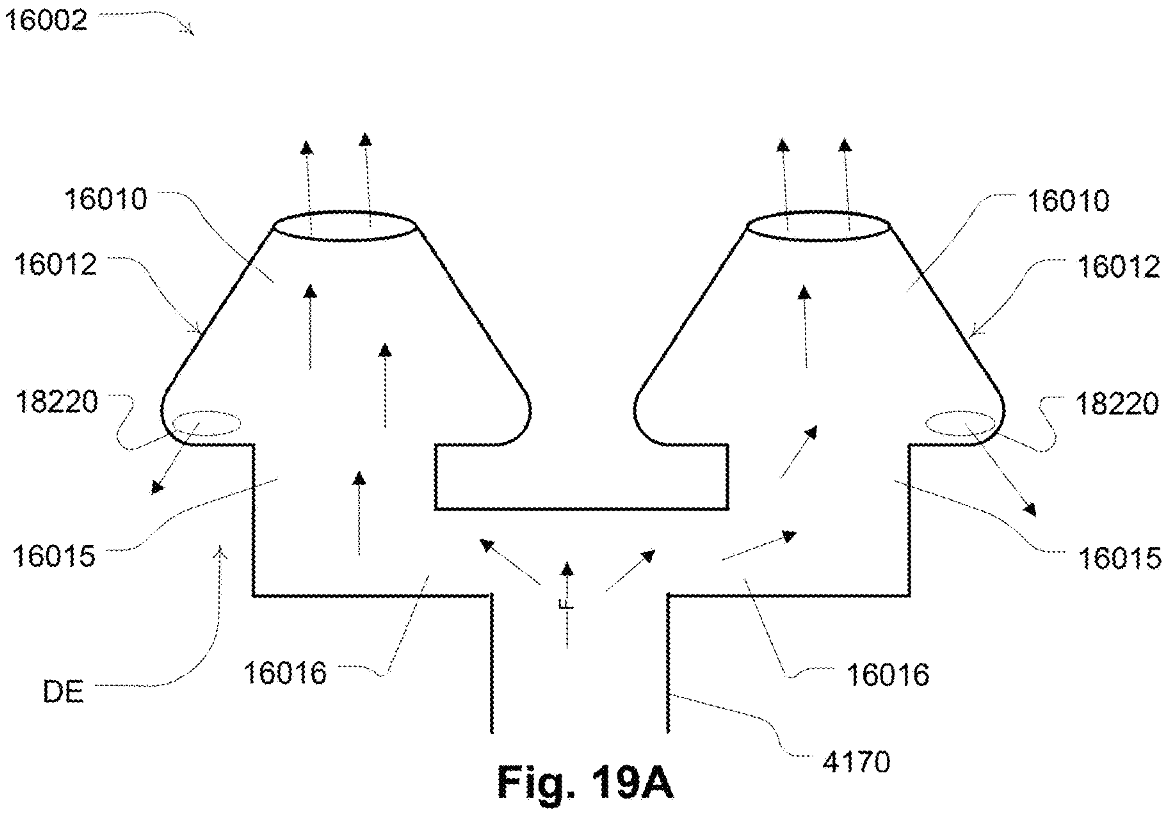
Figure 19B:
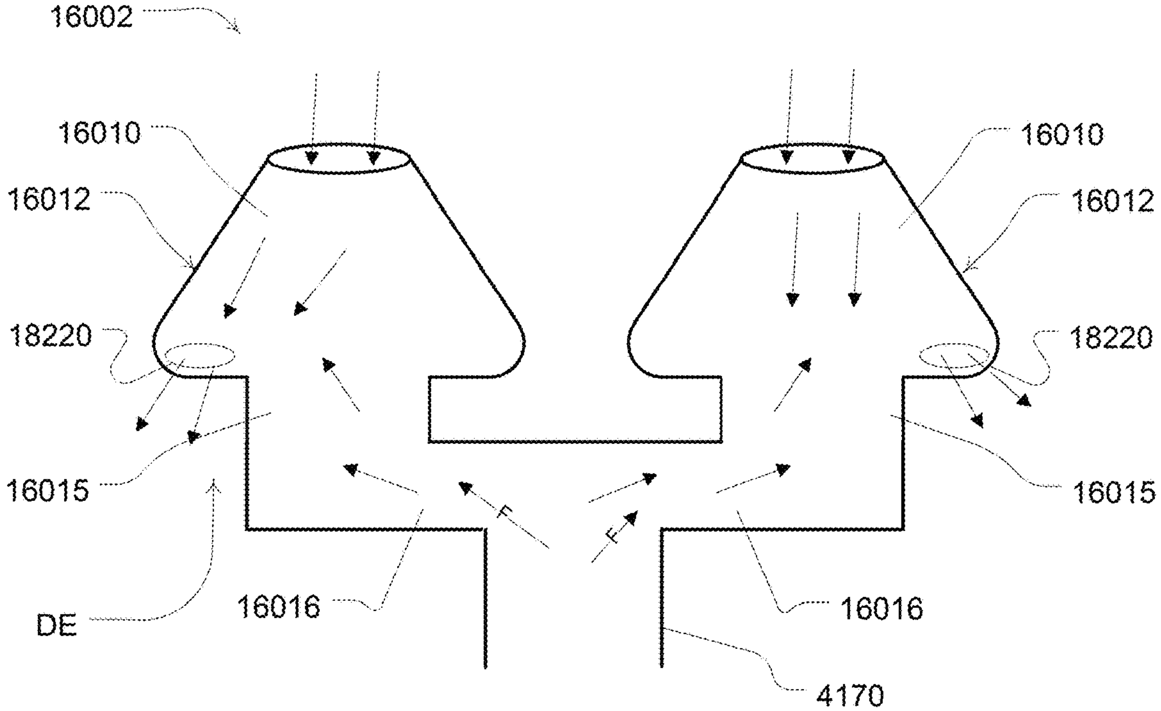
Figures 20A, 20B:
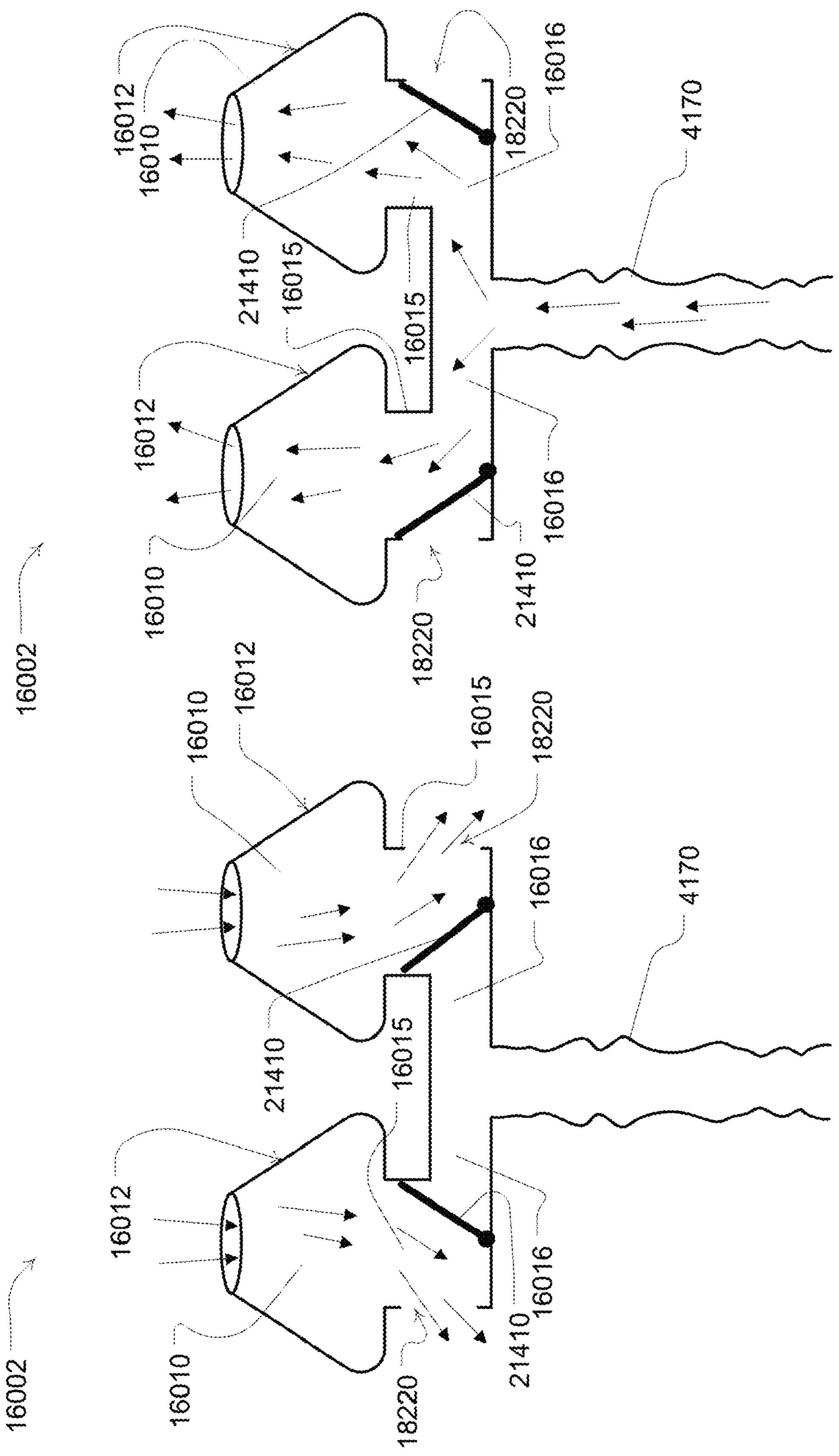
Figures 20C, 20D:
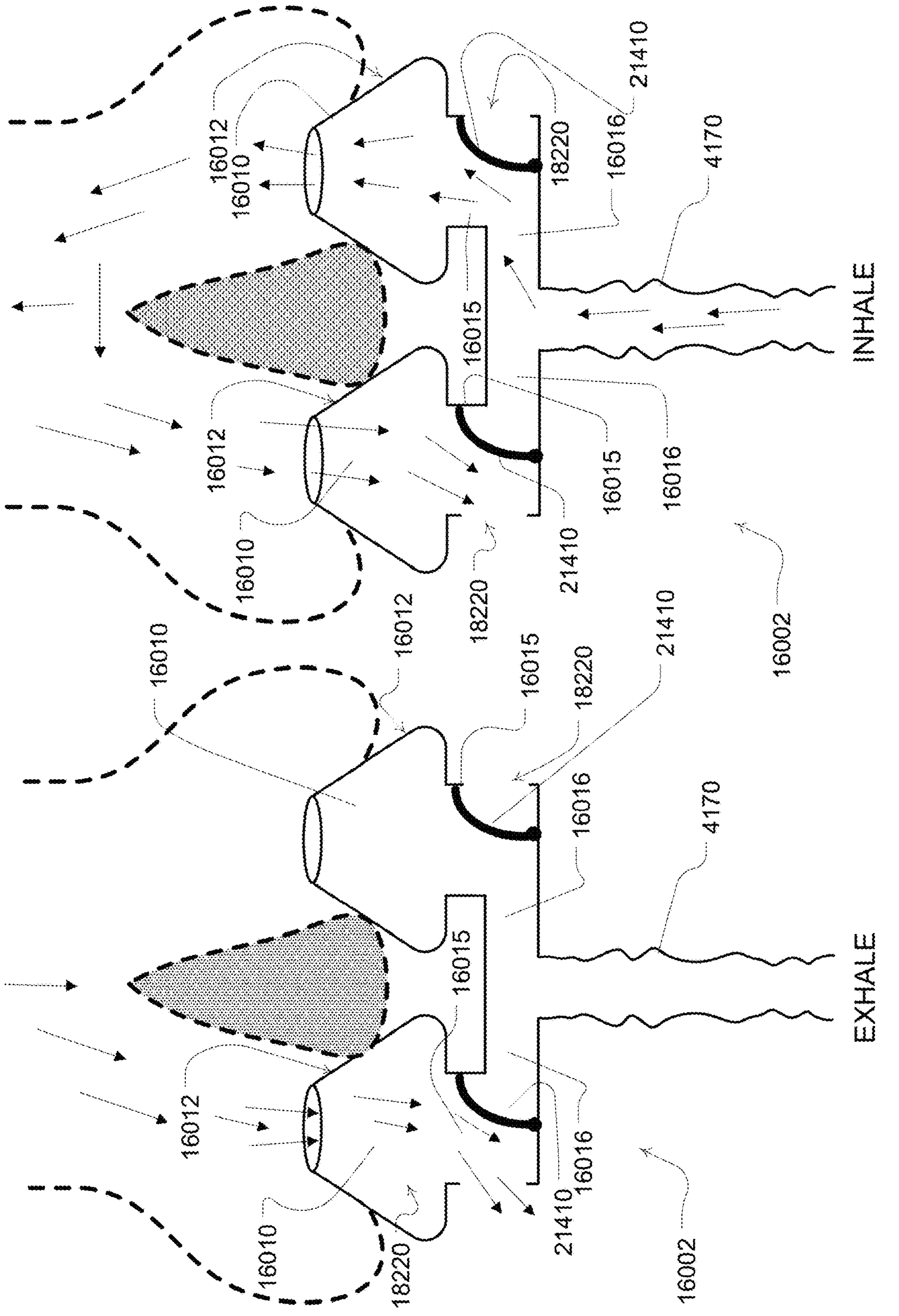
Figures 20E, 20F:
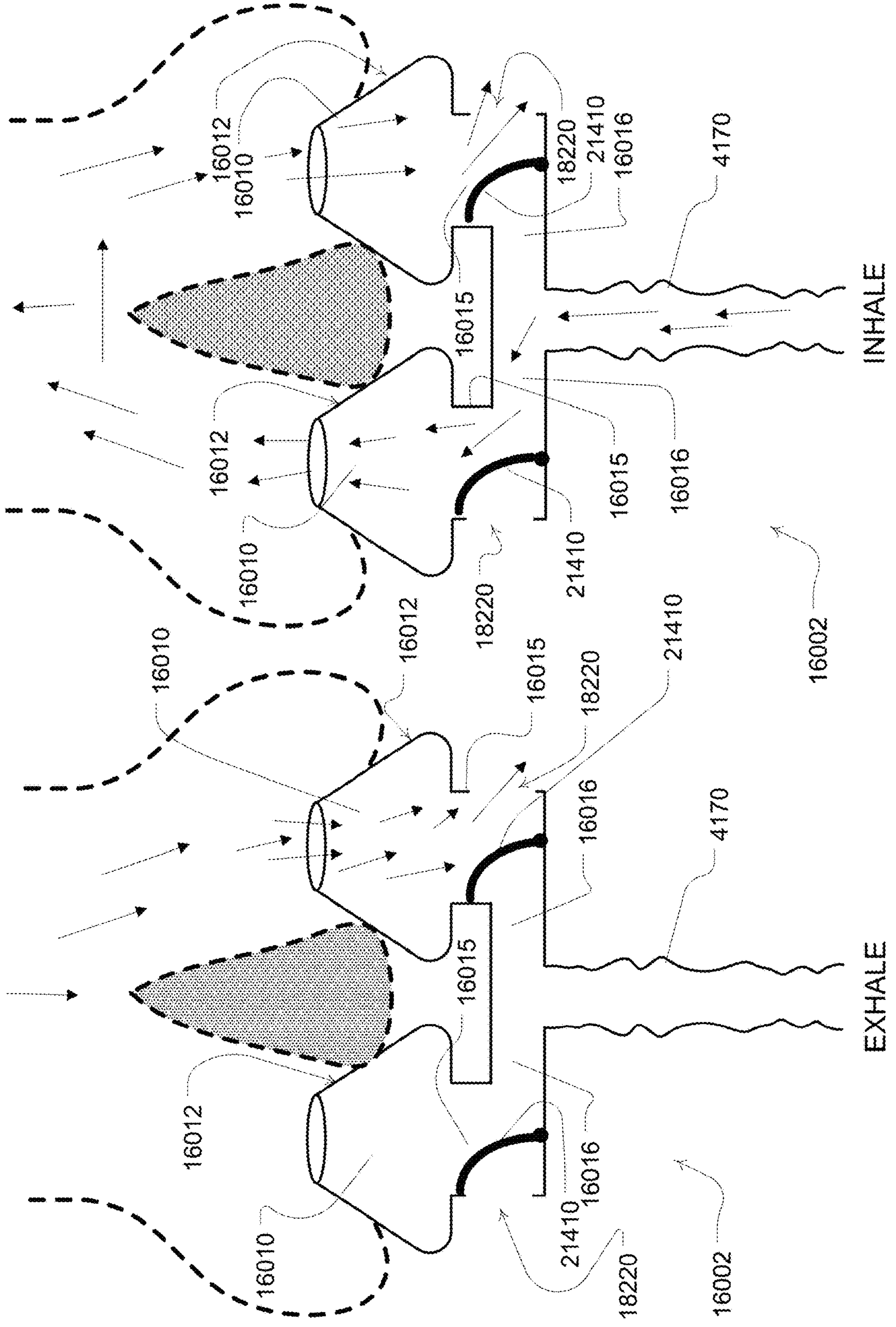
Figure 21:
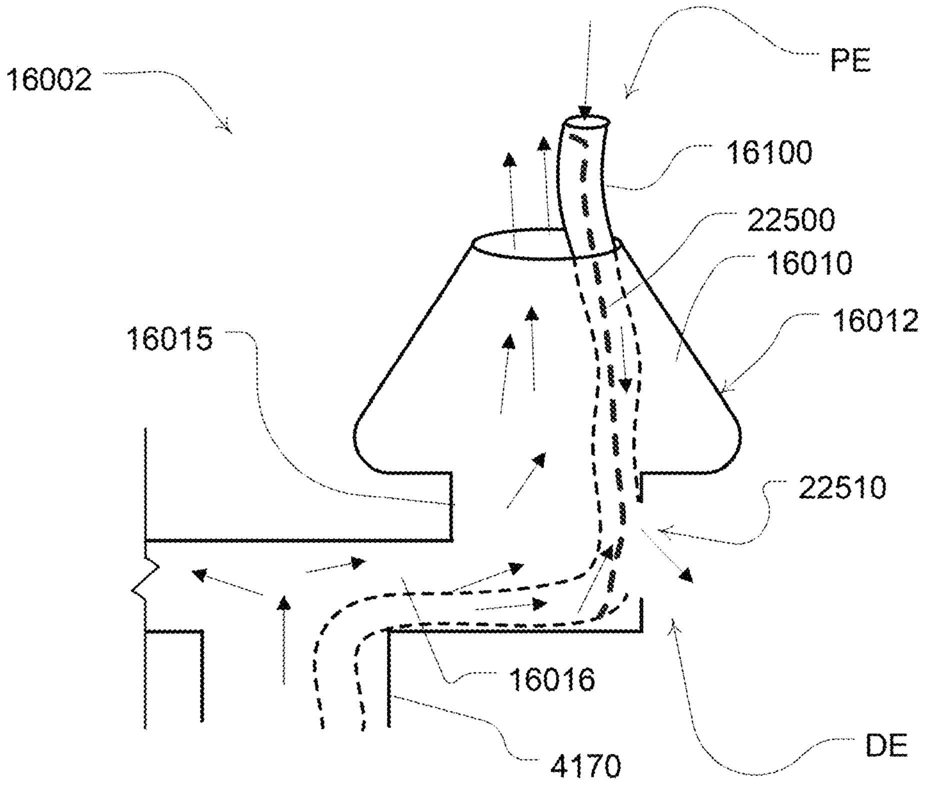
Figure 22:
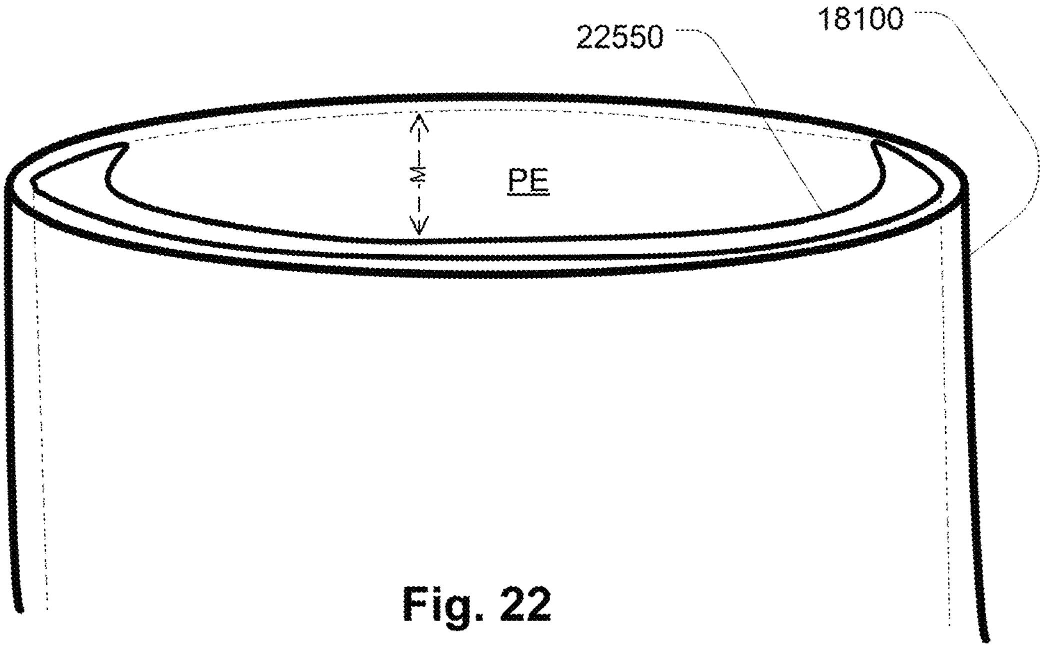
Figure 23A:
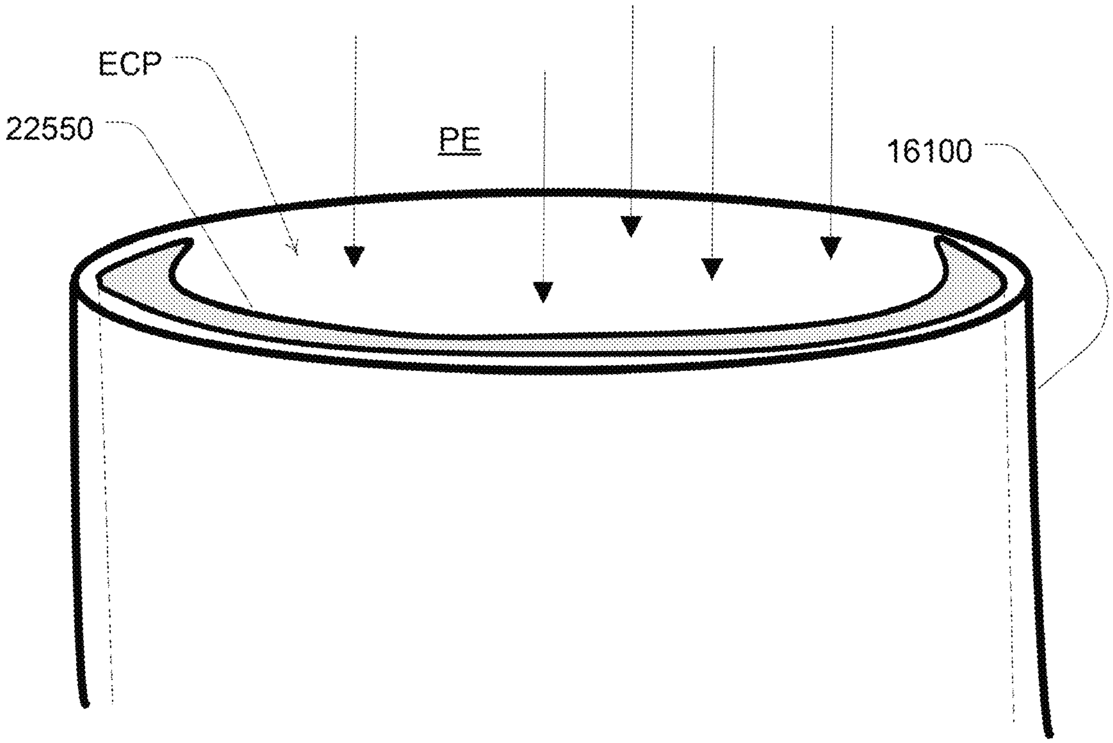
Figure 23B:
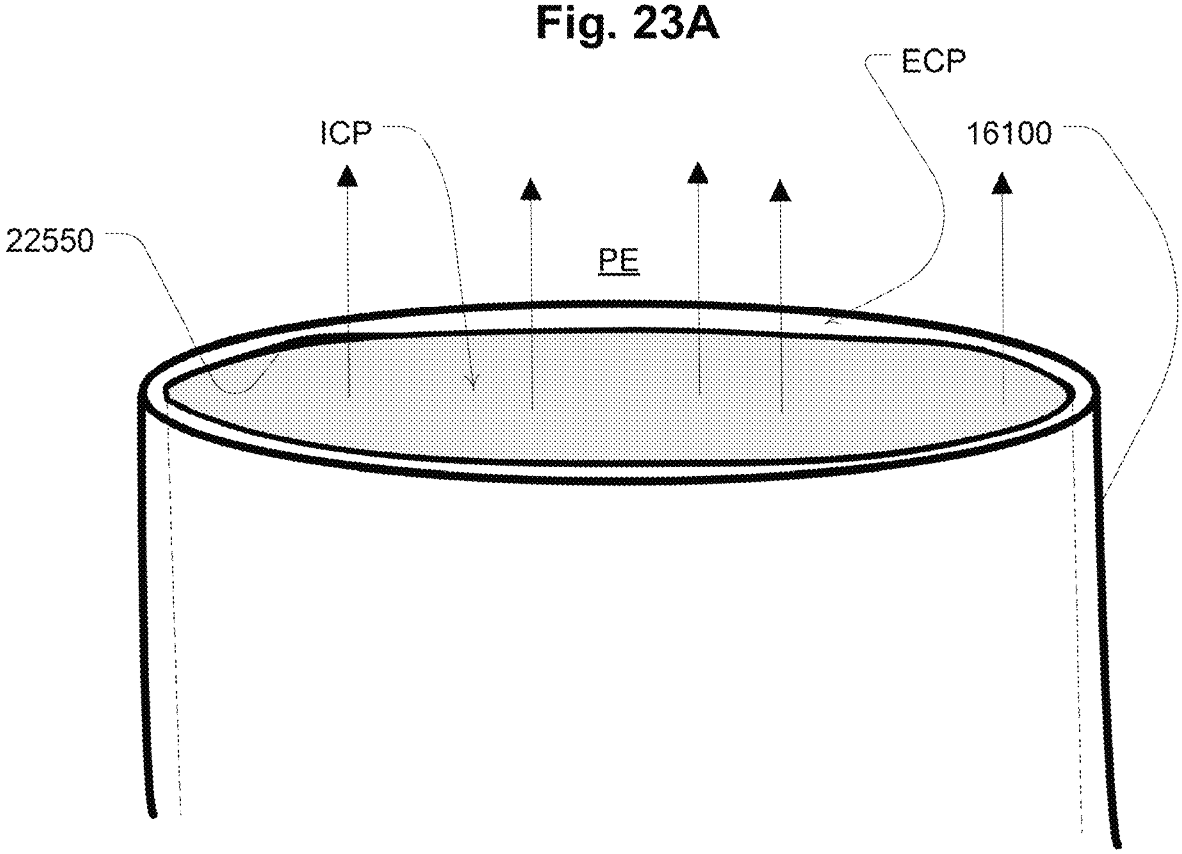
Figure 24:
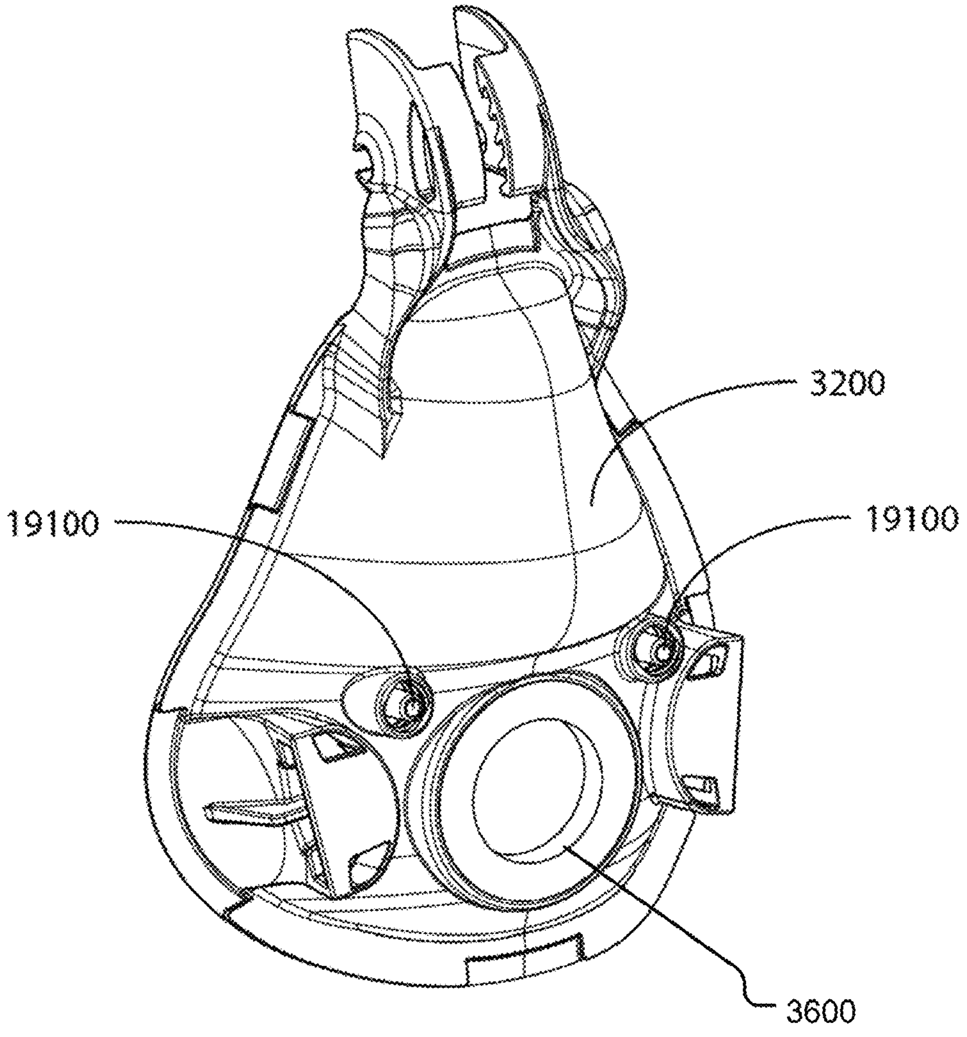
Figure 25A:
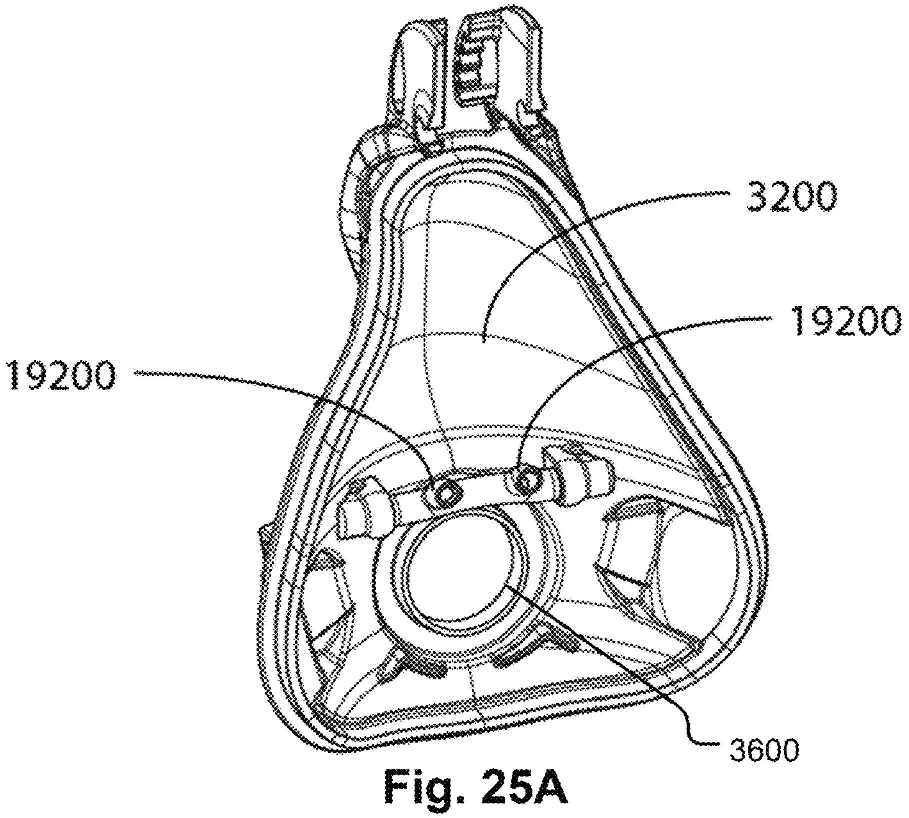
Figure 25B:
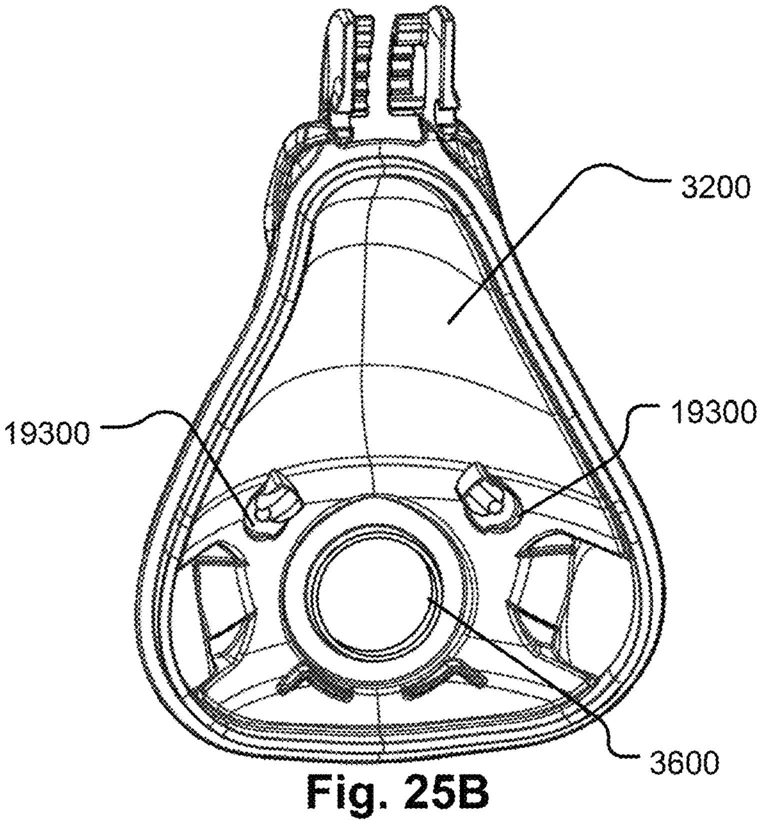
Figure 26:
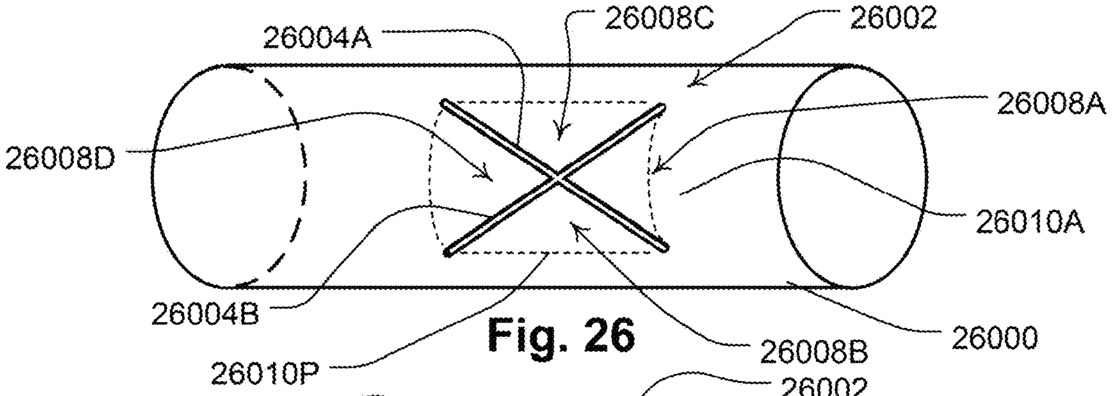
Figure 27A:
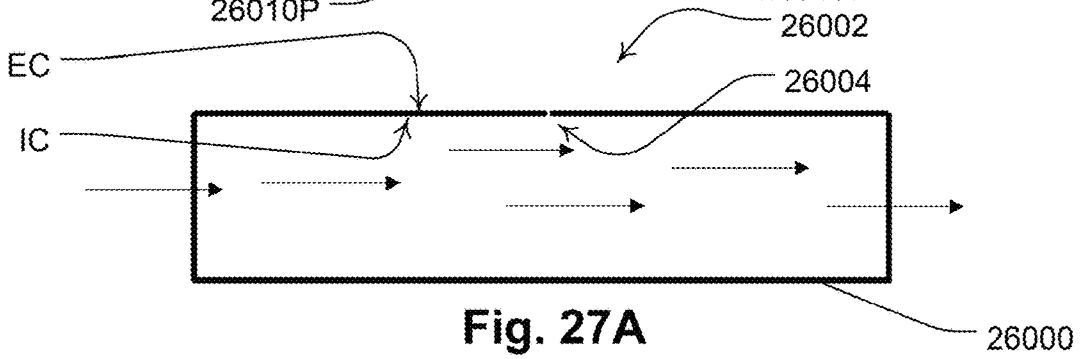
Figure 27B:
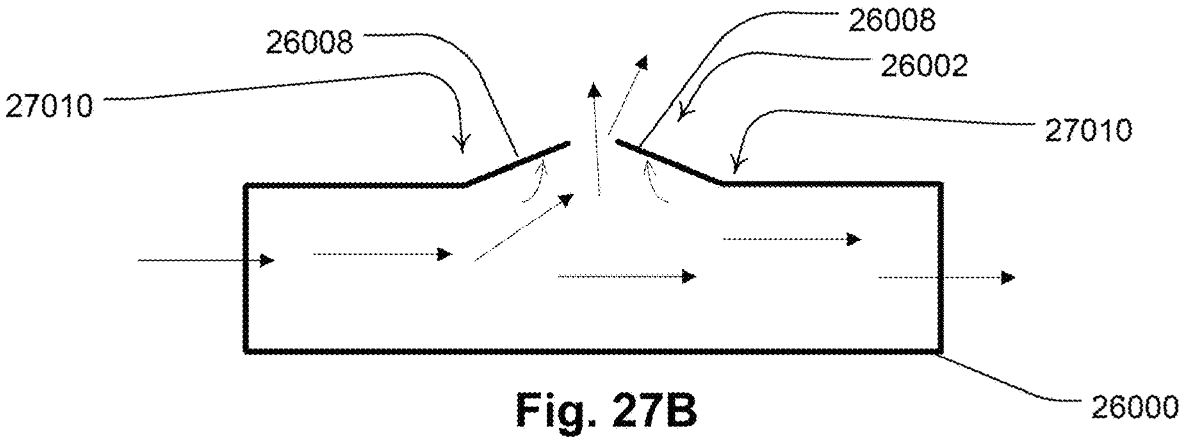
Figure 27C:
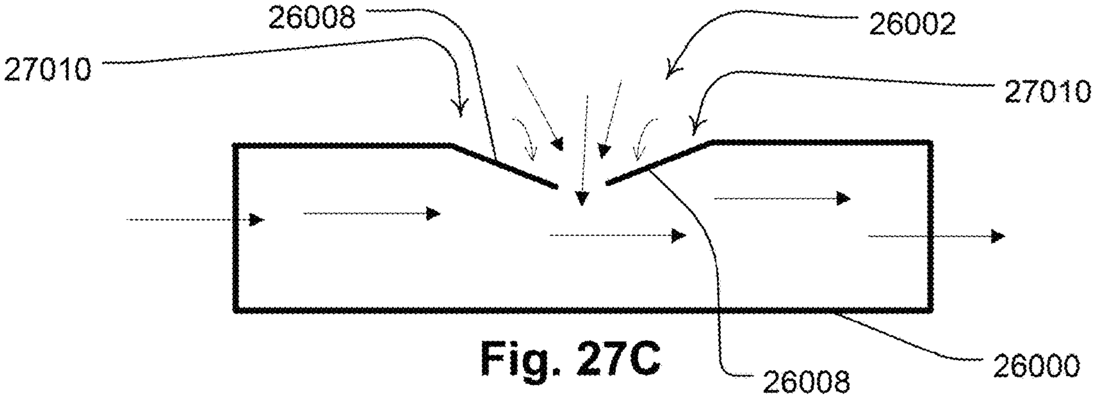
Figure 28A:
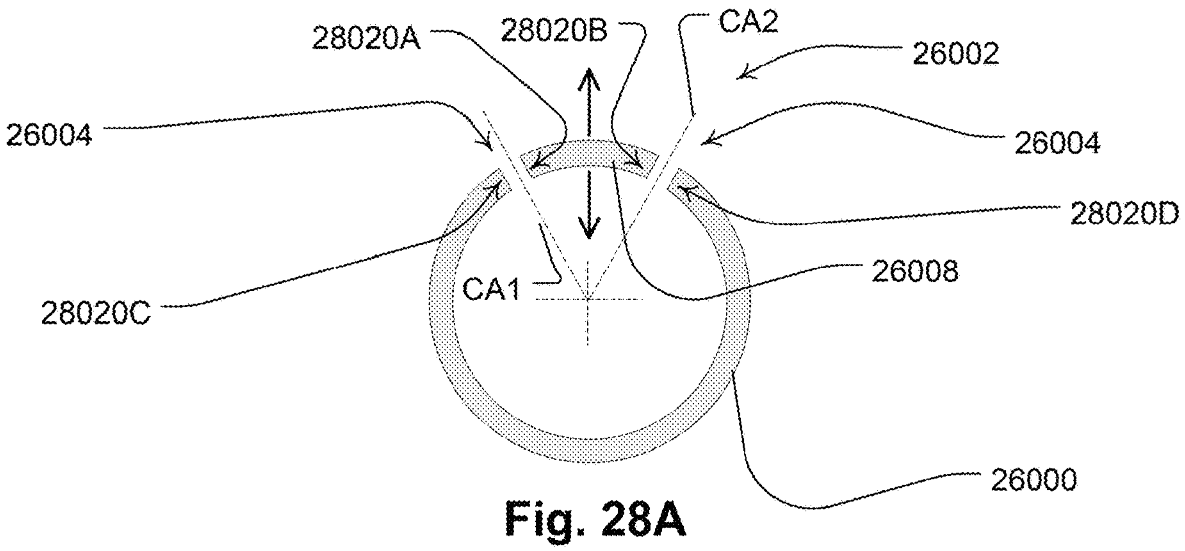
Figure 28B:
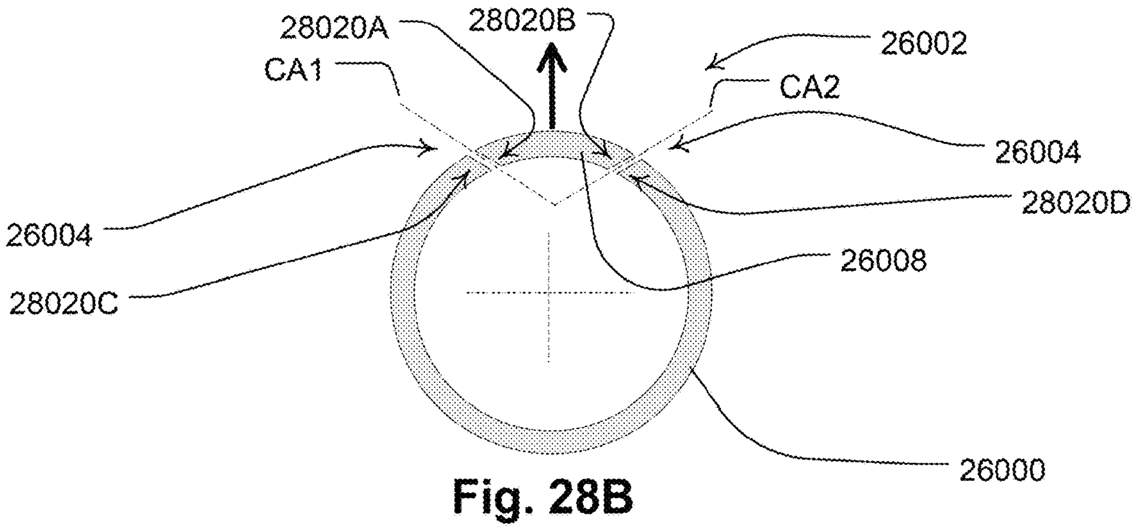
Figure 28C:
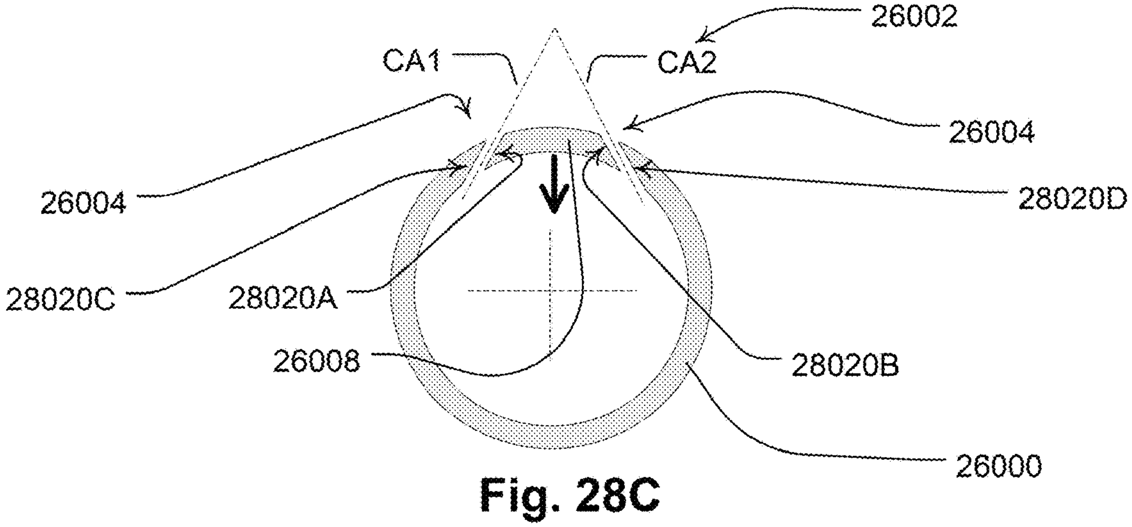
Figure 29A:
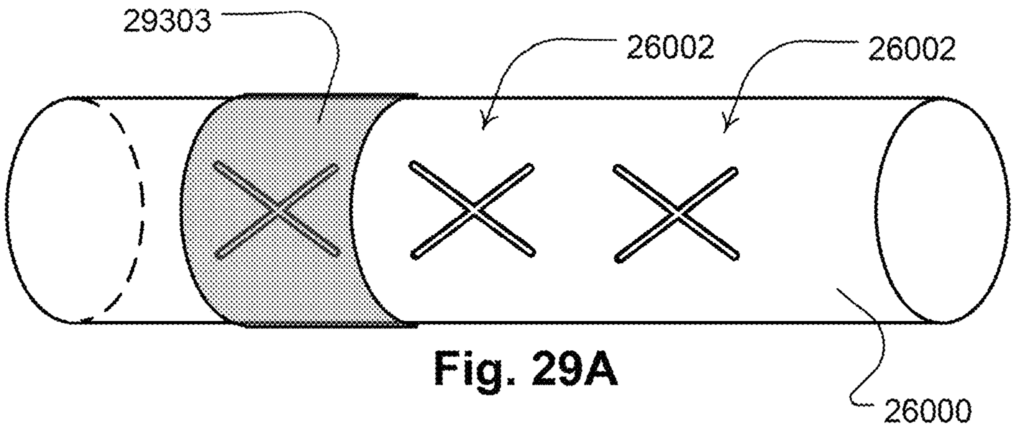
Figure 29B:
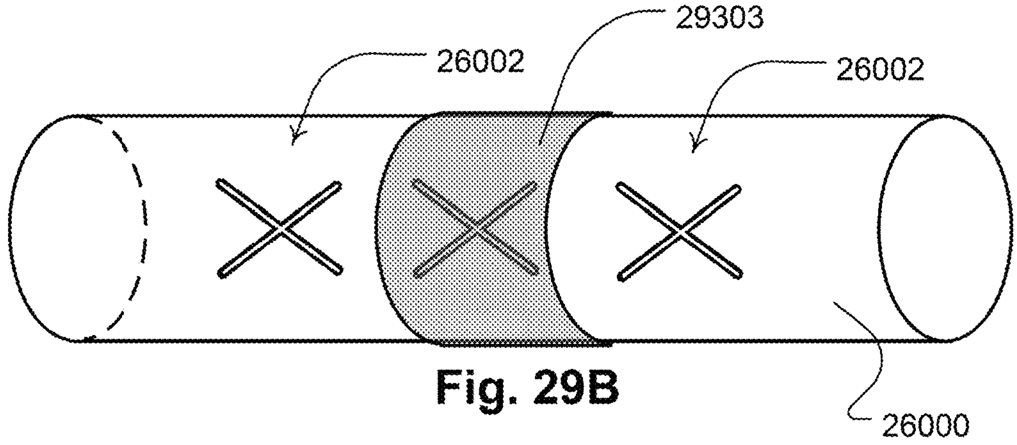
Figure 29C:
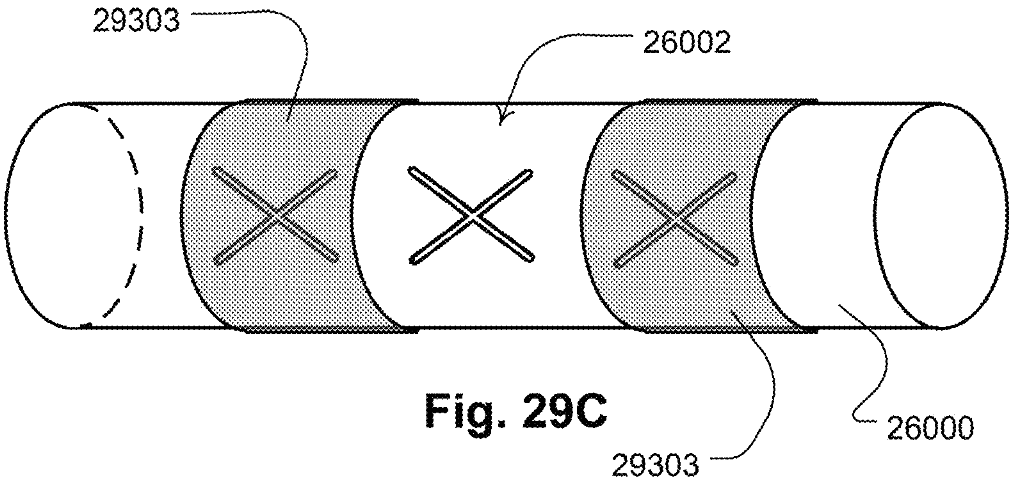
Figure 30A:
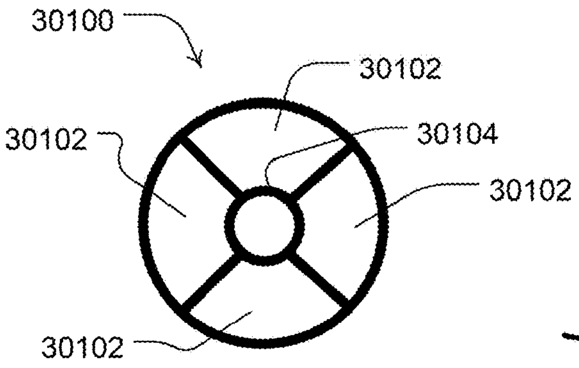
Figure 30B:
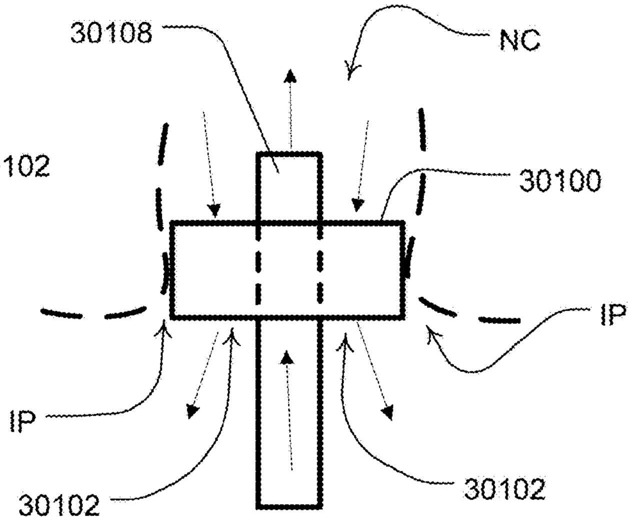
Figure 30C:
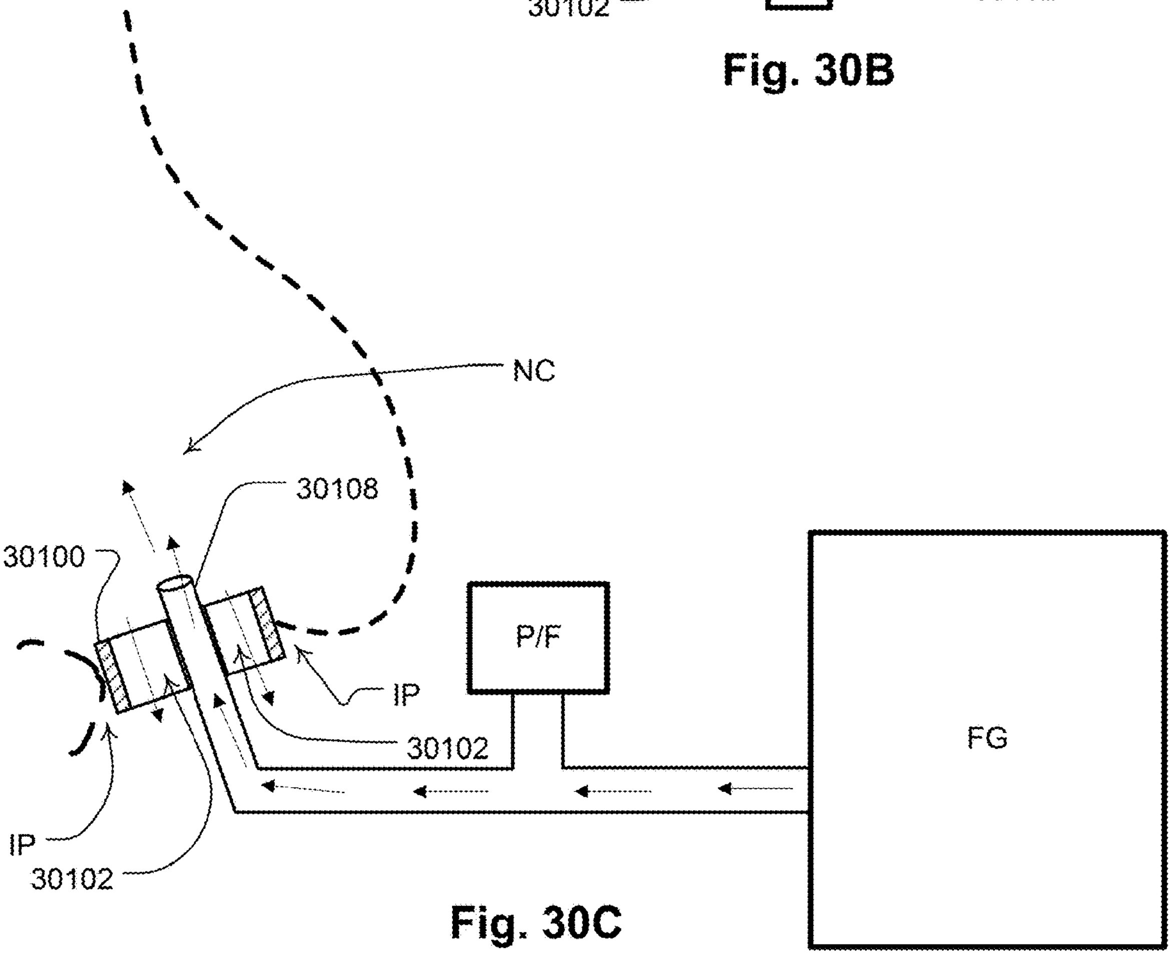
Figure 31A:
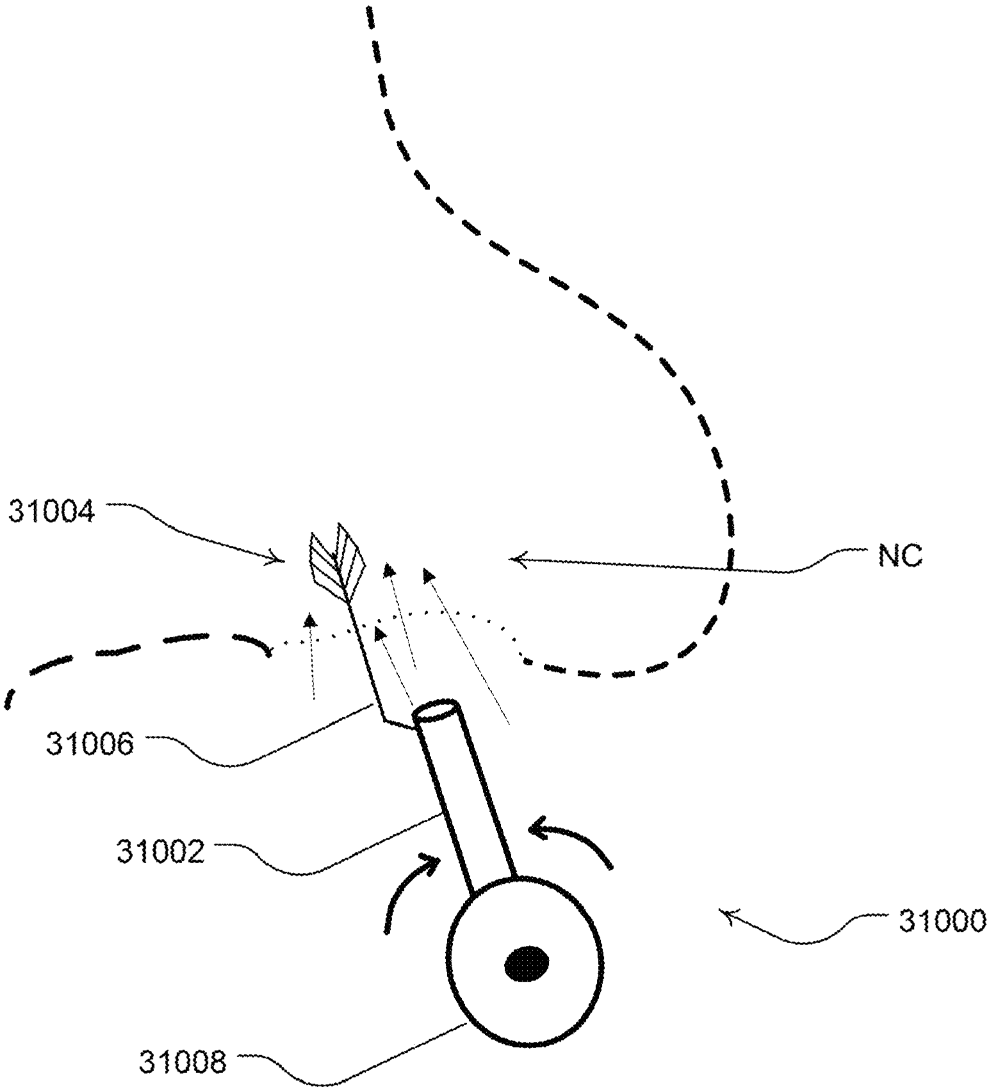
Figure 31B:
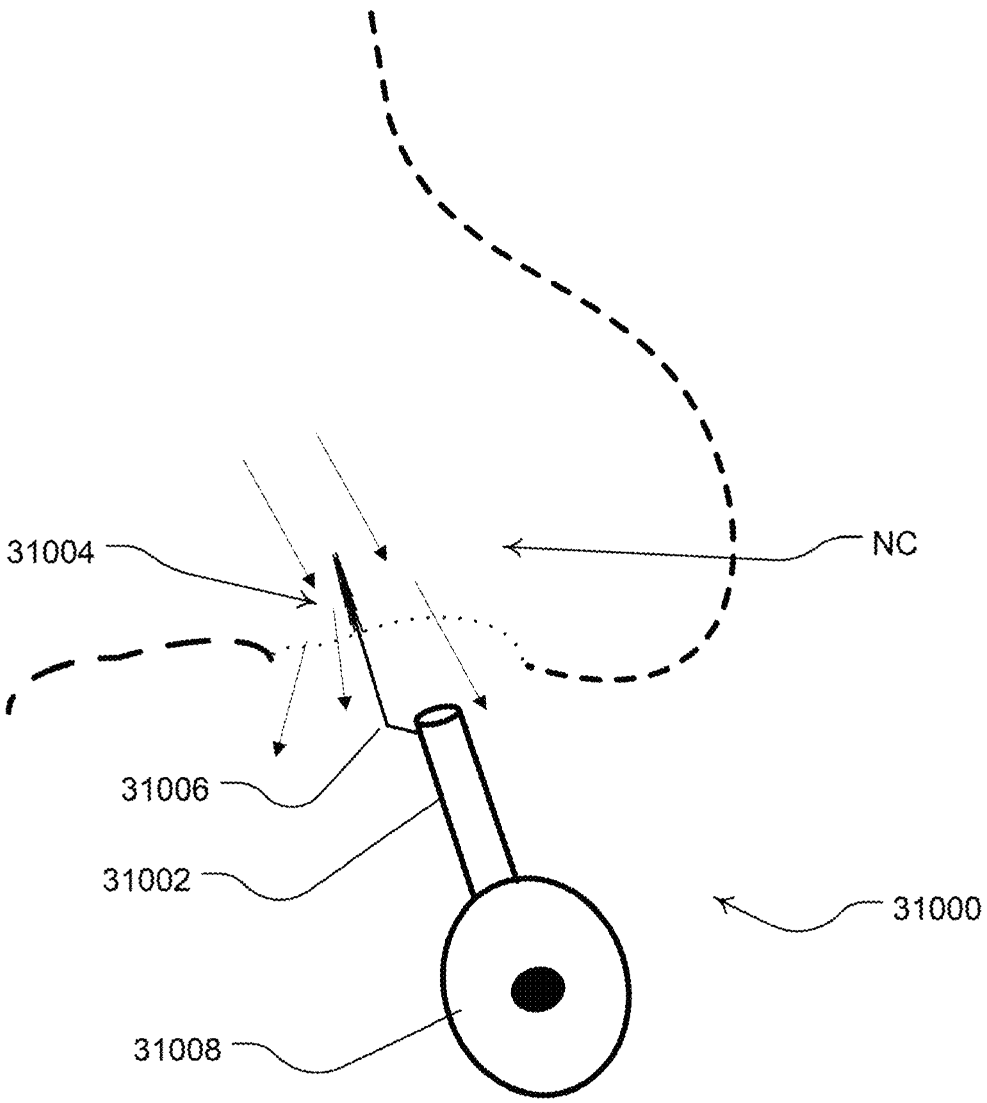
Figure 31C:
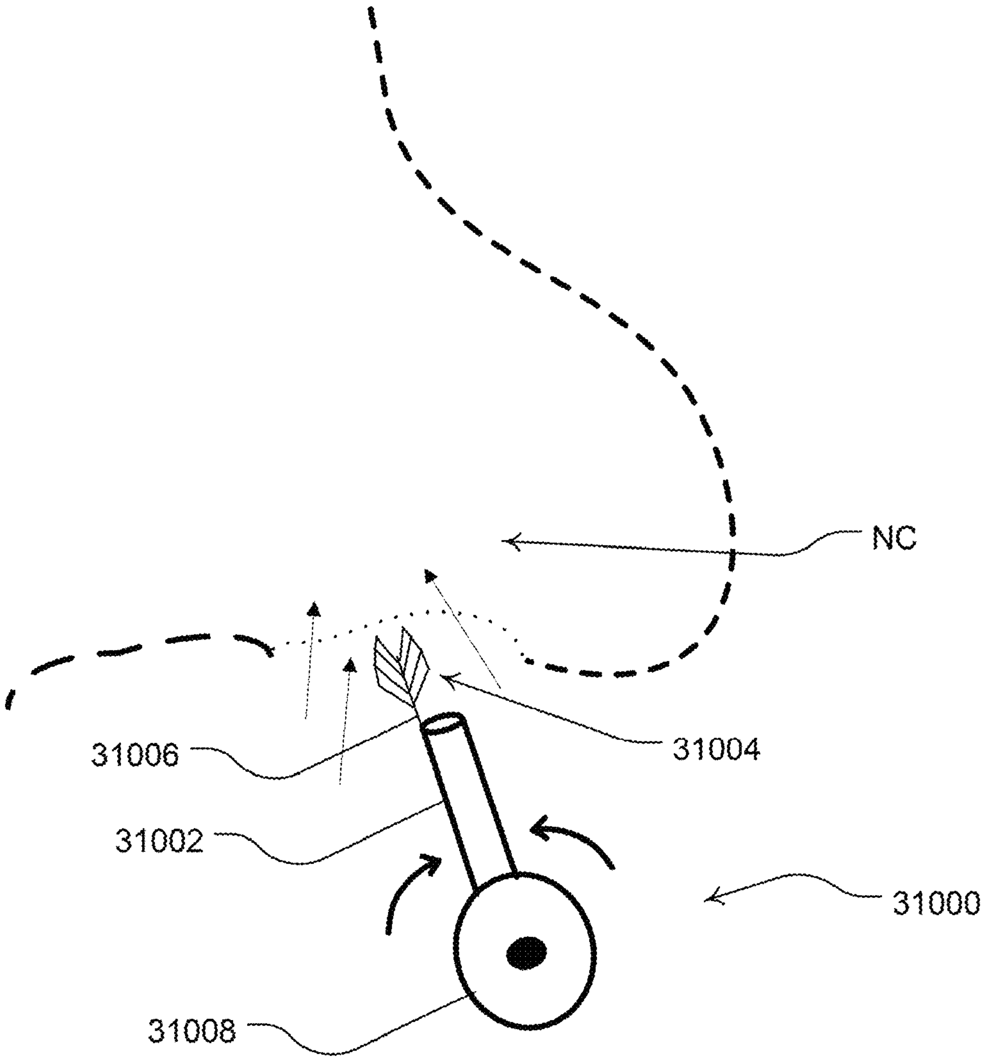
Figure 31D:
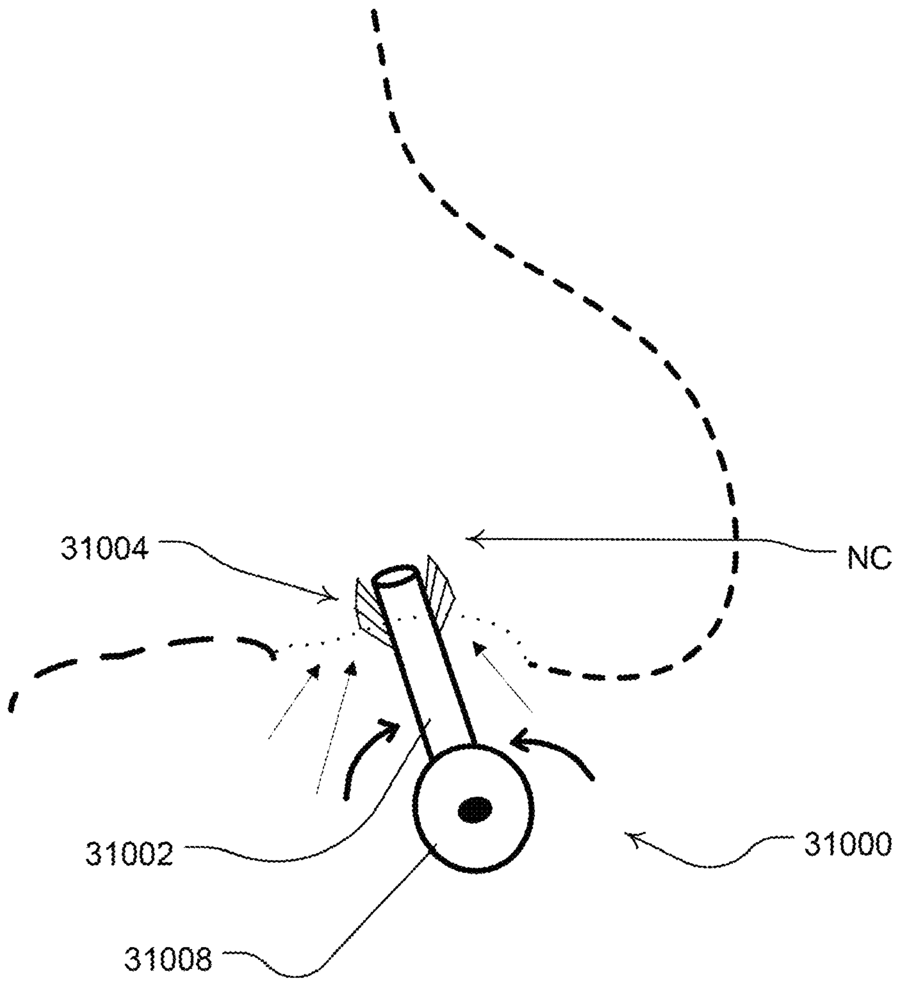

FIG. 6 shows a conventional nasal cannula;

FIG. 7 shows the nasal cannula of FIG. 6 in use with a mask;

FIG. 8 is an illustration of a nasal cannula with a coupler extension of the present technology;

FIGS. 9A, 9B, 9C and 9D illustrate various cross sectional profile for coupler extensions of the present technology taken along line A-A of FIG. 8;

FIG. 10A is an illustration of a nasal cannula with a coupler extension of the present technology in use with a mask;

FIG. 10B is an illustration of a nasal cannula with a coupler extension of the present technology in use with a mask showing a seat portion;

FIG. 11 is another illustration of a nasal cannula with a coupler extension of the present technology having a seat ridge, the figure also includes a cross sectional view of the coupler extension taken along line A-A;

FIG. 12 is another illustration of a nasal cannula with a coupler extension as shown in FIG. 11 in use with a mask;

FIG. 13 is an illustration of another version of a nasal cannula with a coupler extension of the present technology in use with a mask;

FIG. 14A is a plan view and a front elevation view of another example coupler extension for a nasal cannula of the present technology;

FIG. 14B is a front elevation view of another coupler extension for a nasal cannula of the present technology;

FIG. 14C is a front elevation view of another coupler extension for a nasal cannula of the present technology;

FIG. 15A is an illustration of a nasal interface of the present technology with nasal projections;

FIG. 15B is an illustration of another nasal interface of the present technology with nasal projections;

FIG. 16 shows the nasal interface of FIG. 15*a* in use by a patient;

FIGS. 17A and 17B show elevation and cross sectional views respectively a further example nasal interface of the present technology;

FIG. 18 is an illustration of a further nasal interface of the present technology with a pillow vent;

FIGS. 19A and 19B are illustrations of a further nasal interface of the present technology with pillow vents in showing inspiratory flow and expiratory flow respectively;

FIGS. 20A and 20B are illustrations of a further nasal interface of the present technology with vents showing expiratory and inspiratory operations respectively;

FIGS. 20C and 20D are illustrations of a further nasal interface of the present technology with vents showing expiratory and inspiratory operations respectively;

FIGS. 20E and 20F are illustrations of a further nasal interface of the present technology with vents showing expiratory and inspiratory operations respectively;

FIG. 21 is an illustration of a nasal pillow with a further example nasal projection of the present technology;

FIG. 22 is an illustration of a valve membrane of the example nasal projection FIG. 21;

FIGS. 23A and 23B show expiratory and inspiratory operations respectively of the valve membrane of the example nasal projection of FIG. 21;

FIG. 24 illustrates an external side of a mask frame with interface ports for coupling with supply conduits;

FIG. 25A shows a plenum chamber or patient side of a mask frame for some versions of the present technology;

FIG. 25B shows another plenum chamber or patient side of a mask frame of another version of the present technology;

FIG. 26 is an illustration of an example conduit slit valve, such as in a conduit of a cannula;

FIGS. 27A, 27B and 27C illustrate various operations of a conduit slit valve;

FIGS. 28A, 28B and 28C illustrate cross sectional views of several conduit slit valves;

FIGS. 29A, 29B and 29C illustrate various operations of a conduit with multiple slit valves and one or more a coupler sheathes;

FIG. 30A is a plan view of an example nare vent for use with a nasal cannula;

FIG. 30B show a side view of the example nare vent of FIG. 30A in a nare of a person;

FIG. 30C shows a sectional view of the example nare vent of FIG. 30A in a nare of a person;

FIG. 31A illustrates an example of a self-aligning cannula nozzle having a vane inserted within a nare of a person during inspiration;

FIG. 31B illustrates the example self-aligning cannula nozzle of FIG. 31A having a vane inserted within a nare of a person during expiration;

FIG. 31C illustrates another example of a self-aligning cannula nozzle having a vane and outlet outside a nare of a person; and FIG. 31D illustrates another example of a self-aligning cannula nozzle having a vane and outlet inside a nare of a person.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

5.1 Therapy

In one form, the present technology comprises a method for treating a respiratory disorder comprising the step of applying positive pressure to the entrance of the airways of a patient 1000.

5.1.1 Nasal CPAP for OSA

In one form, the present technology comprises a method of treating Obstructive Sleep Apnea in a patient by applying nasal continuous positive airway pressure to the patient.

In certain embodiments of the present technology, a supply of air at positive pressure is provided to the nasal passages of the patient via one or both nares.

5.2 Treatment Systems

In one form, the present technology comprises an apparatus for treating a respiratory disorder. The apparatus may comprise a PAP device 4000 for supplying pressurised respiratory gas, such as air, to the patient 1000 via an air circuit 4170 to a patient interface 3000.

5.3 Patient Interface 3000

A non-invasive patient interface 3000 in accordance with one aspect of the present technology comprises the following functional aspects: a seal-forming structure 3100, a plenum chamber 3200, a positioning and stabilising structure 3300 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange and a support flange. Preferably the sealing flange comprises a relatively thin member with a thickness of less than about 1 mm, for example about 0.25 mm to about 0.45 mm, that extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use. In use the sealing flange can readily respond to system pressure in the plenum chamber acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows or a naris pillow in accordance with an aspect of the present technology may include: a frusto-cone, at least a portion of which forms a seal on an underside of the patient's nose; a stalk or neck, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

5.3.2 Plenum Chamber 3200

Preferably the plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. Preferably the seal-forming structure 3100 extends in use about the entire perimeter of the plenum chamber 3200.

5.3.3 Positioning and Stabilising Structure 3300

The patient interface 3000 may be held in its operating position by the positioning and stabilising structure 3300. For example, the seal-forming structure 3100 of the patient interface 3000 of the present technology is held in sealing position in use by the positioning and stabilising structure 3300.

5.3.4 Vent 3400

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

Preferably the vent 3400 is located in the plenum chamber 3200. Alternatively, the vent 3400 is located in a decoupling structure 3500, e.g. a swivel 3510.

5.3.5 Decoupling Structure(s) 3500

In one form the patient interface 3000 includes at least one decoupling structure 3500, for example a swivel 3510 or a ball and socket 3520.

5.3.6 Connection Port 3600

Connection port 3600 allows for connection to the air circuit 4170.

5.3.7 Forehead Support 3700

In one form, the patient interface 3000 includes a forehead support 3700.

5.3.8 Anti-Asphyxia Valve 3800

In one form, the patient interface 3000 includes an anti-asphyxia valve 3800.

5.3.9 Ports 3900

In one form of the present technology, a patient interface 3000 includes one or more ports that allow access to the volume within the plenum chamber 3200. In one form this allows a clinician to supply supplemental oxygen. In one form this allows for the direct measurement of a property of gases within the plenum chamber 3200, such as the pressure.

5.4 PAP Device 4000

An example flow generator may be a PAP device 4000 in accordance with one aspect of the present technology and may comprise mechanical and pneumatic components 4100, electrical components 4200 and may be programmed to execute one or more therapy algorithms. The PAP device preferably has an external housing 4010, preferably formed in two parts, an upper portion 4012 and a lower portion 4014. Furthermore, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The PAP device 4000 may have one or more pneumatic paths depending on the types of patient interface coupled with the device. A pneumatic path of the PAP device 4000 preferably comprises an inlet air filter 4112, an inlet muffler 4122, a pressure device 4140 capable of supplying air at positive pressure (preferably a blower 4142) and/or a flow device capable of supplying air at a desired flow rate (e.g., a blower or oxygen supply line etc.), a pneumatic block 4020 and an outlet muffler 4124. One or more transducers 4270, such as pressure sensors or pressure transducers 4272 and flow sensors or flow transducers 4274 may be included in the pneumatic paths.

The preferred pneumatic block 4020 comprises a portion of the pneumatic path that is located within the external housing 4010 and may house the pressure device 4140.

The PAP device 4000 preferably has an electrical power supply 4210, one or more input devices 4220, a central controller 4230, a therapy device controller 4240, a pressure device 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

The PAP device may be configured to provide any of the pressure or flow therapies described throughout this specification.

5.4.1 PAP Device Mechanical & Pneumatic Components 4100

5.4.1.1 Air Filter(s) 4110

A PAP device in accordance with one form of the present technology may include an air filter 4110, or a plurality of air filters 4110.

In one form, an inlet air filter 4112 is located at the beginning of the pneumatic path upstream of a pressure device 4140. See FIG. 4*b*.

In one form, an outlet air filter 4114, for example an antibacterial filter, is located between an outlet of the pneumatic block 4020 and a patient interface 3000. See FIG. 4*b*.

5.4.1.2 Muffler(s) 4120

In one form of the present technology, an inlet muffler 4122 is located in the pneumatic path upstream of a pressure device 4140. See FIG. 4*b*.

In one form of the present technology, an outlet muffler 4124 is located in the pneumatic path between the pressure device 4140 and a patient interface 3000. See FIG. 4*b*.

5.4.1.3 Pressure Device 4140

In one form of the present technology, a pressure device 4140 for producing a flow, or a supply, of air at positive pressure is a controllable blower 4142. For example the blower 4142 may include a brushless DC motor 4144 with one or more impellers housed in a volute. The blower may be preferably capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may include a blower as described in any one of the following patents or patent applications the contents of which are incorporated herein in their entirety: U.S. Pat. Nos. 7,866,944; 8,638,014; 8,636,479; and PCT patent application publication number WO 2013/020167.

The pressure device 4140 is under the control of the therapy device controller 4240.

In other forms, a pressure device 4140 may be a piston-driven pump, a pressure regulator connected to a high pressure source (e.g. compressed air reservoir) or bellows.

5.4.1.4 Transducer(s) 4270

Transducers may be internal of the device, or external of the PAP device. External transducers may be located for example on or form part of the air circuit, e.g. the patient interface. External transducers may be in the form of non-contact sensors such as a Doppler radar movement sensor that transmit or transfer data to the PAP device.

In one form of the present technology, one or more transducers 4270 are located upstream and/or downstream of the pressure device 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Transducer 4274

A flow rate transducer 4274 in accordance with the present technology may be based on a differential pressure transducer, for example, an SDP600 Series differential pressure transducer from SENSIRION.

In use, a signal representing a flow rate such as a total flow Qt from the flow transducer 4274 is received by the central controller 4230.

5.4.1.4.2 Pressure Transducer 4272

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the central controller 4230.

5.4.1.4.3 Motor Speed Transducer 4276

In one form of the present technology a motor speed transducer 4276 is used to determine a rotational velocity of the motor 4144 and/or the blower 4142. A motor speed signal from the motor speed transducer 4276 is preferably provided to the therapy device controller 4240. The motor speed transducer 4276 may, for example, be a speed sensor, such as a Hall effect sensor.

5.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

5.4.1.6 Air Circuit 4170

An air circuit 4170 in accordance with an aspect of the present technology is a conduit or a tube constructed and arranged in use to allow a flow of air or breathable gasses to travel between two components such as the pneumatic block 4020 and the patient interface 3000.

In particular, the air circuit may be in fluid connection with the outlet of the pneumatic block and the patient interface. The air circuit may be referred to as air delivery tube. In some cases there may be separate limbs of the circuit for inhalation and exhalation and/or for multiple patient interfaces. In other cases a single limb is used.

5.4.1.7 Oxygen Delivery 4180

In one form of the present technology, supplemental oxygen 4180 is delivered to one or more points in the pneumatic path, such as upstream of the pneumatic block 4020, to the air circuit 4170 and/or to the patient interface 3000, such as via the nasal projections or prongs of a cannula.

5.4.2 PAP Device Electrical Components 4200

5.4.2.1 Power Supply 4210

A power supply 4210 may be located internal or external of the external housing 4010 of the PAP device 4000.

In one form of the present technology power supply 4210 provides electrical power to the PAP device 4000 only. In another form of the present technology, power supply 4210 provides electrical power to both PAP device 4000 and humidifier 5000.

5.4.2.2 Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

5.4.2.3 Central Controller 4230

In one form of the present technology, the central controller 4230 is one or a plurality of processors suitable to control a PAP device 4000.

Suitable processors may include an x86 INTEL processor, a processor based on ARM Cortex-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier controller 5250.

In some forms of the present technology, the central controller 4230 is configured to implement the one or more methodologies described herein such as the one or more algorithms. In some cases, the central controller 4230 may be integrated with a PAP device 4000. However, in some forms of the present technology the central controller 4230 may be implemented discretely from the flow generation components of the PAP device 4000, such as for purpose of performing any of the methodologies described herein without directly controlling delivery of a respiratory treatment. For example, the central controller 4230 may perform any of the methodologies described herein for purposes of determining control settings for a ventilator or other respiratory related events by analysis of stored data such as from any of the sensors described herein.

5.4.2.3.1 Clock 4232

Preferably PAP device 4000 includes a clock 4232 that is connected to the central controller 4230.

5.4.2.3.2 Therapy Device Controller 4240

In one form of the present technology, therapy device controller 4240 is a pressure control module 4330 that forms part of the algorithms executed by the central controller 4230. The therapy device controller 4240 may be a flow control module that forms part of the algorithms executed by the central controller 4230. In some examples it may be both a pressure control and flow control module.

In one form of the present technology, therapy device controller 4240 may be one or more dedicated motor control integrated circuits. For example, in one form a MC33035 brushless DC motor controller, manufactured by ONSEMI is used.

5.4.2.3.3 Protection Circuits 4250

Preferably a PAP device 4000 in accordance with the present technology comprises one or more protection circuits 4250.

The one or more protection circuits 4250 in accordance with the present technology may comprise an electrical protection circuit, a temperature and/or pressure safety circuit.

5.4.2.3.4 Memory 4260

In accordance with one form of the present technology the PAP device 4000 includes memory 4260, preferably non-volatile memory. In some forms, memory 4260 may include battery powered static RAM. In some forms, memory 4260 may include volatile RAM.

Preferably memory 4260 is located on the PCBA 4202. Memory 4260 may be in the form of EEPROM, or NAND flash.

Additionally or alternatively, PAP device 4000 includes removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms.

5.4.2.4 Data Communication Systems 4280

In one preferred form of the present technology, a data communication interface 4280 is provided, and is connected to the central controller 4230. Data communication interface 4280 is preferably connectable to remote external communication network 4282 and/or a local external communication network 4284. Preferably remote external communication network 4282 is connectable to remote external device 4286. Preferably local external communication network 4284 is connectable to local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

5.4.2.5 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.5.1 Display Driver 4292

A display driver 4292 receives as an input the characters, symbols, or images intended for display on the display 4294, and converts them to commands that cause the display 4294 to display those characters, symbols, or images.

5.4.2.5.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5 Humidifier 5000

In one form of the present technology there is provided a humidifier 5000 as shown in FIG. 5*a* to change the absolute humidity of air or gas for delivery to a patient relative to ambient air. Typically, the humidifier 5000 is used to increase the absolute humidity and increase the temperature of the flow of breathable gas relative to ambient air before delivery to the patient's airways.

5.6 Additional Patient Interface for Optional Therapies

Some patients have a need for multiple therapies. For example, some patients may require supplemental gas therapy. For example, an oxygen therapy may be delivered to the patient by use of a nasal cannula where prongs of the cannula supply the oxygen at the patient's nares. Unlike nasal CPAP, such a therapy does not typically supply the gas or air at therapeutic pressure(s) so as to treat events of sleep disordered breathing such as obstructive apnea or obstructive hypopneas. Such an oxygen treatment may be considered with reference to the illustration of FIG. 6. The traditional nasal cannula 7002 includes nasal prongs 7004*a*, 7004*b* which can supply oxygen at the nares of the patient. Such nasal prongs do not generally form a seal with the inner or outer skin surface of the nares. The gas to the nasal prongs may typically be supplied by one or more gas supply lumen 7006*a*, 7006*b* that are coupled with the nasal cannula. Such tubes may lead to an oxygen source. Alternatively, in some cases, such a nasal cannula may provide a high air flow therapy to the nares. Such a high flow therapy (HFT) may be that described in U.S. Patent Application Publication No. 2011-0253136 filed as International Application PCT/AU09/00671 on May 28, 2009, the entire disclosure of which is incorporated herein by cross reference. In such a case, the lumen from the nasal cannula lead to a flow generator that generates the air flow for high flow therapy.

During delivery of such supplemental gas therapies with a traditional nasal cannula, it may be desirable to periodically provide a further therapy, such as a pressurized gas therapy or positive airway pressure therapy (PAP). Such therapies may require higher pressures (e.g. up to 20 cm $H_2O$ or 30 cm $H_2O$) than pressures achieved for supplemental gas therapies, and thus may require a patient interface to form a pressure seal with the patient's respiratory system in order to deliver and sustain the higher pressures.

For example, during oxygen therapy with a traditional nasal cannula, it may be desirable to provide a patient with a traditional CPAP therapy when a patient goes to sleep or traditional Pressure Support therapy. These additional therapies may require a sealing patient interface, for example a mask such as a nasal mask or mouth and nose mask. Such an example may be considered with reference to FIG. 7. When the mask 8008 is applied to the patient over the traditional nasal cannula, one or more of the components of the nasal cannula may interfere with the mask's seal forming structure (e.g., cushion 8010) so as to prevent a good seal with the patient. For example, as shown in FIG. 7, the lumen 7006*a*, 7006*b* may interfere with a cushion 8010 of the mask. This may result in a substantial cannula induced leak CIL at or near the lumen which may prevent the desired therapy pressure levels from being achieved in the mask. Apparatus and therapies described herein may be implemented to address such issues.

5.6.1 Modified Nasal Cannula Embodiments

In some implementations of the present technologies, a modified nasal cannula may be implemented to permit its use with changing therapy needs. For example, as illustrated in FIG. 8, the nasal cannula 9002 includes a set of projections (e.g., one or more prongs 9004*a*, 9004*b*). Each projection or prong may extend into a naris of a user. The projection serves as a conduit to deliver or direct a flow of gas into the naris of the user. The nasal cannula 9002 will also typically include one or more coupler extensions 9020*a*, 9020*b*. The coupler extension may serve as a conduit to conduct a flow of gas from a gas supply line, such as lumen 9012*a*, 9012*b*. The coupler extension may be removably coupleable with a base portion 9022 of the nasal cannula 9002 and/or the supply line(s) of the cannula. Alternatively, the coupler extension may be integrated with either or both.

Typically, each coupler extension(s) may be configured with a seat portion (e.g. 9024*a*, 9024*b*). The seat portion may include a contact surface for another patient interface. For example, the seat portion can serve as a contact surface for a typical seal forming structure (e.g., a typical face contact cushion) of a mask so as to permit a seal there between. Thus, the contact surface of the seat portion may form a seal with a cushion of a mask. The coupler extension will also typically include a contact surface for skin/facial contact with a patient to form a seal there between. The seat portion can include a surface adapted to minimize or eliminate a cannula induced leak CIL. In some such cases, it may include a surface with a sealing bevel 9090. The sealing bevel 9090 may promote sealing between the cushion of the mask and a facial contact surface. In this way, it may fill a gap that would otherwise be induced by a traditional nasal cannula structure.

Figure 9A:
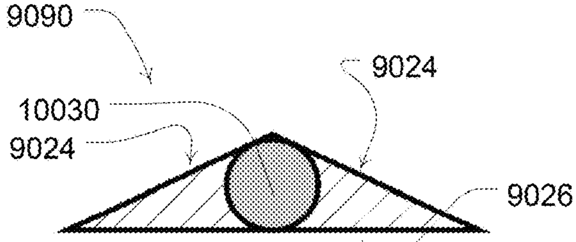
Figure 9C:
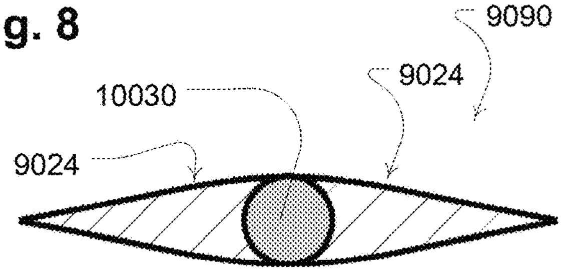
Figure 9B:
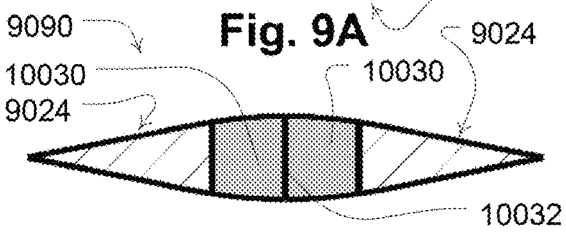
Figure 9D:
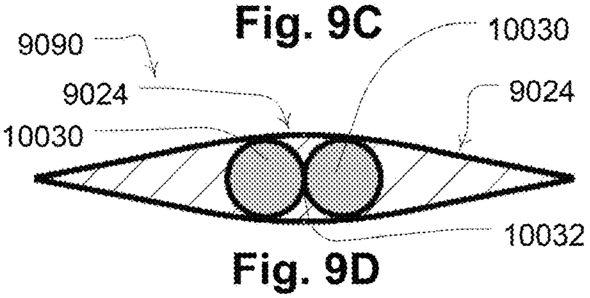

The sealing bevel of the seat portion may be formed with various cross sectional profiles to promote sealing. For example, as illustrated in FIG. 9*a*, the seat portion 9024 of the coupler extension may have a generally triangular cross sectional profile. It may be a triangle, for example an isosceles triangle, with the mask sealing surface on the sides opposite the base. Thus, the sides opposite the base may be equal or of different lengths. The base 9026 may typically be configured as the patient sealing surface. Other cross sectional profiles may also be implemented. For example, FIGS. 9*b*, 9*c* and 9*d* show a lentil cross sectional profile. Thus, as illustrated, the profile may be larger centrally and the top and bottom surfaces may gradually converge by similar slopes toward the opposing ends of the profile.

In some cases, the coupler extension(s) may serve as a conduit for conducting a breathable gas between the prongs of the nasal cannula and lumen. For example, as illustrated in FIGS. 9*a*, 9*b*, 9*c* and 9*d*, the seat portion may include one or more channel conduits 10030. The channel conduits may be employed for directing gas in different gas flow directions with respect to the nasal cannula, to provide gas to different prongs and/or to provide different gases etc. For example, one channel conduit may lead to one prong of the nasal cannula and another channel conduit, if included, may lead to the other prong of the nasal cannula. As shown in FIGS. 9*a* and 9*c*, a single channel conduit is provided. The single channel conduit is round and may couple with a tube shaped lumen. However, it may be other shapes, e.g., rectangular. This channel conduit may lead to both prongs or one prong when coupled with the nasal cannula. As shown in FIGS. 9*b* and 9*d*, a double channel conduit is provided. Each channel of the double channel conduit may have a round, oval or other similar profile and may couple with a tube shaped lumen. Each channel double conduit shown in FIG. 9*b* is rectangular and may be divided by a rib divider structure 10032 centrally located within the coupler extension. Each channel may lead to both prongs or each channel may lead to a different prong when coupled with the nasal cannula. Additional channel conduits may also be provided for example, by providing additional rib dividers. In some forms, the coupler extension(s) may comprise a channel conduit that extends throughout its cross section, such as including the sealing bevel.

As shown in FIGS. 10*a* and 10*b*, when a mask is placed over the nasal cannula, such that the nasal cannula will be contained within the plenum chamber, the mask rests not only on the patient's facial contact areas but also on the seat portion of the nasal cannula. As further illustrated in FIG. 10*b*, the profile of the seat portion permits a seal with the seal forming structure of the mask so as to reduce gaps therebetween, improving sealing. Thus, the seat portion will typically have a length L and width W (see, e.g., FIG. 8 or FIG. 14*a*) adapted to receive typical mask cushions. The length may be longer than a typical cushion width. The length may be chosen to ensure seal during lateral displacement of the mask. A measurement from 0.5 to 3.0 inches may be a suitable length range. For example, an approximately two inch length may be suitable. The width may vary depending on the height of the channel conduits and typical flexibility characteristics of mask cushion materials so as to ensure a gradual sealing bevel that will avoid gaps.

The coupler extension may be formed by moulding, such as with a flexible material. For example, it may be formed of silicone. The coupler extension may comprise a same material and/or a different material to another portion of the cannula. Optionally, the outer or end portions may be more rigid than the central section such as by having a solid cross section, or comprising a material of higher Young's modulus. The greater rigidity at the ends of the cross section may help with limiting their deformation so as to maintain their shape and avoid creation of gaps between the mask cushion and facial contact areas during use. In some versions of the coupler extension additional materials may be applied such as for improving compliance. For example, a skin contact surface may include a foam layer or soft material for improved comfort.

Although the version of the modified nasal cannula of FIG. 10*a* includes a single supply line on each side of the cannula (e.g., left side and right side supply lines), additional supply lines may be implemented. For example, as illustrated in FIGS. 11 and 12, two lumens are applied or protrude from each coupler extension. In some such cases, each lumen may be coupled with a different channel conduit of the coupler extension. In such arrangements, the lumens may be split above and/or below an ear to provide a more secure fitment for the patient.

Optionally, the seat portion of the any of the cannula described herein may include a mask fitment structure, such as a seat ridge. The ridge can serve as a locating feature to indicate, or control, a relative position of the mask with respect to the seat portion. Such a seat ridge 12040 feature is illustrated in FIGS. 11 and 12. The seat ridge may rise from the surface of the seat portion such as on an outer area or edge of the seat portion (in a direction normal to the sagital plane).

FIG. 13 illustrates another version of the coupler extension of the present technology. In this version, the width of the seat portion includes an expansion area EA that expands the seat portion centrally along its length. Such a variation in the contact surface of the seat portion may assist in improving the seal between the seat portion and a mask cushion and/or the comfort of the seal between the coupler extension and the patient's facial contact area.

In some versions of the present technology a coupler extension 15020 may be formed as an add-on component for a traditional nasal cannula. Such an add-on coupler extension may be considered with reference to FIGS. 14*a*-14*c*. The add-on coupler extension 15020 may include one or more groove(s) 15052 for insertion of a supply line such as a lumen of a cannula. Thus, the coupler extension with its seat portion and sealing bevel may be easily applied to or under a lumen of a nasal cannula to reduce gaps when a mask is applied over the lumen of the traditional cannula. The coupler extension 15020 may also include any of the features of the coupler extensions previously described. For example, as shown in FIGS. 14*a*, 14*b*, and 14*c* it may have various cross sectional profiles such as triangular profile and lentil profiles. In the version of FIG. 14*c*, two grooves 1502 are provided for insertion of two lumen such as in the case that the traditional cannula includes two lumen extending out from one or both sides of the cannula. Although the figures have illustrated nasal cannula with two prongs, it will be understood that a nasal cannula of the present technology may be implemented with one or more nasal prongs (e.g., two).

5.6.2 Modified Nasal Pillow Embodiments

In some versions of the present technology, a common patient interface may provide a unitary structure for permitting application of various therapies. Thus, unlike the prior embodiments, the use and periodic application of an additional patient interface for varying therapy may not be necessary. Moreover, features of such a patient interface may be designed to minimize dead space.

One such patient interface example that can be implemented for periodic application of various therapies, for example an oxygen therapy and a PAP therapy, may be considered with reference to FIGS. 15*a* and 15*b*. The patient interface 16002 may serve as a nasal interface. Thus, it may include a set of naris pillows (e.g., one or more naris pillow(s) 16010). Each naris pillow may be flexible and may be configured to form a seal with the naris of a patient when worn. The naris pillow may have an outer conical surface 16012 that may engage at a skin periphery of a patient's naris either internal and/or externally of the nostril. Optionally, the naris pillow may also have an inner conical portion 16014 in a nested relationship with the outer conical portion (best seen in FIG. 17*b*). A gap may exist between the inner conical portion 16014 and the outer conical surface 16012. Each naris pillow may couple by a neck 16015 portion to a common base portion 16016. A passage through the central area of the outer conical portion (and/or inner conical portion), neck and base portion may serve as a flow path to and/or from a flow generator of PAP device 4000 via an air circuit 4170. The air circuit 4170 may be coupled to the base portion 16016 of the patient interface at a flange 16018 (best seen in FIG. 18*b*). Optional base extensions 16020-1, 16020-2 may include connectors 16022-1, 16022-2 for connection of the patient interface with a stabilizing and positioning structure (e.g., straps or other headgear.)

One or both of the naris pillows may also include one or more nasal projections. Each nasal projection 16100 may be a conduit to conduct a flow of gas through the nasal projection. The nasal projection will typically project from the nasal pillow. As illustrated in FIGS. 15*a* and 15*b*, the nasal projection may be configured to extend beyond the seal of the naris pillow (e.g., beyond the edge of the outer conical portion) so that it may project into or extend into the nasal cavity of a patient when used further than the naris pillow at a proximal end PE. The nasal projection 16100 may emanate from within the flow passage of the naris pillow (e.g., extend out of a conical portion). The nasal projection may optionally adhere to, or be formed as a part of, an inside wall of the naris pillow or other internal passage of the patient interface. In some cases, the nasal projection may be integrated with or formed with an inside wall of the naris pillow or other internal passage of the patient interface. Nevertheless, flow passage of the nasal projection will be discrete from the flow passage of the naris pillow. Typically, the length of the extension into a nasal cavity by the nasal projection may be in a range of about 5 mm to 15 mm.

Optionally, as shown in the version of FIGS. 15*a* and 15*b*, each nasal projection may extend through a passage of the naris pillow and a passage of the base portion. At a distal end DE of the nasal projection, the nasal projection may be removeably coupled to (or integrated with) a further conduit to a gas supply, such as a flow generator or supplemental gas source (e.g., an oxygen source). Alternatively, at a distal end DE of the nasal projection, the nasal projection may be open to atmosphere, such as to serve as a vent. In some cases, the distal end DE of the nasal projection may have a removable cap so as to close the distal end and thereby prevent flow through the nasal projection. For example, as illustrated in FIG. 16, a projection conduit 17170-1, 17170-2 may optionally be coupled to each of the nasal projections. Optionally, the projection conduits 17170 extend along and are external of the air circuit 4170. However, these projection conduits may extend along and are internal of the air circuit 4170 such as when they extend from the base portion 16016 and through the flange 16018 as illustrated in FIG. 17*b*.

In some versions of the patient interface 16002, one or more vents may be formed at or from a surface of the patient interface. In other versions, another component (e.g. an adapter or an air circuit 4170) including one or more vents may be fluidly coupled to the patient interface. The vent may serve as a flow passage to vent expired air from the apparatus. Optionally, such a base vent 16220 may be formed on the base portion 16016 as illustrated in FIG. 15*a* so as to vent from the chamber inside the base portion. In some cases, one or more vents may be formed on the naris pillow, such as on the neck 16015. In some cases, one or more vents may be formed on a part of the outer conical surface 16012 such as to vent from the chamber within the naris pillow portion of the patient interface. In some cases, such a vent may be a fixed opening with a known impedance. In some such cases, the vent may provide a known leak. Optionally, such a vent may be adjustable, such as by a manual manipulation, so as to increase or decrease an opening size of the vent. For example, the vent may be adjusted from fully open, partially open and closed positions, etc. In some cases, the vent may be an electro-mechanical vent that may be controlled by the flow generator so as increase or decrease the size of the vent between various opening and closed positions. Example vents and control thereof may be considered in reference to International Patent Application No. PCT/US2012/055148 filed on Sep. 13, 2012 and PCT Patent Application No. PCT/AU2014/000263 filed on Mar. 14, 2014, the entire disclosures of which are incorporated herein by reference.

By way of example, in the patient interface 16002 of FIGS. 17*a* and 17*b*, the nasal interface includes multiple nasal projections 16100 extending from each naris pillow. At least one such nasal projection may serve as a pillow vent 18220 for example, at a bottom portion of the outer conical surface of the naris pillow. In the example, the nasal projections 16100-1 each form a conduit that lead to atmosphere through the naris pillow from the nasal cavity of a patient. With such a nasal projection extending into the nasal cavity, a patient's deadspace can be reduced through a shortened pathway for expired air (carbon dioxide) to be removed from the patient's airways. In some such examples, the additional nasal projections 16100-2 may be coupled with a supplemental gas supply such as a flow of oxygen or a controlled flow of air as discussed in more detail herein. Optionally, such nasal projections of each naris pillow may be formed with a deviating projection (shown in FIG. 17*a* at arrows DB). Such a deviation such that they are further apart at the proximal end when compared to lower portions can assist with holding the extensions within the nasal cavity during use. Thus, they may gently ply within a nasal cavity on opposing sides of the nasal cavity.

5.6.3 Regulating Valves

Some versions of the present technology may include a patient interface (or the conduits thereof) having one or more regulating valves, such as for regulating pressure. For example, such a valve may open at some pressure magnitude (whether positive or negative, such as the same magnitude whether positive or negative). However in some forms, the valve may be configured to open at different pressure magnitudes whether positive or negative. That is, the valve may open at a positive pressure X, and/or at a negative pressure Y where X is not equal to Y. Such operation of the valve may depend on the materials and/or structure of the valve.

Varying such valve characteristics between the positive and negative pressures may allow the patient interface to behave asymmetrically between inspiration and expiration, such as to have different flow characteristics during inspiration and expiration.

One such valve may be a slit valve, such as a valve formed of one or more slits in a delivery conduit such as for a cannula. For example, slits in a silicone component or other suitable elastomeric material (e.g., a block/piece), may be configured to open at a threshold positive and/or negative pressure. The valve defined by the slit(s) may be configured to have a 'spring rate' such that the opening size would be a predetermined function of the pressure (negative and/or positive). Examples of such valves may be considered in reference to FIGS. 26-29.

For example, a cross-type slit valve is illustrated in FIG. 26. In this example, the slit valve 26002 is formed in a respiratory conduit 26000, such as a gas supply line, lumen, nasal cannula, etc. It may be formed through the wall material from the exterior surface EC of the conduit to the interior surface IC of the conduit. In the example, two slits 26004A, 26004B cut into the conduit. However, one or more slits 26004 may be implemented to form one or more such slit valves in the conduit. Such slits form one or more moveable portions 26008A, 26008B, 26008C, 26008D, which may be sections of the wall material of the conduit. In the cross-type version the moveable portion(s) forms a triangular shape. However, other cuts and shapes may be implemented. Generally, the moveable portions may move as a consequence of deformation of the wall conduit in one or more bend regions, such as a bend region 26010P that is approximately parallel to the conduit length or a bend region 26010A formed along an arc of a circular profile of the exterior surface of the conduit. Operation of the slit valve, by movement of the wall section or moveable portions may be considered in reference to FIGS. 27A, 27B and 27C. Such a slit valve may operate for example, as an overpressure regulator and/or an under pressure regulator.

For example, as shown in FIG. 27A, the slit valve is in a closed position, such that little or no gas flow traverses the slit(s) of the valve. Thus, pressurized gas flow may exist in the conduit (illustrated in the figures with arrows) at desired pressures and/or flow rates. As depicted in FIG. 27B, an overpressure condition may exist, for example wherein the gas pressure in the conduit relative to atmospheric gas pressure outside the conduit has exceeded a first threshold pressure. Depending on the slit orientation and/or moveable portion material characteristics (e.g., material elastic modulus, thickness, etc.), the moveable portion may deform outwardly relative to the gas channel of the conduit (e.g., due to the pressure difference) to permit escape of gas/pressure from the conduit through the slits. Thus, one or more moveable portions adjacent the slit may bend in one or more bend regions 27010. Optionally, the moveable portions may return to close the slits (such as due to the resilience of the elastic material of the conduit or moveable portion) to that configuration of FIG. 27A upon reduction of the overpressure condition.

As shown in FIG. 27C, an underpressure condition (e.g., negative pressure) may exist, for example wherein the gas pressure in the conduit relative to atmospheric gas pressure outside the conduit is under a second threshold pressure. Depending on the slit orientation and/or moveable portion material characteristics (e.g., material elastic modulus, thickness, etc.), the moveable portion 26008 may deform inwardly relative to the gas channel of the conduit (e.g., due to the pressure difference) to permit inflow of gas/pressure to the conduit through the slits. Thus, one or more of the moveable portions 26008 adjacent the slit(s) may bend in the one or more bend regions 27010. Optionally, the moveable portions may return to close the slits (such as due to the resilience of the elastic material of the conduit or moveable portion) to that configuration of FIG. 27A upon reduction of the underpressure condition.

A set of valves may comprise equal or unequal thresholds at which a valve may open. For example, a bidirectional slit valve may be configured to open at a first pressure threshold of a first pressure threshold of 15 cm $H_2O$, as well as at a second pressure threshold of −10 cm $H_2O$. In another example, a set of valves may comprise a first valve configured to open at a first pressure threshold of 20 cm $H_2O$ and a second valve configured to open at a second pressure threshold of −20 cm $H_2O$.

The nature of the bend region resulting from the direction of the slits may serve to effect different pressure thresholds. For example, as illustrated in FIG. 26, a bend region 26010P formed along or parallel to a length of the conduit may be more flexible than the bend region 26010A formed along an arc of a circular profile of the exterior surface of the conduit such as for a round/tube type conduit.

In some cases, a slit valve may be formed to be bidirectional, such as to permit movement for the underpressure and overpressure conditions described. However, in some cases a slit valve may be configured to be unidirectional such as to permit operation for only an underpressure condition or only an overpressure condition. In some such cases, the form of the slit may serve to implement the unidirectional and/or bidirectional nature of the slit valve. For example, angling of the slit(s) through the material of the wall of the conduit may be implemented to affect either bidirectional or unidirectional operation. Examples of such slit angling may be considered in reference to FIGS. 28A, 28B and 28C.

For example, two slits of a conduit (e.g., a round tube) may form a moveable portion of a slit valve for bidirectional operation as shown in FIG. 28A. As illustrated, the cuts of the slits are directed toward a center of the conduit. Central axes CA1, CA2 of the slits 26004 in the example may form part of an imaginary angle with a vertex approximately at the center of the cross sectional profile of the conduit. Thus, the moveable portion may move inwardly into the channel and outwardly from the channel without significant interference between the slit edges 28020A, 28020B of the moveable portion and the slit edges 28020C, 28020D of the conduit portion. Such moveable portion(s) may return to close the slits (such as due to the resilience of the elastic material of the conduit or moveable portion) when the overpressure or underpressure conditions are alleviated.

By way of further example, two slits of a conduit (e.g., a round tube) may form a moveable portion of a slit valve for unidirectional operation as shown in FIG. 28B, such as for an overpressure condition. As illustrated, the cuts of the slits are directed toward each other in the conduit such that the edges of the moveable portion or section of the conduit formed by the slits are bevelled inward. In this regard, central axes CA1, CA2 of the slits 26004 in this example may form part of an imaginary angle with a vertex in the conduit but not at the center (non-central) of the cross sectional profile of the conduit. Thus, the moveable portion may move outwardly from the channel (in the event of an overpressure condition of the conduit). Such moveable portion(s) may return to close the slits (such as due to the resilience of the elastic material of the conduit or moveable portion) when the overpressure condition is alleviated. However, the moveable portion will not move inwardly into the channel. Outwardly, there may be little or no significant interference between the slit edges 28020A, 28020B of the moveable portion and the slit edges 28020C, 28020D of the conduit portion. However, inwardly there is significant interference between the slit edges 28020A, 28020B of the moveable portion and the slit edges 28020C, 28020D of the conduit portion such that the angling of the slit edges of the conduit form a stop against inward movement of the moveable portion.

Similarly, two slits of a conduit (e.g., a round tube) may form a moveable portion of a slit valve for unidirectional operation as shown in FIG. 28C, such as for an underpressure condition. As illustrated, the cuts of the slits are directed away from each other in the conduit such that the edges of the moveable portion or section of the conduit formed by the slits are bevelled outward. In this regard, central axes CA1, CA2 of the slits 26004 in this example may form an angle with a vertex outside the conduit of the cross sectional profile of the conduit. Thus, the moveable portion may move inwardly into the channel (in the event of an underpressure condition in the conduit). Such moveable portion(s) may return to close the slits (such as due to the resilience of the elastic material of the conduit or moveable portion) when the underpressure condition is alleviated. However, the moveable portion will not move outwardly from the channel. Inwardly, there may be little or no significant interference between the slit edges 28020A, 28020B of the moveable portion and the slit edges 28020C, 28020D of the conduit portion. However, outwardly there is significant interference between the slit edges 28020A, 28020B of the moveable portion and the slit edges 28020C, 28020D of the conduit portion such that the angling of the slit edges of the conduit form a stop against outward movement of the moveable portion.

Although the angling described previously with respect to the slits may create interference between the edges of the moveable portion and the conduit to serve as a stop, depending on the material characteristics, such interference may serve to provide an increase to the threshold for the valve's response to different pressure conditions of the conduit. Thus, in some cases, bevelled inward slits may serve in a slit valve to respond to an underpressure condition and bevelled outward slits may serve in a slit valve to response to an overpressure condition. In either case, the moveable portion may move to open the slit valve when the pressure condition of the conduit (either underpressure or overpressure relative to ambient) overcomes the friction force of the interference between the slit edges (as well as the rigidity characteristic of the material of the conduit in the bend region (i.e., its resistance to deformation)). Thus, the added frictional force of the slit edge interference can increase the pressure response threshold. In this regard, adjustment of the slit angling can serve as basis for adjusting the pressure response threshold of the slit valve. In some examples, depending on the material and thickness of the conduit, slit depth may be, for example, in a desired range of 5-10 millimeters. However, the slit depth may be out of this range depending on characteristics of the materials and desired performance.

In some versions, a conduit may be formed with multiple different slit valves, such as with different regulating characteristics. One or more optional coupler sheathes 29303 may then be applied by a user or patient to permit selection of the desired regulating vent(s) for operation. Examples are illustrated in reference to FIGS. 29A, 29B and 29C. A conduit may be implemented with several different overpressure slit valves having different regulating characteristics. For example, one or more slit valves may be suitable for use in a certain treatments (e.g., a CPAP treatment or other high pressure treatment) and another for different treatment (e.g., a high flow therapy treatment). Similarly, one or more valves may be suitable for certain patients (e.g., adults with sleep apnea) and other for different patients (e.g., newborn care). In this regard, the different valves may be configured to respond to different overpressure conditions (i.e., different pressure response thresholds).

For example, a valve in a conduit for providing CPAP to a newborn/neonate may be configured to open at a pressure threshold of 8 cm $H_2O$. In another example, a valve in a conduit for providing CPAP to an adult may be configured to open at a pressure threshold of 15 cm $H_2O$. A valve in a conduit for providing HFT to an adult may be configured to open at a pressure threshold of 5 cm $H_2O$. A conduit may thus comprise a set of valves configured to open at pressure thresholds of 5 cm $H_2O$, 8 cm $H_2O$ and 15 cm $H_2O$ for example. It will of course be understood that other pressure thresholds may be also appropriate, wherein the pressure threshold may be varied according to the patient and/or therapy(s) to be applied. One or more coupler sheathes 29303 may then be applied so as to permit the conduit to be used for the different use scenarios. That is, the appropriate valves may be selected/chosen by sheathing the other valves.

Although the previous discussion refers to slit valves, in some version, other vent shapes/vent arrangements may also be suitable.

Generally, valves of the present technology may be used, for example, to mitigate risks against barotrauma (pressure-related trauma) to the patient, and/or to act as an anti-asphyxia valve in some cases. For example, barotrauma may be a risk to infants being treated with high-flow therapy, although it is also possible for other patients under to suffer from barotrauma using other patient interfaces under other therapies (e.g. CPAP). By implementing such valves in a cannula conduit, it can permit minimization of the size of therapy apparatus (i.e., patient interfaces for various therapies), making therapy more comfortable for patients while still enabling safety features. In this regard, such slit valve may beneficially be arranged to be in close proximity to the prongs of a cannula so as to be more responsive to the pressure conditions experienced by the patient. For example, the slits may be arranged on an opposite side of the nasal cannula conduit from which the nasal prongs project (e.g, on the back of the cannula).

The valves may be implemented as primary vents as well, allowing a variable venting rate.

The valves may also be implemented to work in exercise-type applications, where the patient's tidal volume increases greatly. In these applications, additional venting is needed for washout during high-ventilation situations (e.g. during exercise periods). However, allowing the vent flow rate required for exercise application to flow from the patient interface at all times may not be suitable for 'normal' usage. Such an arrangement would lead to an excessively high vent flow rate in comparison to washout requirements, thus leading to wasted outputs from the blower, wasted power and/or oxygen, not to mention an increased noise output and jetting of exhaust gas to the bed-partner. A regulating valve such as the versions described herein could be configured to open according to the increased tidal volume to regulate washout, etc.

5.6.4 Further Nasal Cannula Embodiments

As with other patient interface versions described herein, the patient interface illustrated with reference to FIGS. 30A, 30B and 30C may be used with a flow generator device for either a positive airway pressure (PAP) therapy and/or a high-flow therapy (HFT). In this regard, the flow through the cannula may be measured by a flow sensor and/or a pressure sensor (F/P).

A benefit of HFT is that it may not necessarily require the complexity in blower hardware that is required for a PAP therapy device. This is due to the fact that typical pressures provided by HFT are in 4-8 cm range (typically lower than PAP), and also HFT provides a high flow rate at a near constant pressure without necessarily requiring pressure changes of PAP therapy (e.g., bi-level PAP). Thus, HFT does not necessarily require low blower inertia, which is typically required for changing pressures quickly in PAP when the device is designed to change blower speed so as to accomplish the pressure changes.

HFT with a typical open-type cannula (i.e., a patient interface only employing a prong in each nare that makes no seal with the nare) is desirable for paediatrics, as cannulas (or other 'open' systems) mitigate against risk of overpressure that can be damaging to the patient, and cannulas are typically easier to affix to the patient's face, as the headgear does not need to maintain a pressure seal.

HFT achieves a good washout of respiratory deadspace in patients.

In proposed versions of the cannula type patient interface, a flow of air (whether for a high flow treatment or a positive pressure type treatment) is typically delivered directly to the entrance patient's airways (e.g. through the nares as shown below), arranged such that the vent for exhaust flow is downstream of the air delivery. This is also illustrated in FIG. 30C. Unlike a typical nasal cannula where the exhaust flow occurs between the prong and the individual naris, some versions of the present technology may be implemented with an exhaust vent configured such that flow of air would exit through a flow path of a known impedance.

For example, in one form, the exhaust flow may be vented through a continuous vent in the patient interface. (see, e.g., FIG. 15A) However, in another version, a nare vent 30100 may be implemented such that the vent may be applied directly to each nare, an example of which is depicted in FIG. 30A. The cannula prong may then be engageable inside/around the nose, such as through the nare vent. In this regard, the nare vent 30100 serves as a seal with the internal periphery of a nare and defines a particular exhaust area such as that shown in FIGS. 30B and 30C. The exhaust flow would travel through the periphery of the cannula prong, through the nare vent, where the flow impedance is defined. Given the near proximity of the nare vent to the periphery of the nare (i.e., exhaust location is at the periphery of the nares), there is little or no deadspace added by the nare vent.

The known venting characteristic may be implemented by:

a. The inner seal of the nare vent opening or reducing the patient's nares to a known size; and/or
b. The inner seal of the nare vent including a predetermined vent configuration.

For example, the plan view of FIG. 30A illustrates an example nare vent 30100. The nare vent may be adapted to permit an exhaust flow of expired breathable gas from a respiratory system of a patient and particularly from the nasal cavity NC. The nare vent (e.g, its external periphery) may be configured to seal about the internal periphery IP of a nare of the patient (as shown in FIGS. 30B and 30C) so as to provide a known gas flow characteristic of the exhaust flow. The nare vent may be adapted to receive a prong of a nasal cannula for providing the breathable gas to the respiratory system of the patient via the nasal cavity.

In the version of FIG. 30A, a ring-type outer periphery of the structure serves as a seal for the nare. One or more aperture(s) 30102 then serve as the known vent area, each of which would comprise a known aerodynamic impedance. Optionally, a prong coupler 30104 or holder may be implemented in the nare vent to permit a prong 30108 of a nasal cannula to be engaged by (e.g., within) the nare vent. However, such a coupler may be omitted such that the cannula may reside (float) or be inserted anywhere within the area of the nare vent. While a ring structure is illustrated, other shapes may be implemented such as a shape configured to the typical shape of the nare periphery. Optionally, in some versions, the nare vent may be integrated with a prong of a cannula, such that the prong type nare vent may have a coupler end to be coupled with a cannula delivery conduit (supply line) for use. In some cases as illustrated, each nare vent may be an independent component. However, in some versions, a connector or other connecting structure may be implemented to join two nare vents for use.

There may be benefits of placing a known vent downstream of the patient as well as the prong(s). For example, in this configuration, the flow generator FG flow may be substantially equal (except for any unintentional leak) to the flow received in the patient's nasal cavity (i.e., patient flow). In this regard, the flow does not travel past the vent prior to being delivered to the patient. Thus, there may be reduced gas waste, as well as a reduced risk of re-breathing exhaled gases.

In a typical nasal cannula, a gap between a nasal prong and the naris of the patient may act as a vent, whereby impedance to the flow may be a function of the patient's anatomy. Thus, in a system comprising a typical nasal cannula, a measurement of flow rate is required in addition to a measurement of pressure of the air flow to achieve system control of a target patient flow.

However, in a system such as those described herein comprising a nare vent, pressure at the flow generator FG has a direct correlation to flow at the patient. That is, because the vent characteristic is known, FlowVent=f(PressureFG) (where f is a known function), and in this case, FlowVent=FlowPatient. Thus, using a pressure sensor at the FG, the patient flow rate may be determined. In other words, system control of a target patient flow may then be achieved with a measure of pressure from a pressure sensor.

Still further, such a system creates a compact dual-limb respiratory circuit comprising distinct inspiratory and expiratory limbs. The compact nature of the system may be more comfortable for patients and thereby increase therapy compliance.

Another benefit of creating a predetermined vent within a patient's nares is that a greater pressure differential may be created in the inside of the nose, allowing for splinting of the airways in the nose if required (i.e., having a smaller vent arrangement). Such nare vents may optionally be implemented with the conduit slit vents previously described so as to permit a compact/comfortable system capable of different therapies.

5.7 Dual Therapy Application

As previously described, the patient interface examples can permit an application of various therapies such as a supplemental gas (e.g., oxygen therapy) and/or a positive airway pressure (PAP) therapy, such as a CPAP or bi-level PAP therapy or ventilation, or any other pressure treatment or therapy mentioned in this specification. Such flow or pressure therapies may be supplied by a common apparatus or separate apparatus. Such changes in therapy may be applied with no or minimal changes to the configuration of patient interface on the patient.

For example, a typical flow generator, such as the PAP device 4000 previously described, may be coupled with a delivery conduit (air circuit 4170) to the mask 8008 (see e.g., FIG. 7) or the delivery conduit (air circuit 4170) coupled with the base portion 16016 of the patient interface 16002, so as to control pressure delivered to the mask or the chamber of each naris pillow. In this way, a pressure treatment or therapy can be controlled by a pressure control loop of the PAP device so as to control a measure of pressure to meet a target pressure. The measure of pressure may be determined for example by a pressure sensor. The seal of the mask or the naris pillows will permit the pressure to be controlled at the entrance to the patient's respiratory system.

In some such cases, it may be beneficial to also or alternatively provide a controlled flow of gas or air to the nasal projections. For example, oxygen may be supplied by the one or more prongs 9004*a*, 9004*b* of the nasal cannula FIGS. 6 and 7, or one or more of the nasal projections of FIG. 15 or 17. By way of further example, a high flow therapy (HFT) may be supplied to the one or more prongs 9004*a*, 9004*b* of the nasal cannula of, for example, FIG. 6, 7 or 8, or the nasal projections of the patient interface of FIG. 15 or 17 such as by a flow generator configured to provide HFT. In such a case, an additional flow generator or oxygen flow source may be coupled by a projection conduit 17170 to the nasal projection or may be coupled by one or more lumen 7006 to the prongs 9004. Optionally, the flow of gas to the prongs or nasal projections may be controlled by a flow control loop. For example, the flow can be controlled by a flow control loop of the flow generator device or supplemental gas source so as to control a measure of flow rate of air or oxygen to meet a target flow rate. The measure of flow may be determined for example by a flow sensor. The prongs of the cannula and/or nasal projections can permit a supply of supplemental gas, such as at high flow rates, within the patient's nasal passages.

Accordingly, in some embodiments a common flow generator apparatus may have a controller configured to control flow rate of gas through one or more of the nasal projections and to control the air pressure within the mask or one or more of the naris pillows. In some cases, this control may be simultaneous.

In some cases, changing treatment may require changing of venting characteristics associated with patient interface. For example, in some cases a pressure treatment may be provided with the naris pillows and a PAP device. It may thereafter become desirable to initiate a flow treatment with the nasal projections, such as providing a flow of supplemental oxygen. This change in treatment, which may be processor activated in the case of a common apparatus or manually initiated such as in the case of multiple supply devices, may require an adjustment to a venting characteristic of the patient interface. For example, a manual vent may be opened or opened more so as to compensate for the increased flow of gas to the patient's nares. Alternatively, in the case of an automated vent, a processor may control opening of the vent or opening it more upon activation of the additional flow to the nasal projections. Similar vent control may be initiated upon application of a mask over a cannula such as in the illustration of FIGS. 7*a*, 10*a*, 12 and 13. In the case of termination of such an additional therapy, the vent characteristics may be changed again, such as by manually closing or reducing a vent size or by controlling with a processor a closing or reduction in the vent size of an automatic/electro-mechanical vent.

Various flow path strategies may be implemented to washout exhaled carbon dioxide given such different therapies and the different configurations of the nasal interface. These may be considered with reference to the flow arrows F of the figures. In the example of FIG. 15*a*, either an inspiratory flow (i.e., cyclical supply activation) or a continuous flow may be supplied toward the patient nasal cavity via both of the nasal projections 16100 that may be inhaled by the patient during inspiration. The distal ends of the nasal projections may be coupled with further supply conduits such as that illustrated in FIG. 16. Expiratory gases may be exhausted from the patient nasal cavities into the passage of the naris pillows and out through any one or more of the optional base vent 16220 and/or pillow vent(s) 18220. The control of a continuous exhaust flow via such vents during both inspiration and expiration can assist in ensuring washout of expiratory gases from the nasal cavities.

In the example of FIG. 15*b*, either an inspiratory flow (i.e., cyclical supply activation) or a continuous flow is supplied toward the patient nasal cavity via one of the nasal projections 16100 that may be inhaled by the patient during inspiration. In this example, although not shown in FIG. 15*b*, the distal end of the nasal projection on the left of the drawing may be coupled to a further supply conduit and a gas source. This flow supply nasal projection is shown on the left side of FIG. 15*b* but may alternatively be on the right. Expiratory gases may then be exhausted from the patient nasal cavities via the other nasal projection 16100 (e.g., shown on the right of the figure). In this case, the distal end of one nasal projection may omit a further conduit and serve as a pillow vent at the proximity of the naris pillow 16010. The control of a continuous exhaust flow via such a vent during both inspiration and expiration can assist in ensuring washout of expiratory gases from the nasal cavities.

In the example of FIGS. 17*a* and 17*b*, the presence of dual nasal projections permit venting and supply via the nasal projections in each naris. Thus, either an inspiratory flow (i.e., cyclical supply activation) or a continuous flow is supplied toward the patient nasal cavity via one of the nasal projections 16100 of each naris pillow that may be inhaled by the patient during inspiration. In this example, although not shown in FIG. 17*b*, the distal end of one nasal projection of each naris pillow may be coupled to a further supply conduit and a gas source. Expiratory gases may then be exhausted from the patient nasal cavities via the other nasal projection 16100 of each naris. In this case, the distal end of one nasal projection of each naris may omit a further conduit and serve as a pillow vent 18220 at the proximity of the naris pillow 16010. The control of a continuous exhaust flow via such vents during both inspiration and expiration can assist in improving washout of expiratory gases (such as carbon dioxide) from the nasal cavities.

In some cases, the washout flow path may be implemented with a unitary nasal projection in each naris pillow. Such an example may be considered in relation to FIG. 18. In this example, a gas supply nasal projection is omitted. The unitary nasal projection in each naris pillow may then serve as a nasal projection vent, such as by venting as a pillow vent. Thus, either an inspiratory flow (i.e., cyclical supply activation) or a continuous flow is supplied toward the patient nasal cavity via each naris pillow so that it may be inhaled by the patient during inspiration. In this example, the distal end of the unitary nasal projection may omit a further conduit and serve as a pillow vent 18220 at the proximity of the naris pillow 16010. The control of a continuous exhaust flow via such vents during both inspiration and expiration can assist in ensuring washout of expiratory gases from the nasal cavities.

In some cases, the washout flow path may be implemented without nasal projections. Such an example may be considered in relation to the nasal pillows of FIGS. 19*a* and 19*b*. In this example, each naris pillow may have a pillow vent for venting expiratory gases during expiration (See FIG. 19*b*). The pillow vent may be open during inspiration and expiration or only open during expiration. Either an inspiratory flow (i.e., cyclical supply activation) or a continuous flow is supplied toward the patient nasal cavity via each naris pillow so that it may be inhaled by the patient during inspiration (See FIG. 19*a*). The control of a continuous exhaust flow via such vents during both inspiration and expiration can assist in ensuring washout of expiratory gases from the nasal cavities. However, in the absence of the nasal projection there is a marginal increase in the deadspace.

In the example of FIGS. 20*a* and 20*b*, vents at the neck or base of each naris pillow may be activated by an optional vent valve 21410. These naris pillows may optionally include any of the nasal projections previously described. In this version, the vent valve may be activated by rising pressure associated with the patient's expiratory cycle so as to permit cyclical venting at the patient's naris pillow. Thus, as illustrated in FIG. 20*a*, during expiration, expiratory gases open the vent valve to expel expiratory air to atmosphere. At this time, the flow path from the air circuit 4170 to the naris pillow may be blocked. As illustrated in FIG. 20*b*, during inspiration, supply gas from the flow generator or PAP device may close the vent valve. At this time, the flow path from the air circuit 4170 to the naris pillow may be open.

In another example of FIGS. 20*c* and 20*d*, such valves 21410 may be configured so that only some of the pillow vents 18220 are closed at any one time. In this arrangement, the valves 21410 may be configured so that one pillow vent is opened, while the other is closed. Referring now to FIG. 20*c*, the pillow vent to the left of the figure is open, while the pillow vent to the right is closed, and thus expiratory flow from the patient exits through the open pillow vent. During inhalation, as shown in FIG. 20*d*, the flow generator or PAP device delivers a flow of supply gas, which is delivered to the patient while the pillow vent to the left remains open, thereby continuously washing out of gases which has the effect of reducing dead space. An alternative arrangement is shown in FIGS. 20*e* and 20*f*, wherein the pillow vent to the left is closed and the pillow vent to the right is open. In one form, the valves 21410 may be arranged so that they are switchable from a first arrangement, for example shown in FIGS. 20*c* and 20*d* to a second arrangement for example shown in FIGS. 20*e* and 20*f*. For example, in the case of an electromagnetic operation of the valves, they may be set to the desired operation by a controller. For example, they may be alternated on a predetermined or preset time cycle. Optionally, the valves may be manually operated and may be manually switched at a desired time.

One advantage of switching from the first to the second arrangement and thus alternating between the left and right nasal passages as described above may be that it may improve the patient's comfort level. For instance, the patient using the patient interface as shown in FIGS. 20*c*-20*d* may experience discomfort from drying out of the patient's right (left on the figure) nasal passage, which may be alleviated by changing the configuration of the patient interface to that shown in FIGS. 20*e*-20*f*.

Optionally, such a valve may be extended into a nasal projection (e.g. shown in FIG. 21) such that the nasal projection may serve as both supply and exhaust conduit. In such a case, the nasal projection may include a valve membrane 22550 that divides the conduit. The valve membrane 22550 may be flexible and extend along the nasal projection 16100 from or near the proximal end toward an vent portion 22510 of the nasal projection. The vent portion may be proximate to or serve as a pillow vent 18220. The valve membrane 22550 of the nasal projection may be responsive to inspiratory and expiratory flow such that it may move (See Arrow M of FIG. 22) dynamically across the channel of the nasal projection as illustrated in FIGS. 22, 23*a* and 23*b*. The valve membrane may then dynamically reconfigure the nasal projection as an inspiratory conduit and expiratory conduit on either side of the membrane. For example, as shown in FIG. 23*a*, responsive to patient expiration, movement of the valve membrane 22550 across the proximal end of the nasal projection enlarges an expiratory channel portion ECP of the projection that leads to the vent portion 22510. This movement thereby reduces an inspiratory channel portion ICP of the nasal projection that leads to a supply gas source or flow generator. Similarly, as shown in FIG. 23*b*, responsive to patient inspiration, return movement of the valve membrane 22550 across the proximal end of the nasal projection reduces an expiratory channel portion ECP of the projection that leads to the vent portion 22510. This movement thereby expands an inspiratory channel portion ICP of the nasal projection that leads to a supply gas source or flow generator.

In another form, a patient interface such as a mouth and nose mask may comprise one more flow directors configured to deliver a flow of gas towards the naris of the user. The flow directors may be connected to, and receive the flow of gas from a supplementary gas source such as an oxygen source or a flow generator suitable for HFT. For example, the patient interface may comprise one or more secondary ports 19100 as shown in FIG. 24 connectable to the supplementary gas source such as via a supply conduit.

One example of the flow directors may be one or more tubes 19200 coupled to one or more secondary ports 19100 and located outside of a naris of a patient to direct the flow of gas as shown in FIG. 25*a*. The one or more tubes 19200 may be a separable component which can be engaged with the frame of the patient interface (e.g. mask) as shown in FIG. 25*a*, where the tubes 19200 are engaged within the plenum chamber 3200. In some forms, the one or more tubes 19200 may be integrally formed with another portion of the patient interface such as the plenum chamber 3200. The one or more tubes 19200 may be movably configured relative to the rest of the patient interface, such as pivotably coupled to the mask as shown in FIG. 25*a*, to be able to adjust the direction of the flow of gas. Thus, unlike the loose prongs of typical nasal cannula when used with a mask, the flow director being moveably configured relative the patient interface, permits control of the flow inside the patient interface. This can avoid the difficulty of having to place nasal cannula on a patient before placement of the mask, such as when a mask is used simultaneously with a nasal cannula. It can also avoid the problem of the nasal cannula becoming dislodged from the patient's nares under the mask.

A flow director may further comprise a locating feature to allow the flow director to remain in place once it has been adjusted, for example by frictional engagement with the plenum chamber 3200. Although the arrangement shown in FIG. 25*a* shows two such tubes that are fluidly connected to each other, as well as to the secondary ports 19100, it will be understood that any number of ports and tubes may be used, as well as any combination of connections therebetween, analogously with the above descriptions of nasal projections. In another example, each tube 19200 may be independently connected to the plenum chamber 3200 using hollow spherical joints (not shown) which allow a flow of gas therethrough, while also allowing movements of the tube relative to the rest of the patient interface. Such a connection may thereby allow a flow of gas to travel between a secondary port 19100 and the tube 19200.

In some cases, a flow director may be in a form of a flow directing surface 19300 coupled to a secondary port 19100. For instance, each flow directing surface shown in FIG. 25*b* may comprise a curved surface shaped to direct the flow of gas from the supplementary gas source using the Coanda effect, whereby the flow "attaches" or conforms to the curved surface and follows its profile. In some forms, the flow directing surface 19300 may be movably configured, for example by being rotatably coupled to the plenum chamber 3200 or frame.

According to another aspect, a flow director or a nasal projection may comprise a flow element, such as a honeycomb grid (not shown), to reduce turbulence of the flow, whereby the flow director produces a more laminar flow than otherwise. Such an arrangement may be particularly advantageous when used in conjunction with a flow director, as a laminar flow may be more focussed in comparison to a turbulent flow as it exits out of an orifice. Accordingly, use of a flow element may assist in delivering a greater proportion of the flow of gas to the naris of the patient, whereas without a flow element, more of the flow of gas may be lost to the interior of the mask and possibly washed out through a vent.

In a further example, the flow director(s) (e.g., a right flow director for the right nare and/or a left nasal flow director for the left nare, may be dynamically moveable so as to be adjustable for optimally directing flow into a patient's nares. The dynamic movement may be responsive to the respiratory flow of a user/patient. Examples may be considered with reference to FIGS. 31A, 31B, 31C and 31D. As illustrated, the flow director may include self-aligning nozzle 31002 configured to align dynamically in accordance with patient respiratory flow such as the inspiratory flow of the patient. Optionally, the flow director may be configured such that no movement occurs in response to expiratory flow.

As illustrated in the figures, the flow director 31000 may include one or more vane(s) 31004 or other flow responsive element (e.g., umbrella-like or parachute-like flow responsive structure). The vane may optionally be directionally collapsible so as to permit application of a sufficient flow force for movement of the flow director (e.g., nozzle) during inspiration flow but no or insufficient flow force for movement of the nozzle during expiration (or vice versa). Thus, as illustrated in FIG. 31A, during inspiration, inspirational flow on the vane may open the vane and apply a force to pivot the flow director, such as on a ball joint 31008, to align the director to direct flow from the nozzle into the patient's nare. In the example of FIG. 31, the vane includes a vane extension 31006. The vane extension may permit the vane to be located distally from the nozzle, such as to permit it to project within a nasal cavity NC while the nozzle remains located outside of the nasal cavity and/or to reduce the impact of flow emanating from the flow nozzle. Thus, the extension may permit the nozzle to be located in an optional plenum chamber (not shown in FIG. 31A) of a mask frame while the vane extends into the nasal cavity. However, in some versions, the vane or flow responsive structure may be applied to the surface of the prong or nozzle of the nasal cannula. During expiration as illustrated in FIG. 31B, expiratory flow may cause the vane to retract or collapse responsive to the expiratory flow so as to minimize the force applied to the nozzle of the flow director and thereby minimize or eliminate movement of the flow director during expiration. As shown in FIG. 31C, the vane (with or without a vane extension) may also be positioned outside of the nasal cavity during use. Optionally, as shown in FIG. 31D, the vane and nozzle may be positioned to extend within the nasal cavity NA.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may refer to atmospheric air as well as other breathable gases. For instance, air supplied to a patient may be atmospheric air, and in other forms of the present technology atmospheric air may be supplemented with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g. acoustic) noise may be considered to be the background noise level in the room where a patient is located, other than for example, noise generated by a PAP device or emanating from a mask or patient interface. Ambient noise may be generated by sources outside the room.

5.8.2 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricula or Pinna: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.8.3 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.4 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.5 Aspects of PAP Devices

APAP: Automatic Positive Airway Pressure. Positive airway pressure that is continually adjustable between minimum and maximum limits, depending on the presence or absence of indications of SDB events.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller that has ventilation as an input, a target ventilation as the set point, and level of pressure support as an output. Other forms of input may be one or more of oxygen saturation ($SaO_2$), partial pressure of carbon dioxide ($PCO_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure. A flow controller may be configured to control a blower or other gas source to deliver air or gas at a particular flow rate.

Therapy: Therapy in the present context may be one or more of positive pressure therapy, oxygen therapy, carbon dioxide therapy, control of dead space, and the administration of a drug.

5.8.6 Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: A parameter of a ventilator that establishes the minimum respiration rate (typically in number of breaths per minute) that the ventilator will deliver to the patient, if not otherwise triggered.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation has a target ventilation, and which adjusts the level of pressure support to bring the patient ventilation towards the target ventilation.

Spontaneous/Timed (S/T)—A mode of a ventilator or other device that attempts to detect the initiation of a breath of a spontaneously breathing patient. If however, the device is unable to detect a breath within a predetermined period of time, the device will automatically initiate delivery of the breath.

Triggered: When a ventilator delivers a breath of air to a spontaneously breathing patient, it is said to be triggered to do so at the initiation of the respiratory portion of the breathing cycle by the patient's efforts.

Ventilator: A mechanical device that provides pressure support to a patient to perform some or all of the work of breathing.

5.8.7 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.9 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein may have been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. Apparatus for delivery of a flow of breathable gas to a patient's airways comprising:

a frame including a plenum chamber, the plenum chamber comprising an external side and an internal side, the internal side configured to provide at least a portion of a space for the patient's nose and mouth when worn in use for pneumatically coupling with the patient's nose and mouth, the plenum chamber adapted with first and second connection ports at the external side of the plenum chamber coupling with therapy delivery apparatus to provide, respectively, a first therapy flow inlet into the plenum chamber from the therapy delivery apparatus and a second therapy flow inlet into the plenum chamber from the therapy delivery apparatus, the frame including at least one flow director within the plenum chamber, the at least one flow director configured to direct a gas flow at a naris of a user via an opening end of the at least one flow director, wherein the at least one flow director is within the internal side of the plenum chamber and configured to, in use, release the directed gas flow from the at least one flow director to the naris of the user, wherein the opening end is within the internal side of the plenum chamber, wherein the at least one flow director is in fluid communication with at least one connection port of the first and second connection ports so that the at least one connection port provides the second therapy flow inlet for passing therapy flow for inspiration into the at least one flow director and then into the plenum chamber from the opening end, wherein the at least one flow director is connected to the plenum chamber by a hollow spherical joint.

2. The apparatus of claim 1 further comprising another flow director within the plenum chamber, the another flow director configured within the plenum chamber to direct the gas flow at another naris of the user.

3. The apparatus of claim 2 wherein each flow director is adapted to pivot for adjusting a direction of the gas flow from the flow directors.

4. The apparatus of claim 2 wherein each flow director comprises a tubular conduit.

5. The apparatus of claim 2 wherein each flow director comprises a directing surface.

6. The apparatus of claim 5 wherein the directing surface is adapted as a swivel to change a flow direction attributable to the directing surface.

7. The apparatus of claim 2 wherein the another flow director is independently connected to the plenum chamber by a hollow spherical joint.

8. The apparatus of claim 1 wherein the at least one flow director comprises a self-aligning nozzle configured to align dynamically in accordance with inspiratory flow.

9. The apparatus of claim 8 wherein the at least one flow director comprises a vane.

10. The apparatus of claim 8 wherein the at least one flow director comprises a vane extension.

11. The apparatus of claim 9 wherein the at least one flow director comprises a ball joint for rotation of the nozzle in response to an inspiratory flow force applied to the vane.

12. The apparatus of claim 1 further comprising the therapy delivery apparatus, the therapy delivery apparatus comprising one or more flow generators, wherein the one or more flow generators include one or more controllers configured to control a pressure therapy provided via a delivery conduit to the plenum chamber so as to control a measure of pressure to meet a target pressure, and wherein the one or more controllers are further configured to control a flow therapy provided to the at least one flow director.

13. The apparatus of claim 12 wherein the one or more controllers are configured to control the flow therapy with a flow control loop that controls a measure of flow rate of breathable gas to meet a target flow rate.

14. The apparatus of claim 13 wherein the flow therapy comprises supplemental oxygen.

15. The apparatus of claim 13 wherein the flow therapy comprises high flow therapy.

16. A method of apparatus for delivery of a flow of breathable gas to a patient comprising:

generating control signals with one or more controllers to operate therapy delivery apparatus comprising one or more flow generators to produce a flow of breathable gas for a patient's airways via a patient interface apparatus comprising a frame including a plenum chamber, the plenum chamber comprising an external side and an internal side, the internal side configured to provide at least a portion of a space for the patient's nose and mouth when worn in use for pneumatically coupling with the patient's nose and mouth, the plenum chamber adapted with first and second connection ports at the external side of the plenum chamber for coupling with the therapy delivery apparatus to provide, respectively, a first therapy flow inlet into the plenum chamber from the therapy delivery apparatus and a second therapy flow inlet into the plenum chamber from the therapy apparatus, the frame including at least one flow director within the plenum chamber, the at least one flow director configured to direct a gas flow at a naris of a user via an opening end of the at least one flow director, wherein the at least one flow director is within the internal side of the plenum chamber and configured to, in use, release the directed gas flow from at least one flow director to the naris of the user, wherein the opening end is within the internal side of the plenum chamber, wherein the at least one flow director is in fluid communication with at least one connection port of the first and second connection ports so that the at least one connection port provides the second therapy flow inlet for passing therapy flow for inspiration into the at least one flow director and then into the plenum chamber from the opening end, and wherein the at least one flow director is connected to the plenum chamber by a hollow spherical joint;

measuring a flow rate of the breathable gas with a flow rate sensor; and measuring a pressure of the breathable gas with a pressure sensor;

wherein the one or more controllers controls a pressure therapy via a delivery conduit to the plenum chamber so that the measured pressure meets a target pressure in a pressure control loop, and wherein the one or more controller controls a flow therapy to the at least one flow director.

17. The method of claim 16 wherein the one or more controllers controls the flow therapy so that the measured flow rate meets a target flow rate in a flow control loop.

18. The method of claim 17 wherein the flow therapy provides supplemental oxygen.

19. The method of claim 17 wherein the flow therapy provides high flow therapy.

20. The method of claim 19 wherein the control of the flow therapy and the control of the pressure therapy operate at the same time.

* * * * *